(12) United States Patent
Yamamoto et al.

(10) Patent No.: US 7,322,960 B2
(45) Date of Patent: Jan. 29, 2008

(54) CATHETER WITH PUNCTURE SENSOR

(75) Inventors: Takashi Yamamoto, Ebina (JP);
Yoshitaka Oomura, Hadano (JP);
Yukinori Kubotera, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 282 days.

(21) Appl. No.: 10/809,497

(22) Filed: Mar. 26, 2004

(65) Prior Publication Data

US 2004/0260241 A1  Dec. 23, 2004

(30) Foreign Application Priority Data

Mar. 26, 2003 (JP) ............... 2003-085435
Mar. 28, 2003 (JP) ............... 2003-090226
Feb. 20, 2004 (JP) ............... 2004-044320

(51) Int. Cl.
*A61M 5/00* (2006.01)

(52) U.S. Cl. ................ 604/117; 604/507

(58) Field of Classification Search ........... 604/164.1, 604/117, 164.01, 66, 507, 506
See application file for complete search history.

(56) References Cited

U.S. PATENT DOCUMENTS

| | | | |
|---|---|---|---|
| 5,078,714 A | | 1/1992 | Katims |
| 6,059,726 A | * | 5/2000 | Lee et al. ............ 600/439 |
| 6,086,582 A | * | 7/2000 | Altman et al. ......... 606/41 |
| 6,165,164 A | * | 12/2000 | Hill et al. ............ 604/523 |
| 6,190,360 B1 | * | 2/2001 | Iancea et al. .......... 604/164.09 |
| 6,309,370 B1 | * | 10/2001 | Haim et al. ............ 604/66 |
| 6,391,005 B1 | * | 5/2002 | Lum et al. ............ 604/117 |
| 2001/0031942 A1 | * | 10/2001 | Tollner et al. .......... 604/22 |
| 2002/0183738 A1 | * | 12/2002 | Chee et al. ............ 606/41 |
| 2003/0028172 A1 | * | 2/2003 | Epstein et al. .......... 604/507 |
| 2003/0032936 A1 | * | 2/2003 | Lederman ............. 604/507 |

FOREIGN PATENT DOCUMENTS

| | | |
|---|---|---|
| EP | 1 264 610 | 12/2002 |
| JP | 2002-28247 | 1/2002 |
| WO | 94/00050 | 1/1994 |
| WO | 98/48722 | 11/1998 |
| WO | WO 99/04851 | 2/1999 |
| WO | WO 9904851 A1 * | 2/1999 |

* cited by examiner

*Primary Examiner*—Nicholas D. Lucchesi
*Assistant Examiner*—Laura Bouchelle
(74) *Attorney, Agent, or Firm*—Buchanan Ingersoll & Rooney PC

(57) ABSTRACT

A catheter for percutaneous insertion includes a sheath portion, an insertion member, an injection needle, and paired electrodes. The sheath portion has a lumen extending therein. The insertion member is disposed slidably in the lumen of the sheath portion and provided with a distal end portion capable of protruding from a distal end portion of the sheath portion. The injection needle is disposed in the distal end portion of the insertion member for injecting a therapeutic composition to a target tissue. The paired electrodes are disposed in a distal end portion of the catheter for measuring impedance.

15 Claims, 34 Drawing Sheets

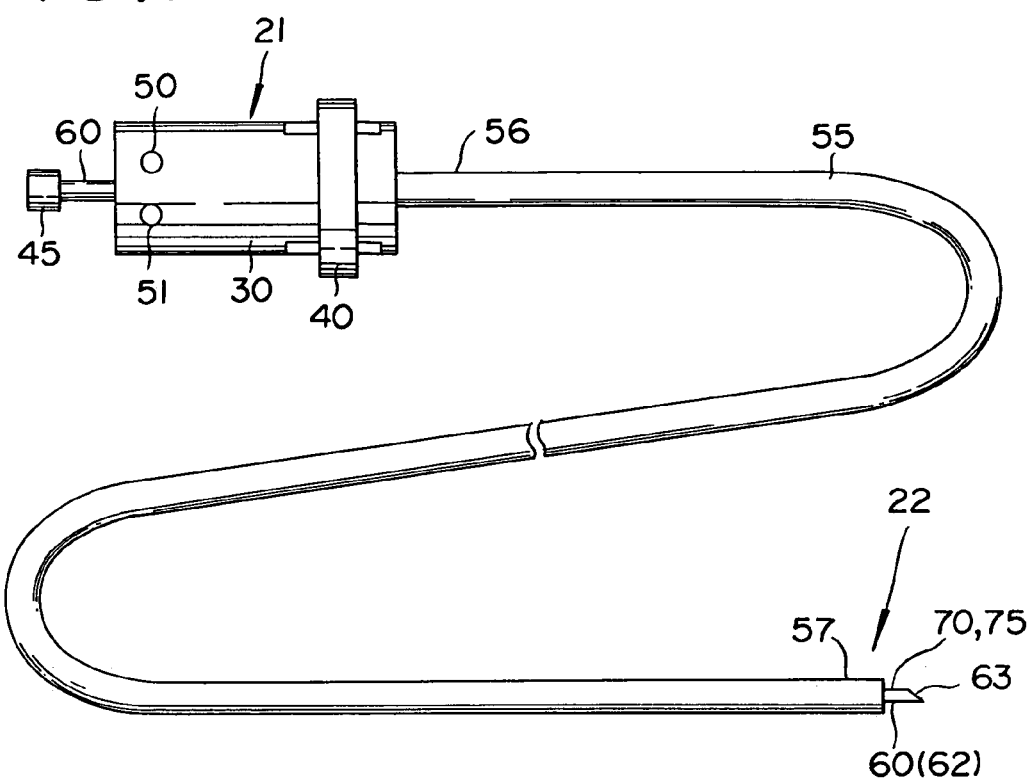
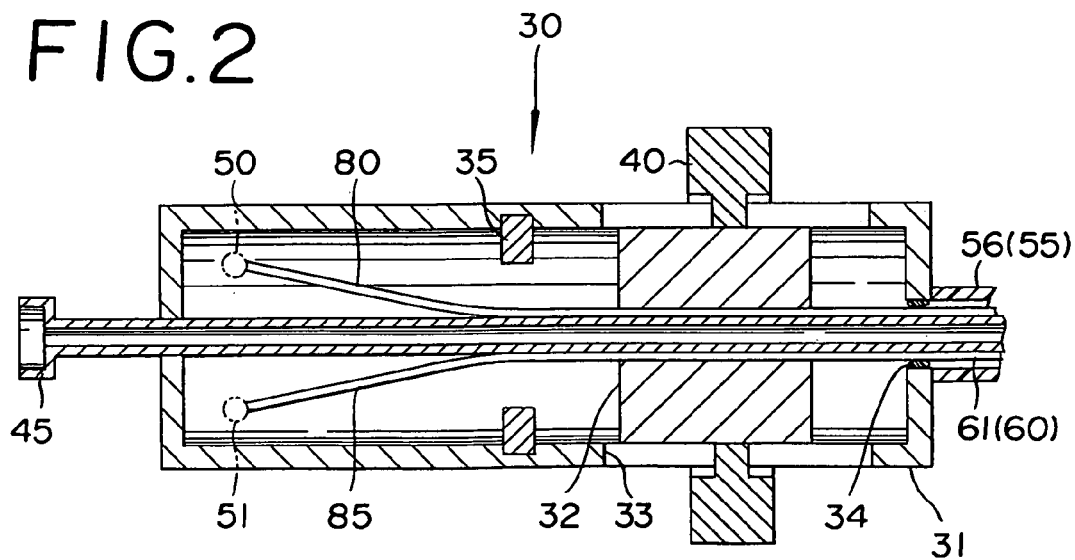

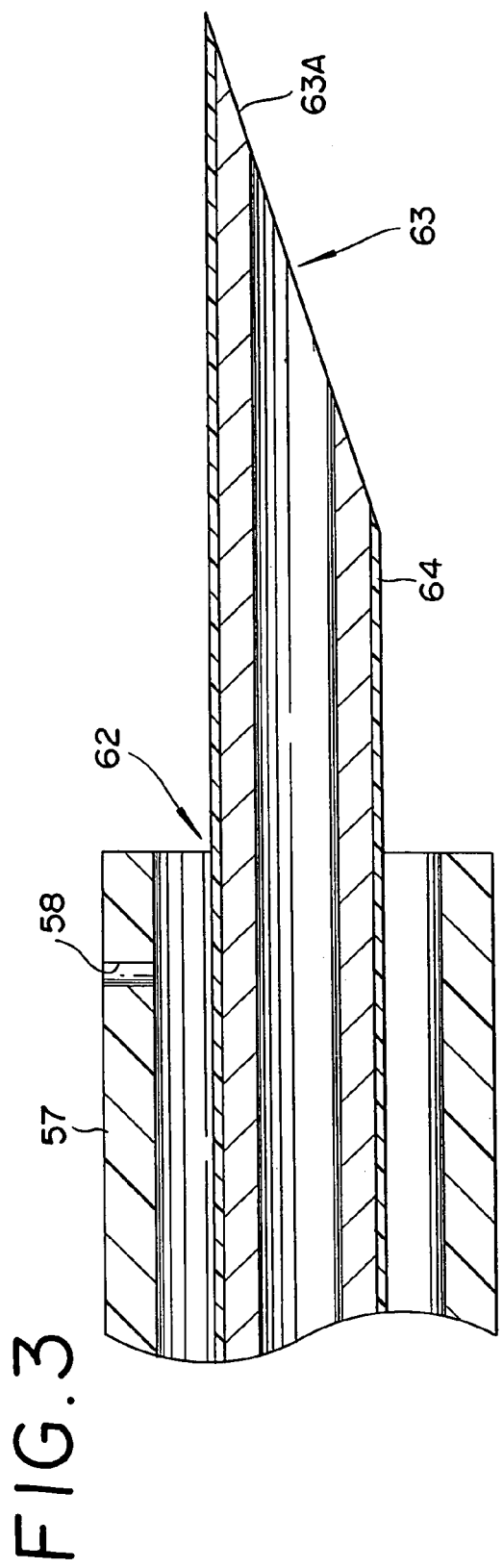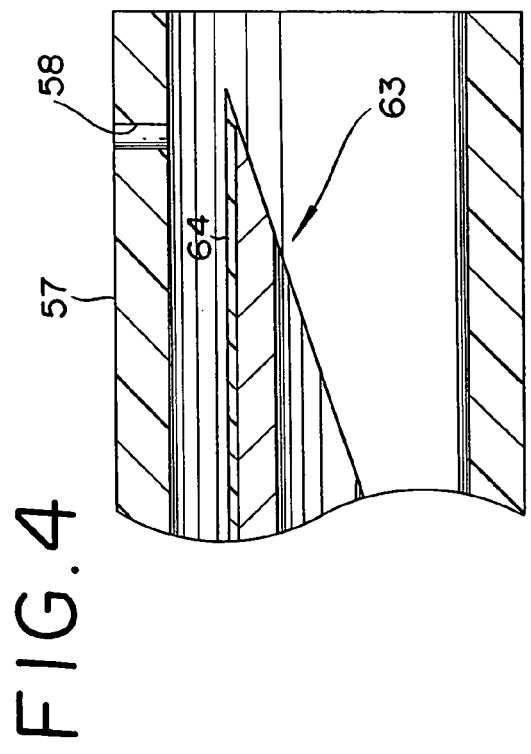
FIG. 3
FIG. 4

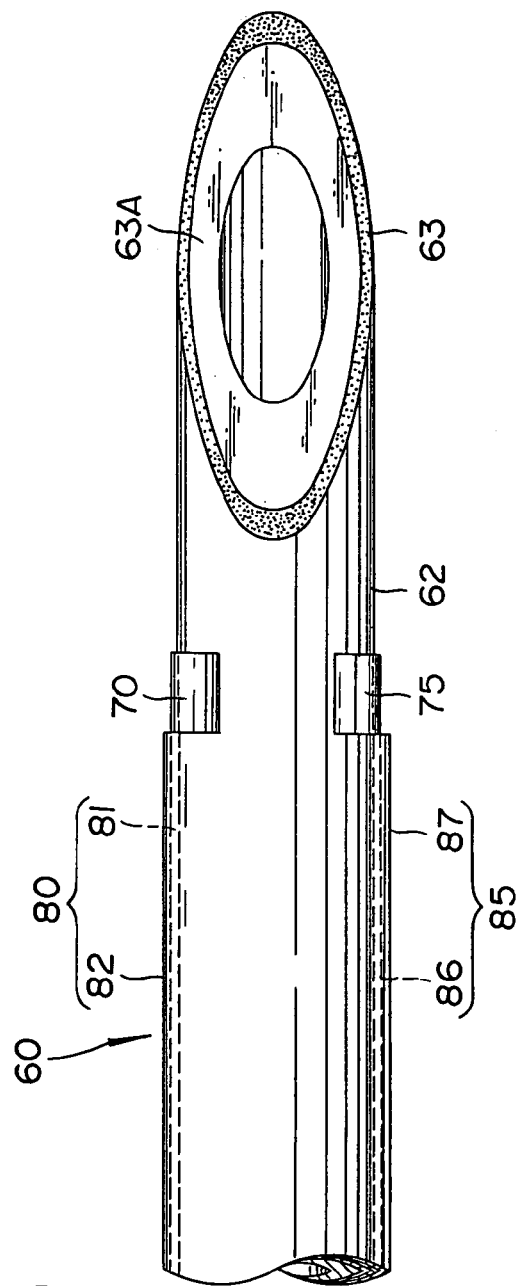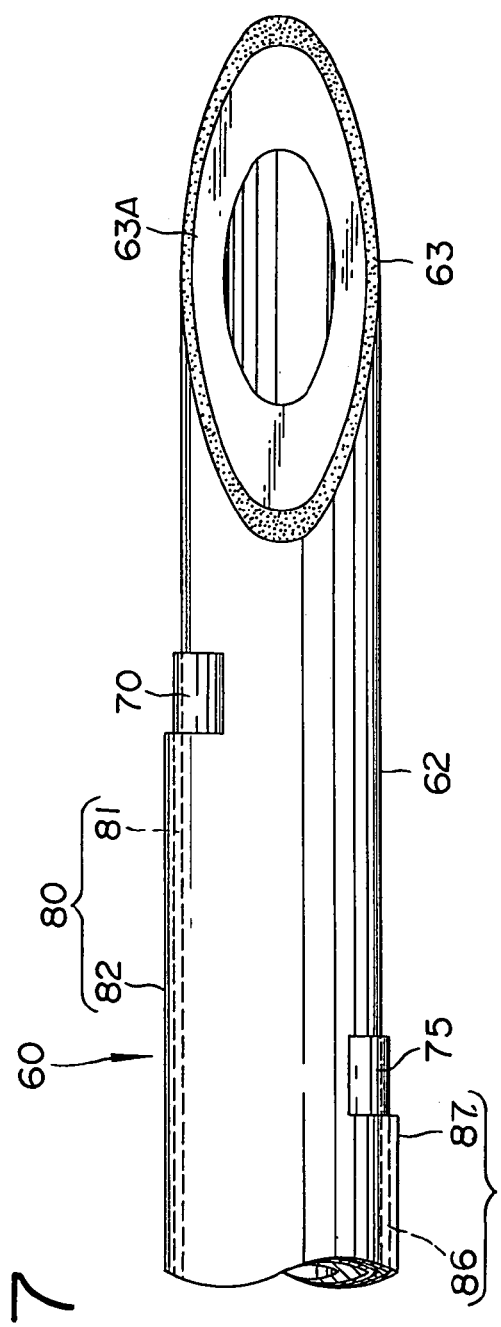

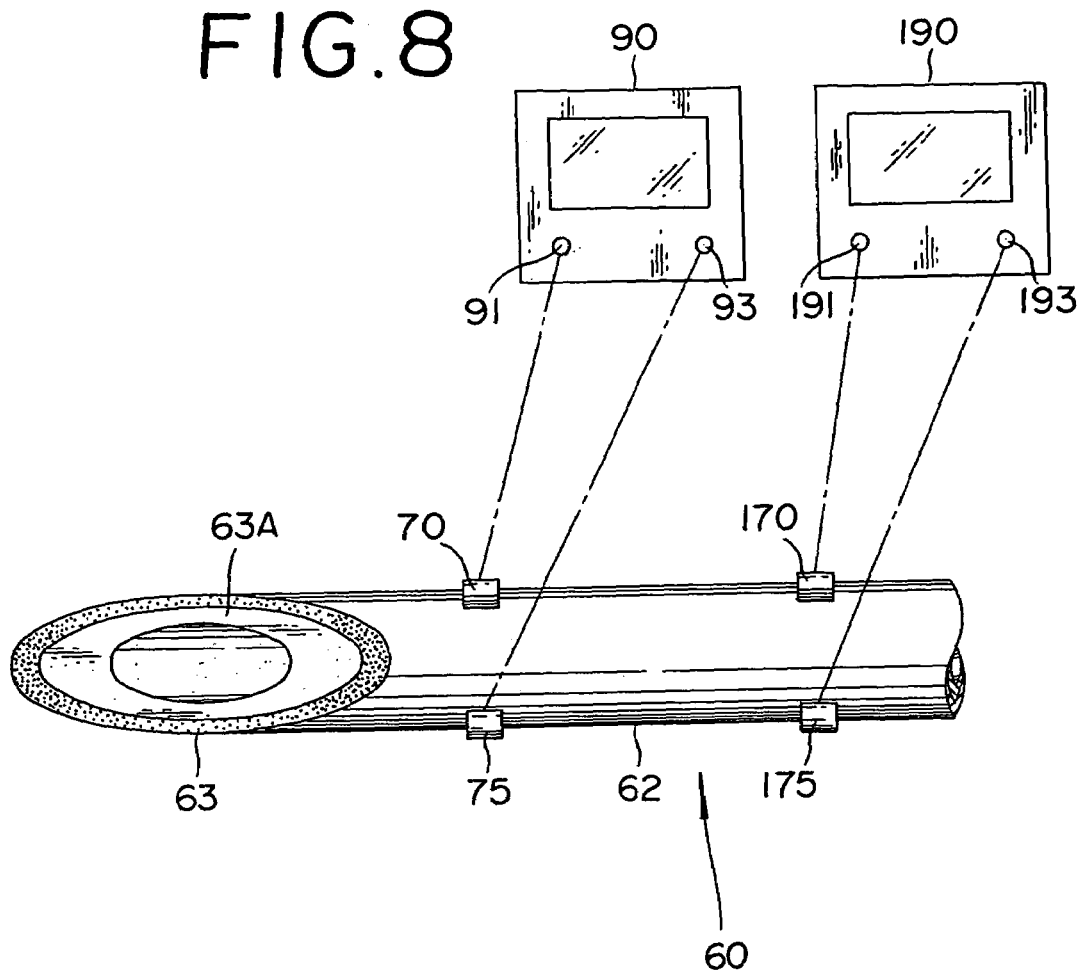

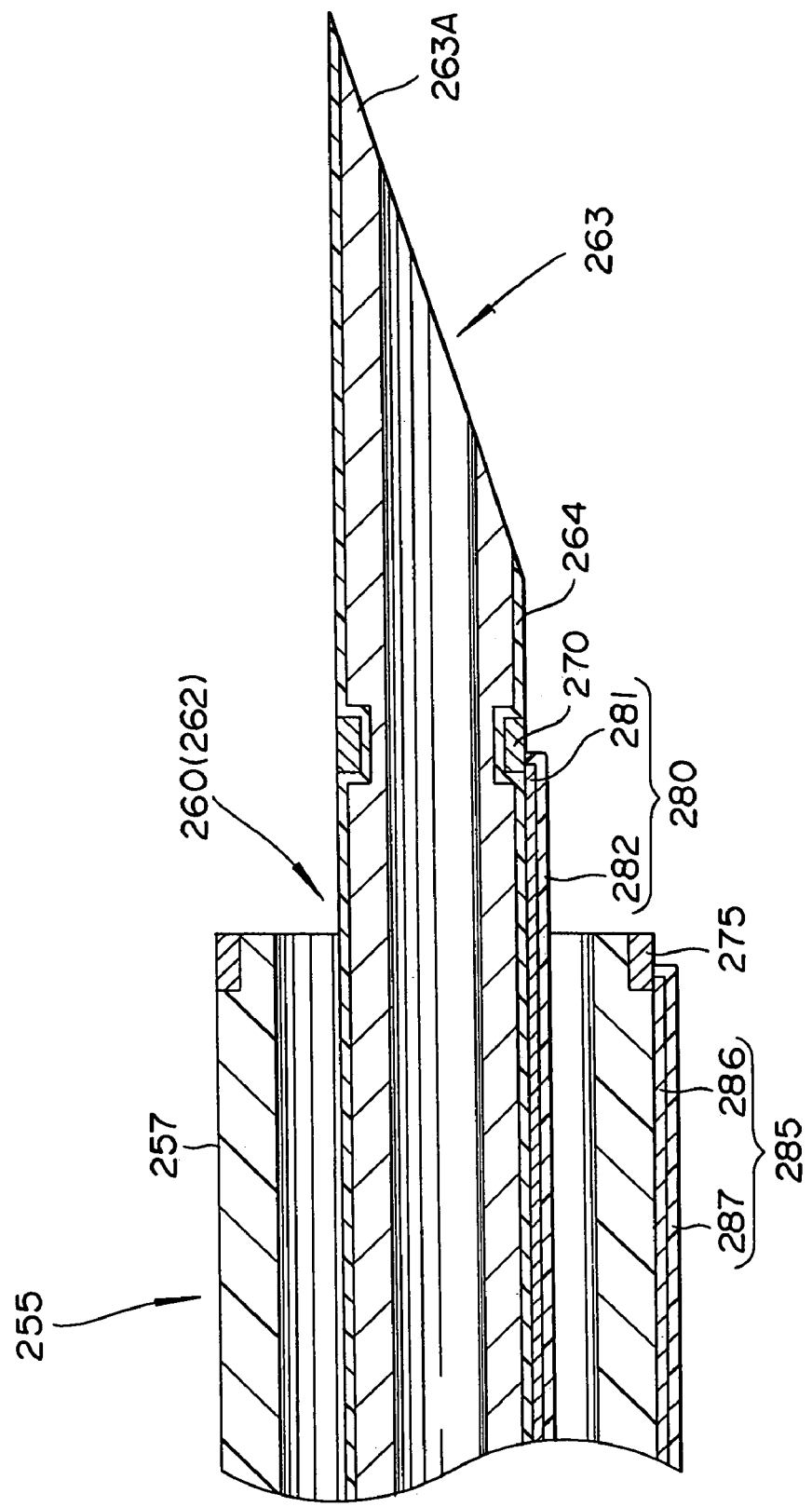

CATHETER WITH PUNCTURE SENSOR

BACKGROUND OF THE INVENTION

1. Field of the Invention

This invention relates to a catheter for injecting a therapeutic composition to the diseased part in a living body, particularly to the ischemic region of the heart or the proximal part thereof.

2. Description of the Related Art

The patients of ischemic cardiopathy are increasing year after year owing to the growth of risk factors such as the inclination of eating habits toward the Western style and the aggravation of social stress. Particularly the increase of patients of serious heart failure has been posing a grave problem in advanced countries. Globally, 15 million new patients are occurring in a year.

As ways of curing such ischemic cardiopathy, studies on the gene therapy and the cell therapy have been under way. The conventional catheters which are applicable to such therapeutic methods are provided at the distal end portions thereof with an injection needle intended for injecting a therapeutic composition.

They are disclosed in U.S. Pat. No. 5,405,376 (corresponding to Japanese Unexamined Patent Publication No. Hei 8-508917) (Patent Reference 1), U.S. Pat. No. 5,797,870 (Patent Reference 2), U.S. Pat. No. 6,254,573 (Patent Reference 3), U.S. Pat. No. 6,309,370 (corresponding to Japanese Patent Laid-open No. 2001-87392) (Patent Reference 4), U.S. Pat. No. 5,972,013 (Patent Reference 5), U.S. Pat. No. 6,592,552 (corresponding to Japanese Unexamined Patent Publication No. 2001-516625) (Patent Reference 6), U.S. Pat. No. 5,931,810 (Patent Reference 7) and U.S. Pat. No. 6,102,887 (Patent Reference 8), for example.

Patent Reference 1 and Patent Reference 2 disclose catheters which are provided with a spiral injection needle. Patent Reference 3 and Patent Reference 4 disclose catheters which are provided at the distal end portions thereof with a contact-type sensor composed of a pressure sensor.

Patent Reference 5 and Patent Reference 6 disclose catheters which include a mechanism for creating a negative pressure in a catheter and consequently fixing the distal end portion of the catheter to a relevant tissue by virtue of suction. Patent Reference 7 discloses a puncturing device which is adapted to take hold of a relevant tissue mechanically, fix the distal end portion thereof to the tissue, and form a puncture aimed at.

Patent Reference 8 discloses a catheter which is provided with an injection needle held in the distal end portion thereof and a fixing device capable of radially opening from the distal end portion outwardly. Patent Reference 8 incidentally discloses a fixing device pointed in the leading terminal and a fixing device not pointed in the leading terminal both.

The spiral needle involved in Patent Reference 1 and Patent Reference 2 is such that, during the injection of a therapeutic composition, it is prevented from slipping out of the tissue and enabled to effect infallible injection. It is, however, not easily drawn out in the direction of extraction. While the spiral needle is stuck in a feeble cardiac muscle in the state of infarction, for example, an erroneous motion produced by the distal end portion of the catheter will possibly cause the spiral needle to tear off the cardiac tissue.

The contact-type sensor involved in Patent Reference 3 and Patent Reference 4 is disposed on the terminal face of the distal end portion of the catheter and, therefore, is required to contact the cardiac tissue without fail. Since the interior of the heart has a heavily irregular surface, the contact-type sensor tends to incur an error and entails the problem of lacking precision.

The catheter involved in Patent Reference 5 and Patent Reference 6 is aimed at being used in a flat region which is not filled with such humor as the blood. If it is applied to the surface of a tissue which is filled with the humor and is not invariably flat, therefore, it will incur difficulty in enabling the distal end portion of the catheter to contact perfectly closely to the surface of the tissue and will entail the possibility of aspirating the humor.

The puncturing device involved in Patent Reference 7 is directed toward taking hold of the heart sac which possesses comparatively appreciable strength. If it is applied to such a feeble tissue as the tissue of cardiac muscle in the state of infarction, for example, it will possibly rip off the tissue.

The fixing device with a pointed leading terminal which is involved in Patent Reference 8 is capable of keeping the catheter fixed to a tissue during the puncturing of the tissue and the injection of a therapeutic composition therein. It is, however, expanded radially after it has been stuck into the tissue aimed at. It, therefore, carries out a very large invasion on the peripheral part of the issue aimed at. The fixing device with no pointed leading terminal which is involved in Patent Reference 8 incurs extreme difficulty in inducing the catheter to operate and fails to fix the catheter at an arbitrary region in the heart because it fixes the catheter to the tissue by widening the columnar carneae in the heart.

SUMMARY OF THE INVENTION

The present invention has been made in order to solve the above-mentioned problems in the prior art. Accordingly, it is a general object of the present invention to provide catheter which substantially represses the possible infliction of invasion and infallibly accomplishes the puncture of a target issue with an injection needle and the injection of a therapeutic composition thereto.

More specifically, it is an object of the invention to provide a catheter for percutaneous intracavitary insertion including a sheath portion, an insertion member, an injection needle, and paired electrodes. The sheath portion has a lumen extending therein. The insertion member is disposed slidably in the lumen of the sheath portion and provided with a distal end portion capable of protruding from a distal end portion of the sheath portion. The injection needle is disposed in the distal end portion of the insertion member for injecting a therapeutic composition to a target tissue. The paired electrodes are disposed in a distal end portion of the catheter for measuring impedance.

It is another specific object of the invention to provide a catheter system including a catheter for percutaneous insertion, paired electrodes, and a puncture detecting device. The catheter includes a sheath portion with a lumen extending therein, an insertion member disposed slidably in the lumen of the sheath portion and provided with a distal end portion capable of protruding from a distal end portion of the sheath portion, and an injection needle disposed in the distal end portion of the insertion member for injecting a therapeutic composition to a target tissue. The paired electrodes are disposed in a distal end portion of the catheter for measuring impedance. Conductors extending from the paired electrodes are able to be connected to the puncture detecting device for detecting a puncture by the injection needle based on impedance values measured by the paired electrodes.

It is a further specific object of the invention to provide a method for injecting a therapeutic composition with a catheter including a sheath portion with a lumen extending therein, an insertion member disposed slidably in the lumen of the sheath portion and provided with a distal end portion capable of protruding from a distal end portion of the sheath portion, an injection needle disposed in the distal end portion of the insertion member for injecting a therapeutic composition to a target tissue, and paired electrodes disposed in a distal end portion of the catheter for measuring impedance. The method includes the steps of (a) inserting the catheter into a living body and advancing it to a neighborhood of the target tissue, and (b) puncturing the target tissue with the injection needle based on impedance values measured by the paired electrodes and injecting the therapeutic composition into the target tissue through the injection needle.

The objects, features, and characteristics of this invention other than those set forth above will become apparent from the description given herein below with reference to preferred embodiments illustrated in the accompanying drawings.

BRIEF DESCRIPTION OF THE DRAWINGS

FIG. 1 is a schematic view of a catheter according to Embodiment 1 of this invention.

FIG. 2 is a sectional view for illustrating an operating unit shown in FIG. 1.

FIG. 3 is a sectional view for illustrating the distal end portion of the catheter shown in FIG. 1, depicting the state thereof having an injection needle protruded out.

FIG. 4 is a sectional view for illustrating the distal end portion of the catheter shown in FIG. 1, depicting the state thereof having the injection needle retracted to the home position.

FIG. 5 is a side view of the distal end portion of an insertion member shown in FIG. 1.

FIG. 6 is a schematic view for illustrating a catheter system to which the catheter shown in. FIG. 1 is applied.

FIG. 7 is a side view for illustrating a modified version of the catheter according to Embodiment 1, depicting the distal end portion of the insertion member.

FIG. 8 is a schematic view for illustrating another modified version of the catheter according to Embodiment 1, depicting the distal end portion of the insertion member.

FIG. 9 is a sectional view for illustrating a catheter according to Embodiment 2.

DETAILED DESCRIPTION OF THE PREFERRED EMBODIMENT

Figure 6:
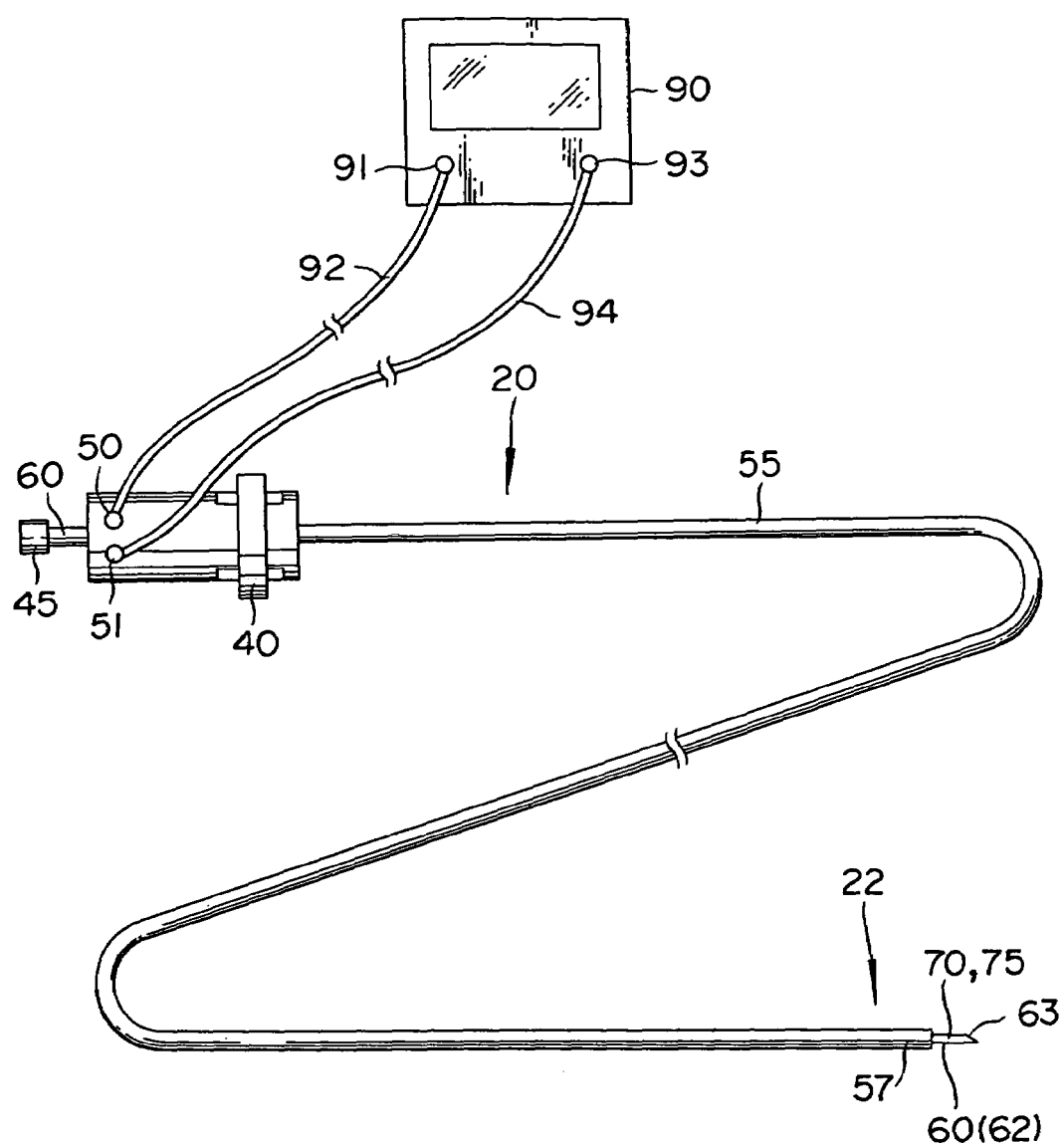

The embodiments of this invention will be described below with reference to the accompanying drawings.

FIG. 1 is a schematic view of a catheter according to Embodiment 1. A catheter 20 includes an operating unit 30, a sheath portion 55, an injection needle 63 disposed at a distal end portion 62 of an insertion member 60, and electrodes 70, 75 disposed at a distal end portion 22 of the catheter 20 and is used as percutaneously inserted into an inner space of a living body. The electrodes 70, 75 are composed of paired electrodes which serve the purpose of measuring impedance and function as a puncture sensor.

The operating unit 30 is positioned at a proximal end portion 21 of the catheter 20, and the distal end portion 62 of the insertion member 60 and the injection needle 63 are positioned at the distal end portion 22 of the catheter 20.

The sheath portion 55 includes a lumen extending in the interior thereof and enabled to extend the insertion member 60 slidably therein. Though the sheath portion 55 does not need to have a particularly restricted shape, it is preferred to have a cylindrical shape. The outside diameter of the sheath portion 55 does not need to be particularly limited. It is preferred nevertheless to be not more than 10 frenches (3.3 mm).

The material for the sheath portion 55 does not need to be particularly limited. Such polymer materials as polyolefins, olefin type elastomers, polyesters, soft polyvinylchloride, polyurethanes, urethanetypeelastomers, polyamides, amide type elastomers, polytetrafluoroethylene, fluorine resin elastomers, polyimides, ethylene-vinyl acetate copolymers, and silicone rubbers are usable.

Polyolefins are polypropylene and polyethylene, for example. Olefin type elastomers are polyethylene elastomer and polypropylene elastomer, for example, Amide type elastomers include polyamide elastomer, for example.

When the sheath portion 55 is formed from a synthetic resin, a pipe of a super-elastic alloy or an embedded coil or embedded mesh made of a metal may be utilized for enhancing the rigidity of the sheath portion 55.

A distal end portion 57 of the sheath portion 55 is preferred to possess the function of an x-ray contrast marker. It may be formed by using a resin containing a radiopaque material, for example. As concrete examples of the radiopaque material, tantalum, tungsten carbide, bismuth oxide, barium sulfate, platinum or alloys thereof, and cobalt alloys which are available in a powdered form may be cited.

The insertion member 60 is slidably disposed in the lumen of the sheath portion 55. Though the insertion member 60 does not need to have a particularly restricted shape, it is preferred to have a cylindrical shape. The outside diameter of the insertion member 60 does not need to be particularly limited but is only required to be such that the insertion member 60 may slide inside the lumen of the sheath portion 55. It properly falls in the range of 0.3-1.0 mm. The inside diameter of the insertion member 60 is preferred to fall in the range of 0.15-0.8 mm.

The material for the insertion member 60 does not need to be particularly restricted. Such metals as stainless steel, Ni—Ti alloy, Cu—Zn alloy, cobalt alloy, and tantalum and such polymer materials as polyamide, polyimide, ultra-high molecular weight polyethylene, polypropylene, and fluorine resin are available. These materials may be used either singly or in the form of a combination of two or more members.

The injection needle 63 is used for the purpose of injecting a therapeutic composition to a target tissue. The target tissue is a diseased part in the living body such as the region of a cardiac ischemia or the cardiac tissue in the peripheral part thereof. The injection needle 63 can be constructed, for example, by subjecting the distal end portion 62 of the insertion member 60 to a needle-forming processing to form a bevel (cutting edge surface), or by mounting and fixing a separate injection needle to the distal end portion 62 of the insertion member 60.

FIG. 2 is a sectional view for illustrating the operating unit shown in FIG. 1. FIG. 3 and FIG. 4 are sectional views for illustrating the distal end portion of the catheter shown in FIG. 1. FIG. 5 is a side view of the distal end portion of the insertion member shown in FIG. 1. Incidentally, FIG. 3 depicts the state of the catheter having the injection needle protruded out, and FIG. 4 depicts the catheter having the injection needle retracted to the home position.

The operating unit 30 positioned at the proximal end portion 21 of the catheter 20 includes a housing 31 with a slit 33 formed therein, output terminals 50, 51 adapted to be connected to an external impedance analyzer (device for detecting a puncture), and a hub 45.

The output terminals 50, 51 are connected to the electrodes 70, 75 through wires 80, 85 extending along the insertion member 60. The hub 45 is a connector for injecting the therapeutic composition. It allows a syringe to be connected thereto.

A proximal end portion 56 of the sheath portion 55 is fixed to the housing 31 and a proximal end portion 61 of the insertion member 60 is introduced into the interior of the housing 31 and connected to the hub 45. On the inner peripheral surface of the housing 31, a drive unit 32 formed of an elastic material is slidably disposed as closely attached thereto.

The drive unit 32 includes a central part for fixing by adhesion thereto the insertion member 60 which passes through the drive unit 32, and an outer peripheral part for fixing a needle controller 40. The needle controller 40 is slidably inserted inside the slit 33 formed in the housing 31.

The insertion member 60, therefore, is driven by operating the needle controller 40 and setting the drive unit 32 into motion. As a result, the injection needle 63 disposed at the distal end portion 62 of the insertion member 60 is protruded out of the distal end portion 57 of the sheath portion 55 (refer to FIG. 3) or retracted to the home position in the distal end portion 57 of the sheath portion 55 (refer to FIG. 4).

The drive unit 32 can be stopped at an arbitrary position of the slit 33 because it is formed of an elastic material and is disposed as held in close contact with the inner peripheral surface of the housing 31. In the inner peripheral surface of the housing 31, a stopper 35 is provided for accurately restricting the distance of motion of the drive unit 32.

An O ring 34 is disposed in the gap between the outer peripheral surface of the insertion member 60 and the inner peripheral surface of the proximal end portion 56 to seal the interior of the operating unit 30 and prevent inflow of blood, for example.

The distal end portion 57 of the sheath portion 55 positioned at the distal end portion 22 of the catheter 20 is provided with a through-hole 58 communicating with the lumen of the sheath portion 55. The through-hole 58 enhances the flow of the blood in and out of the sheath portion 55 and ensures the entry of the blood to the distal end portion 22 of the catheter 20. The through-hole 58 is preferred to be separated by not less than 1 mm from the end face of the distal end portion 57 of the sheath portion 55 relative to the longitudinal direction of the sheath portion 55.

The electrodes 70, 75 are approximately rectangular and are disposed at the distal end portion 62 of the insertion member 60 in the neighborhood of a bevel 63A of the injection needle 63. The electrodes 70, 75 occupy one and the same position relative to the longitudinal direction of the insertion member 60 and occupy different positions relative to the circumferential direction of the insertion member 60.

The impedance values which are measured by the electrodes 70, 75 show a large discernible difference when the electrodes 70, 75 exist in the blood and when they exist inside the tissue of the heart. The impedance values vary with the region selected for the puncture with the injection needle 63 and the frequency used for the measurement. The impedance value in the blood, for example, falls in the approximate range of 40-60% of the impedance values in the tissue of the heart. The puncture with the injection needle 63, therefore, can be detected on the basis of the impedance values measured by the electrodes 70, 75.

The electrodes 70, 75 are preferred to be disposed as separated by not less than 1 mm and not more than 3 mm from the leading terminal of the bevel 63A of the injection needle 63 relative to the longitudinal (extending) direction of the insertion member 60. When a change is detected in the impedance values at this position of disposition, this fact indicates that the injection needle 63 is certainly present in the tissue of the heart.

The insertion member 60 has the outer peripheral surface thereof excluding the bevel 63A of the injection needle 63 covered with an electrical insulator 64. The electrical insulator 64 is made of an electrically insulating material such as polyimide varnish or polyurethane resin or fluorine resin. In FIG. 2, the electrical insulator 64 is not shown to simplify drawing.

The shapes of the electrodes 70, 75 do not need to be particularly limited. The method of disposing the electrodes 70, 75 does not need to be particularly restricted. It is permissible to form them by adhesion of conductors or vacuum evaporation or plating of conductors.

To the electrodes 70 and 75, the wires 80, 85 extending from the output terminals 50, 51 which are disposed in the operating unit 30 are connected. The wires 80, 85 include conductors 81, 86 with terminals connected to the electrodes 70, 75 and electrical insulators 82, 87 covering the conductors 81, 86. The conductors 81, 86 and the electrical insulators 82, 87 are fixed by adhesion as to the electrical insulator 64 covering the outer periphery of the insertion member 60.

That is, the electrodes 70, 75 are connected to the conductors 81, 86 covered with the electrical insulators 82, 87 and the conductors 81, 86 extend to the proximal end portion 21 of the catheter 20. Though the materials for the electrodes 70, 75 and the conductors 81, 86 do not need to be particularly restricted, they are preferred to be selected from among gold, platinum, platinum iridium, tungsten, and silver, for example.

When the insertion member 60 and the injection needle 63 are separate members, the work of attaching the injection needle 63 is carried out after the outer peripheral surface of the insertion member 60 has been covered with the electrical insulator 64 and the electrodes 70, 75 and the wires 80, 85 have been disposed. In this case, the work of covering with the insulator 64 is simplified because the covering of the electrical insulator 64 does not need to avoid the bevel 63 of the injection needle 63. When the insertion member 60 is formed of such an electrically insulating material as a plastic, the coating with the electrical insulator 64 is no longer necessary.

FIG. 6 is a schematic view for illustrating a catheter system 10 to which the catheter 20 shown in FIG. 1 is applied. The catheter system 10 includes the catheter 20 and an impedance analyzer 90.

The impedance analyzer 90 is provided with input terminals 91 and 93, connected to the output terminals 50, 51 of the operating unit 30 through cords 92 and 94, and thus connected to the electrodes 70, 75 disposed at the distal end portion 62 of the insertion member 60 through the wires 80, 85.

The impedance analyzer 90 detects the puncture with the injection needle 63 on the basis of a change in the impedance values measured by the electrodes 70, 75. Though the frequency applied to this measurement does not need to be particularly restricted, it is preferred to fall in the range of 50-200 kHz.

Now, a method of using the catheter system 10 relative to the case of the tissue of the heart as the target region will be described below.

First, the operator, by using a guiding catheter under X-ray fluoroscopy, for example, inserts the catheter 20 into the living body and guides the distal end portion 22 of the catheter 20 into the ventricle positioned in the neighborhood of a target tissue.

Then, the operator pushes the distal end portion 57 of the sheath portion 55 against the cardiac wall to supply the alternating current from the impedance analyzer 90 between the electrodes 70, 75 and, while checking the impedance values measured by the electrodes 70, 75, operates the needle controller 40. As a result, the insertion member 60 is moved toward the leading terminal relative to the sheath portion 55 and the injection needle 63 is protruded from the distal end portion 57 of the sheath portion 55 and punctures the tissue of the cardiac muscle.

Since the puncture of the cardiac tissue by the injection needle 63 causes the electrodes 70, 75 to move from within the blood into the cardiac tissue, the impedance values measured by the electrodes 70, 75 produce a large change. By this change, the puncture by the injection needle 63 is confirmed. Since the flow of blood in and out of the sheath portion 55 is enhanced owing to the presence of the through-hole 58 formed in the distal end portion 57 of the sheath portion 55, it is made possible to ensure the inflow of blood and permit more accurate measurement of the impedance when the electrodes 70, 75 are present in the blood.

Subsequently, the syringe connected to the hub 45, for example, is utilized to inject a therapeutic composition into the cardiac muscle via the injection needle 63. In this case, the absence of a noticeable change in the impedance values measured by the electrodes 70, 75 is required to be confirmed. In consequence of this conformation, it is ascertained that the reaction of the work of injecting the therapeutic composition has not induced the injection needle 63 to slip off the target tissue.

After the injection is completed, the injection needle 63 is retracted to home position in the distal end portion 57 of the sheath portion 55 and the distal end portion 22 of the catheter 20 is moved to the next target region by manipulating the needle operating unit 40. The operation described thus far is repeated.

In Embodiment 1 according to this invention, the injection needle 63 is enabled to puncture the target tissue infallibly and the therapeutic composition to be injected into the target tissue without fail on the basis of the impedance values measured by the electrodes 70, 75. Embodiment 1 also enjoys repression of the possibility of invasion because it has no need for any special device for the purpose of fixing the catheter to the tissue.

FIG. 7 is a side view for illustrating an example of the modification of the catheter according to Embodiment 1, depicting the distal end portion of the insertion member.

The electrodes 70, 75 which are used for measuring the impedance do not need to be invariably disposed at one and the same position (refer to FIG. 5) but may be disposed at different positions relative to the longitudinal direction of the insertion member 60.

In the construction of this sort, the impedance values measured by the electrodes 70, 75 show a discernible difference when one of the electrodes 70, 75 (electrode 70) exists in the cardiac tissue and the remainder of the electrodes 70, 75 (electrode 75) exists in the blood, when both the electrodes 70, 75 are present in the blood, and when both the electrodes 70, 75 are present in the cardiac tissue.

The impedance values in the blood, for example, are approximately in the range of 70-80% of the impedance values in the coexistence in the blood and in the cardiac tissue. By the way, the impedance values in the blood are approximately in the range of 40-60% of the impedance values in the cardiac tissue as described above.

Thus, the detection of the puncture with the injection needle 63 and the detection of the depth of the puncture can be attained on the basis of the impedance values measured by the electrodes 70, 75. That is, in the present example of the modification, the puncture with the injection needle 63 is attained with more certainty because the detection of the depth of the injection needle 63 is achieved in addition to the detection of the puncture with the injection needle 63. Further, the present example of the modification is particularly suitable for the therapy which, for the sake of manifesting the effect thereof, requires the injection needle 63 to perform the puncture accurately at the target depth in the diseased part.

Both the electrodes 70, 75 or the electrode 70 on the distal side is preferred to be disposed as separated by not less than 1 mm and not more than 3 mm from the leading end of the bevel 63A of the injection needle 63 relative to the longitudinal direction of the insertion member 60. The detection of a change in the impedance at this configuration indicates with certainty the presence of the injection needle 63 in the cardiac tissue.

The distance of separation between the electrode 70 and the electrode 75 relative to the longitudinal direction of the insertion member 60 does not need to be particularly restricted. This distance of separation, however, is preferably not more than 5 mm and more preferably not more than 2.5 mm because an undue addition to this distance of separation possibly prevents the impedance values measured by the electrodes 70, 75 from showing a conspicuous change.

FIG. 8 is a schematic view for illustrating another example of the modification of the catheter according to Embodiment 1, depicting the distal end portion of the insertion member. In the present example of the modification, the paired electrodes for measuring the impedance exist in a plurality of sets. These sets are positioned as separated relative to the longitudinal direction of the insertion member. A plurality of impedance analyzers are installed in conformity with the number of sets of paired electrodes.

To be more specific, electrodes 170, 175 composed of the second set of paired electrodes are disposed at a position separated from the electrodes 70, 75 composed of the first set of paired electrodes. The electrodes 170, 175 occupy one and the same position relative to the longitudinal direction of the insertion member 60 and occupy different positions relative to the circumferential direction of the insertion member 60. The electrodes 170, 175 are connected to input terminals 191, 193 of an impedance analyzer 190.

Incidentally, the number of output terminals of the catheter 20 to be installed corresponds to the number of electrodes 70, 75, 170, and 175 installed.

In the present example of the modification, therefore, the electrodes 70, 75 and the electrodes 170, 175 sequentially come into contact with the cardiac tissue and produce changes in the impedance values to be measured in proportion as the depth of the injection needle 63 increases. Thus, this example enjoys an improvement in the accuracy of the detection of the depth of the injection needle 63 as compared with the example of the modification of FIG. 7. Then, at least one of the electrodes 70, 75, 170, and 175 which are included in the plurality of sets of paired electrodes is preferred to be separated by not less than 1 mm from the leading end of the bevel 63A of the injection needle 63.

Figure 10:
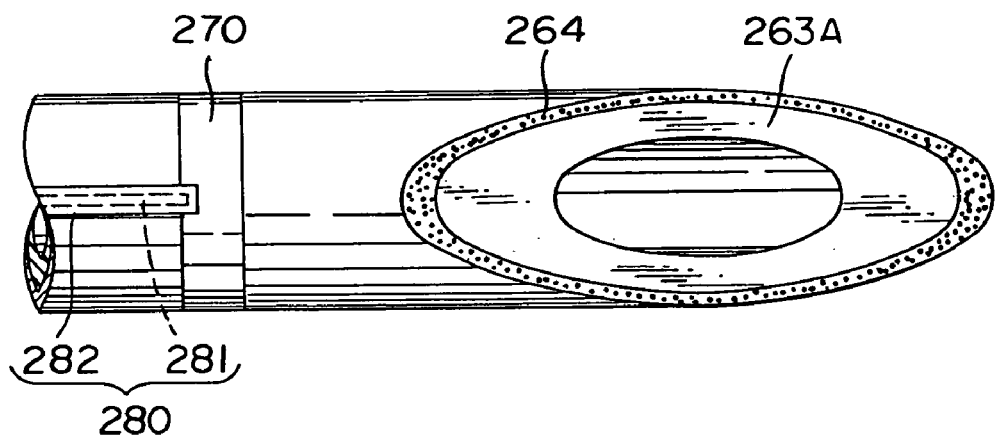
FIG. 10 is a side view for illustrating the distal end portion of the insertion member shown in FIG. 9.
Figure 11:
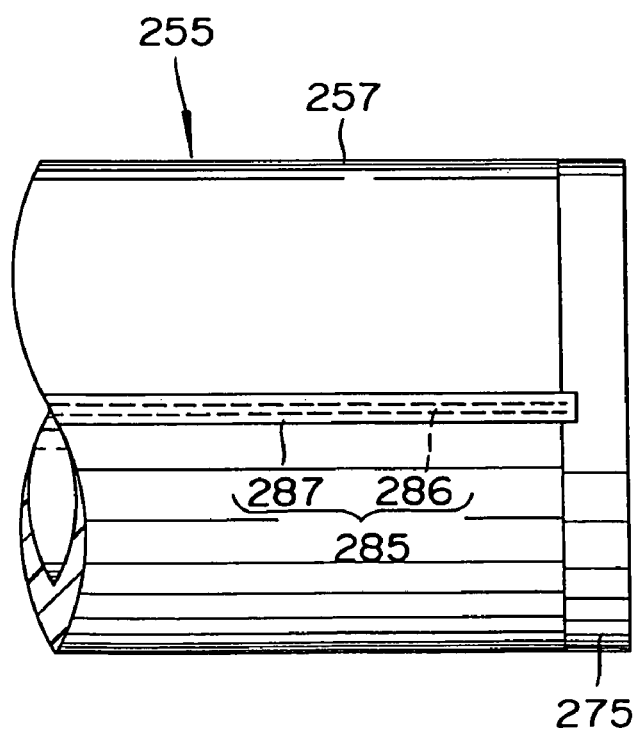
FIG. 11 is a side view for illustrating the distal end portion of a sheath portion shown in FIG. 9.

FIG. 9 is a sectional view for illustrating the catheter according to Embodiment 2, FIG. 10 is a side view for illustrating the distal end portion of the insertion member shown in FIG. 9, and FIG. 11 is a side view for illustrating the distal end portion of the sheath portion shown in FIG. 9.

Embodiment 2 has one of the paired electrodes positioned at the distal end portion of the insertion member and the remaining electrode positioned at the distal end portion of the sheath portion. In this respect, Embodiment 2 differs from Embodiment 1 which has both the paired electrodes positioned at the distal end portion of the insertion member.

An electrode 270, or one of the paired electrodes, is in an annular shape. A distal end portion 262 of an insertion member 260 has the outer peripheral surface thereof excluding a bevel 263A of an injection needle 263 covered with an electrical insulator 264. The electrode 270 is fixed by caulking to the distal end portion 262 of the insertion member 260.

To the electrode 270, a wire 280 extending from the output terminal disposed in the operating unit is connected. The wire 280 includes a conductor 281 with a terminal connected to the electrode 270 and an electrical insulator 282 covering the conductor 281. The conductor 281 extends to the proximal end portion of the catheter.

The conductor 281 and the electrical insulator 282 are fixed by adhesion, for example, to the electrical insulator 264 covering the outer periphery of the insertion member 260. The wire 280 is introduced along the insertion member 260 into the housing of the operating unit and passed through the drive unit.

An electrode 275, or the remainder of the paired electrodes, also has an annular shape and is fixed by caulking, for example, to a distal end portion 257 of a sheath portion 255. To this electrode 275, a wire 285 extending from the output terminal disposed in the operating unit is connected. The wire 285 includes a conductor 286 with a terminal connected to the electrode 275 and an electrical insulator 287 covering the conductor 286.

The wire 285 is advanced at the proximal end portion of the sheath portion 255, for example, through the gap between the outer periphery of the proximal end portion of the insertion member 260 and the inner peripheral surface of the proximal end portion of the sheath portion 255, introduced into the housing of the operating unit, and passed through the drive unit.

The wires 280 and 285, similarly to Embodiment 1, extend to the proximal end portion of the catheter and connected to the output terminals of the catheter. The output terminals mentioned above are connected with cords to the input terminals of the impedance analyzer.

Now, the method of using the catheter according to Embodiment 2 will be described.

First, the operator, by using a guiding catheter under X-ray fluoroscopy, for example, inserts the catheter into the living body and guides the distal end portion of the catheter into the ventricle positioned in the neighborhood of a target tissue.

Then, the operator pushes a distal end portion 257 of the sheath portion 255 against the cardiac wall and, while confirming the impedance values measured by the electrodes 270, 275, operates the needle controller 40. As a result, the insertion member 260 is moved toward the distal side relative to the sheath portion 255 and the injection needle 263 is protruded from the distal end portion 257 of the sheath portion 255 and punctures the tissue of the cardiac muscle.

Since the puncture of the cardiac tissue by the injection needle 263 causes the electrodes 270 to move from within the blood into the cardiac tissue, the impedance values measured by the electrodes 270, 275 produce a large change. By this change, the puncture by the injection needle 263 is confirmed.

Subsequently, the syringe connected to the hub, for example, is utilized to inject a therapeutic composition into the cardiac muscle via the injection needle 263. In this case, the absence of a noticeable change in the impedance values measured by the electrodes 270, 275 is required to be confirmed. In consequence of this conformation, it is ascertained that the reaction of the work of injecting the therapeutic composition has not induced the injection needle 263 to slip off the target tissue.

After the injection is completed, the injection needle 263 is retracted to home position in the distal end portion 257 of the sheath portion 255 and the distal end portion of the catheter is moved to the next target region. The operation described thus far is repeated.

Even by the catheter according to Embodiment 2, the injection needle 263 is enabled to puncture the target tissue without fail and inject the therapeutic composition into the target tissue with certainty on the basis of the impedance values measured by the electrodes 270, 275.

Figure 12:
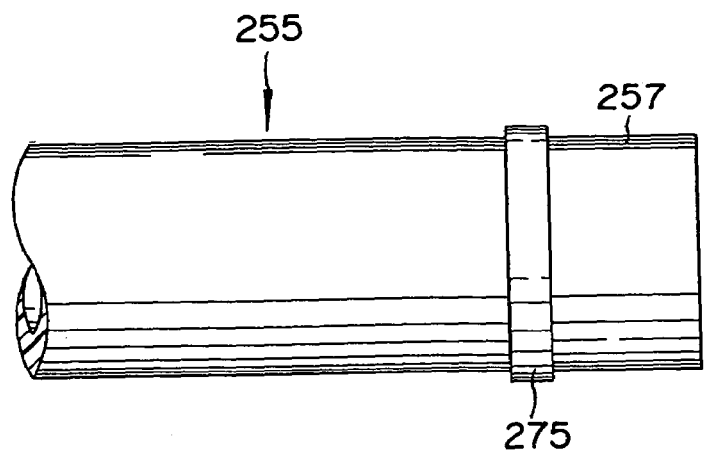
FIG. 12 is a side view for illustrating a modified version of the catheter according to Embodiment 2, depicting the distal end portion of the sheath portion.
Figure 13:
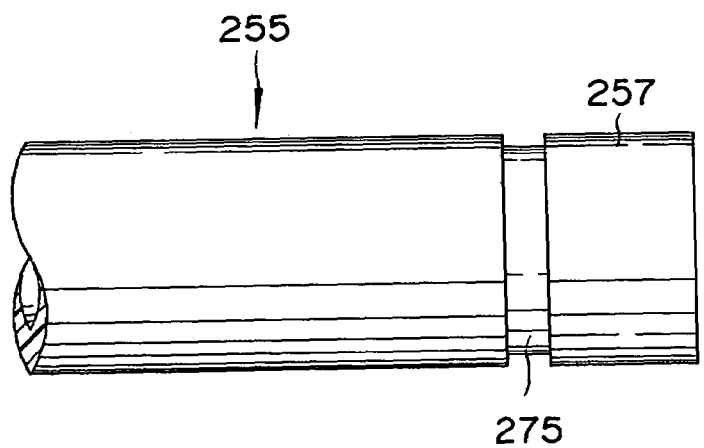
FIG. 13 is a side view for illustrating another modified version of the catheter according to Embodiment 2, depicting the distal end portion of the sheath portion.
Figure 14:
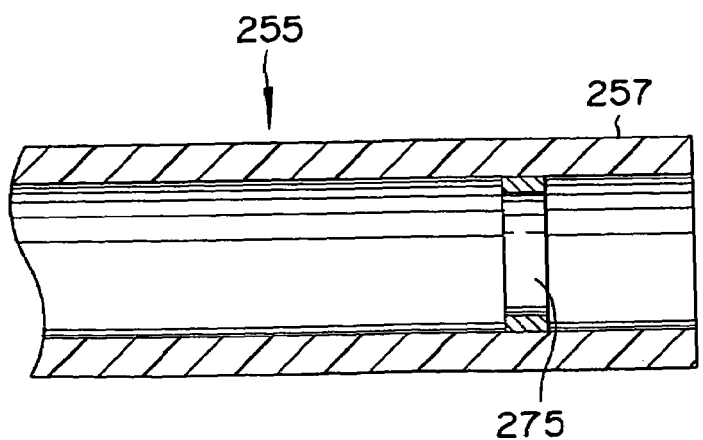
FIG. 14 is sectional view for illustrating yet another modified version of the catheter according to Embodiment 2, depicting the distal end portion of the sheath portion.

FIGS. 12-14 depict examples of the modification of the catheter according to Embodiment 2, respectively. FIG. 12 and FIG. 13 are side views of the distal end portion of the sheath portion and FIG. 14 is a sectional view of the distal end portion of the sheath portion.

The electrode 275 may be disposed on the proximal side as separated from the end face of the distal end portion 257 of the sheath portion 255 (refer to FIG. 12).

It is also permissible to have the electrode 275 embedded in the distal end portion 257 of the sheath portion 255 (refer to FIG. 13). This modification may be accomplished, for example, by forming a recess along the circumferential direction in the distal end portion 257 of the sheath portion 255, mounting the electrode 275 by caulking in the recess, connecting the conductor extending from the proximal end portion to the electrode 257, and then covering the surface of the conductor with an electrical insulator.

It is further permissible to have the electrode 275 disposed in the lumen of the sheath portion 255 and fixing it therein (refer to FIG. 14). This configuration can be accomplished, for example, by inserting the electrode 275 having a slightly smaller outside diameter than the inside diameter of the lumen of the sheath portion 255 through the distal end portion of the sheath portion 255 into the lumen and fixing by adhesion the electrode 275 at a position advanced by several mm from the distal end portion of the sheath portion 255 relative to the longitudinal direction of the sheath portion 255.

When the electrode 275 is embedded or disposed inside the lumen, the possibility of the electrode 275 erroneously contacting the irregularities of the surface of the ventricle and consequently inducing erroneous detection can be repressed.

Figure 15:
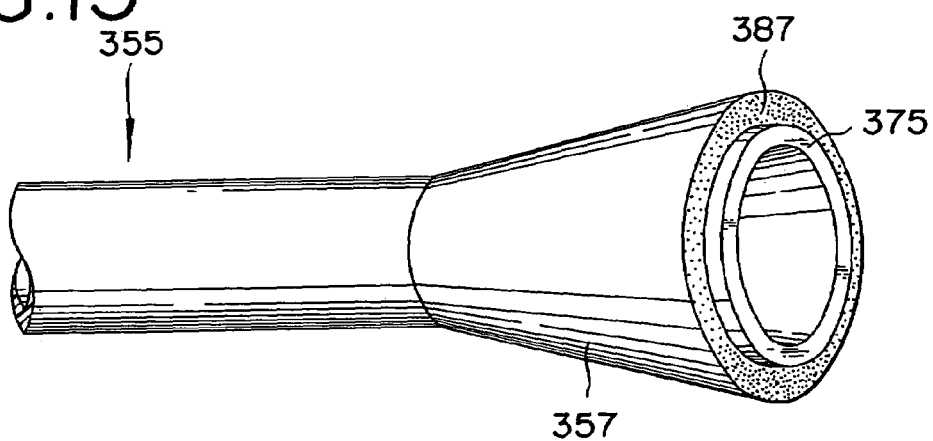
FIG. 15 is a side view for illustrating one example of the method of production for disposing an electrode at the distal end portion of the sheath portion.
Figure 16:
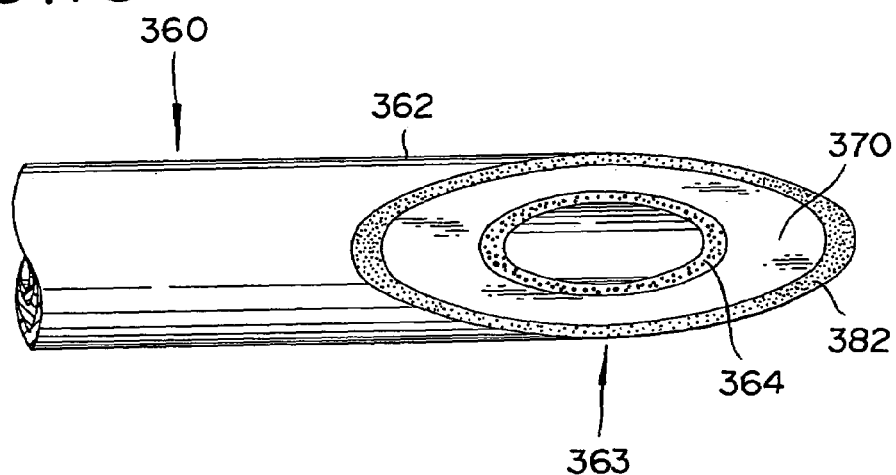
FIG. 16 is a side view for illustrating one example of the method of production for disposing an electrode at the distal end portion of the insertion member.
Figure 17:
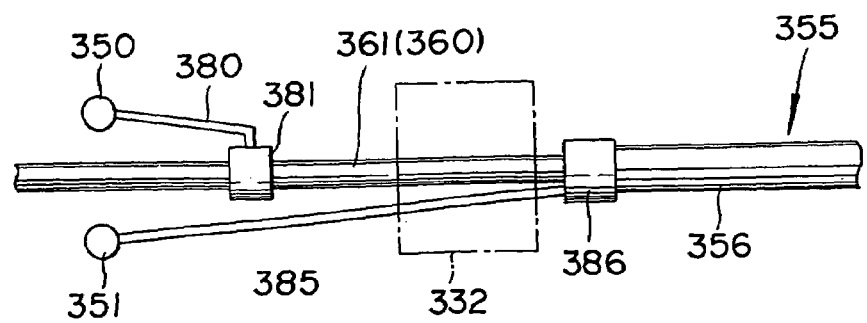
FIG. 17 is a schematic view for illustrating the structure of a proximal end portion of the sheath portion shown in FIG. 15 and the structure of the proximal end portion of the insertion member shown in FIG. 16.

FIG. 15 is a side view for illustrating one example of the method of production for disposing the electrode at the distal end portion of the sheath portion, FIG. 16 is a side view for illustrating one example of the method of production for disposing the electrode at the distal end portion of the insertion member, and FIG. 17 is a schematic view for illustrating the construction of the proximal end portion of the sheath portion shown in FIG. 15 and the proximal end portion of the insertion member shown in FIG. 16.

A sheath portion 355 is formed of a polyimide tube (produced by Micro Lumen Inc.) with braided wires containing tungsten carbide which functions as an x-ray contrast marker. The polyimide tube has a three-layer construction having braided wires interposed in the manner of a sandwich between inner and outer polyimide layers and measures 1300 mm in length, 1.0 mm in outside diameter, and 0.9 mm in inside diameter.

The braided wires are exposed by treating one end (the distal end portion) of the polyimide tube 355 with a laser beam and peeling only the polyimide layer on the outer peripheral surface about 2 mm in thickness.

Then, a front cap 357 is attached to the distal end portion of the polyimide tube 355. The front cap 357 is formed of an electroconductive material (SUS304) in the shape of a circular truncated cone. The front cap 357 has the outer circular surface thereof excluding the outer peripheral part near the end face coated with an electrical insulator 387. The inner peripheral surface of the front cap 357 is not given any insulating coat in order that this surface may contact the braided wires exposed in the polyimide tube 355 and permit flow of an electric current.

The leading end of the front cap 357 has an outside diameter of 1.8 mm and the part thereof attached to the polyimide tube 355 has an outside diameter of 1.2 mm and a length of 3 mm. An electrode 375 forming one of paired electrodes which are used for measuring the impedance is an annular portion made of an electroconductive material as exposed near the end face of the front cap 357.

The other end of the polyimide tube 355 is treated with a laser beam so that the braided wires are exposed by peeling only the polyimide layer on the outermost peripheral surface. Then, a connector 386 is attached to the part of the other end (proximal end portion) 356 of the polyimide tube 355 exposing the braided wires as illustrated in FIG. 17.

To the connector 386, a wire 385 extending from an output terminal 351 disposed in the operating unit is connected. Incidentally, in the connector 381, braided wires are connected to the conductor of the wire 385. The wire 385 extends through a through-hole formed in a drive unit 332.

An insertion member 360 is formed by coating the inner peripheral surface and the outer peripheral surface of a hollow steel pipe (made by Oba Kiko K.K.) with a polyimide varnish (electrical insulator). The insertion member 360 is made of SUS304 and measures 1500 mm in length, 0.7 mm in outside diameter, and 0.5 mm in inside diameter.

A distal end portion 362 of the insertion member 360 is ground to form a bevel 370 destined to form a blade face as illustrated in FIG. 16. In this case, the annular portion resulting from peeling an insulating coat formed of polyimide (the annular portion intervening between an electrical insulator 364 and an electrical insulator 382) serves as an electrode for forming the remainder of the paired electrodes which measure the impedance.

A proximal end portion 361 of the insertion member 360 is enabled to expose the steel pipe of SUS304 by peeling only the polyimide layer on the outermost peripheral surface at a proper position past the drive unit 332. Then, connector 381 is connected to the part exposing the steel pipe of SUS304 as illustrated in FIG. 17. A wire 380 extending from an output terminal 350 is connected to the connector 381. Incidentally, at the connector 381, the steel pipe of SUS304 is connected to the conductor of the wire 380.

Accordingly, one of the paired electrodes can be disposed at the distal end portion of the insertion member and the remainder of the paired electrodes disposed at the distal end portion of the sheath portion as described above.

Figure 18:
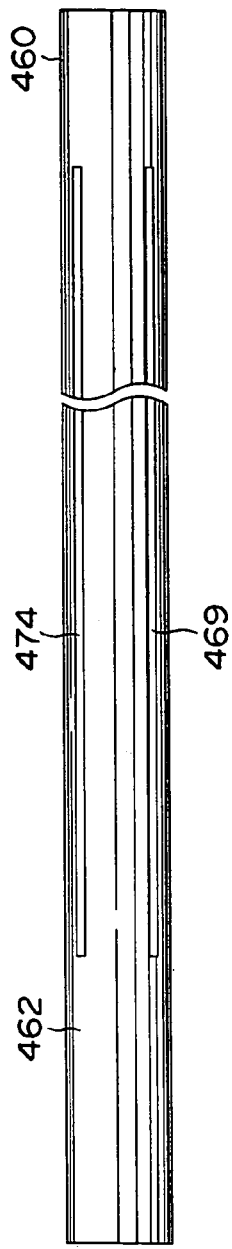
FIG. 18 is a side view for illustrating one example of the method of production for disposing a pair of electrodes in the distal end portion of the insertion member.
Figure 19:
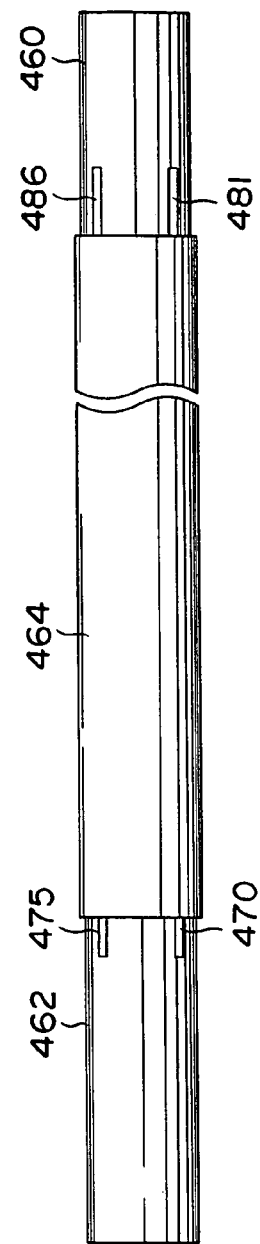
FIG. 19 is a side view for illustrating a step which continues from the step shown in FIG. 18.

FIG. 18 is a side view for illustrating one example of the method of production for disposing the paired electrodes at the distal end portion of the insertion member. FIG. 19 is a side view for illustrating a step continuing from the step of FIG. 18. FIG. 19 is a side view for illustrating a step continuing from the step of FIG. 19.

An insertion member 460 is formed by coating the outer peripheral surface of a hollow steel pipe (made by Oba Kiko K.K.) with a polyurethane resin (electrical insulator). The hollow steel pipe made of SUS304 measures 1500 mm in length, 0.7 mm in outside diameter, and 0.5 mm in inside diameter.

Then, the coating layer on the outer peripheral surface of the insertion member 460 is given a surface treatment by reverse sputtering using a sputtering device. Subsequently, a mask with two parallel openings having a rectangular cross section is disposed along the longitudinal direction of the insertion member 460. Gold is deposited on the insertion member 460 by projecting it toward the mask by the use of a vacuum evaporation device.

After the removal of the mask, electric conductors (gold layers resulting from the vacuum evaporation) 469, 474 formed where the openings of the mask were disposed are plated with gold by the electrolytic plating method to increase in thickness (refer to FIG. 18).

Then, by applying a polyimide varnish (electrical insulator) 464 to the central parts of the electric conductors 469, 474 except for the opposite ends thereof, electrodes 470, 475 and conductors 481 and 486 for measuring the impedance are formed (refer to FIG. 19). In short, the distal end portions of the electric conductors 469, 474 form electrodes 470, 475 and the proximal end portions of the electric conductors 469, 474 form terminals for connection to conductors of the wire which is connected to the output terminal of the catheter.

Figure 20:
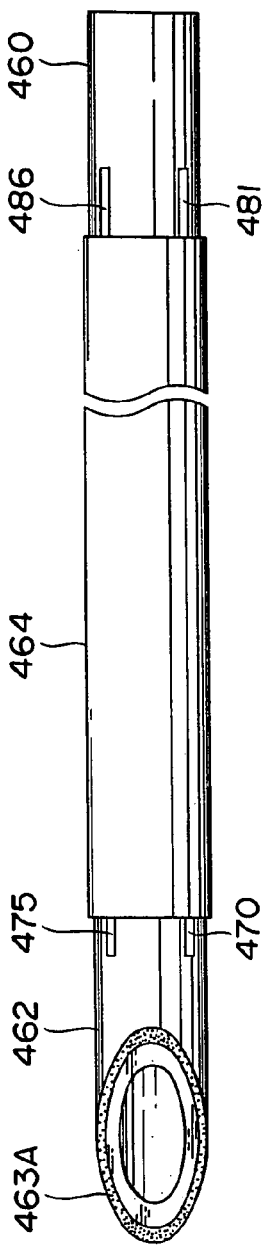
FIG. 20 is a side view for illustrating a step which continues from the step shown in FIG. 19.

Thereafter, a distal end portion 462 of the insertion member 460 is ground to form a bevel 463A (refer to FIG. 20).

The paired electrodes to be used for measuring the impedance can be formed at the distal end portion of the insertion member as described above.

Figure 21:
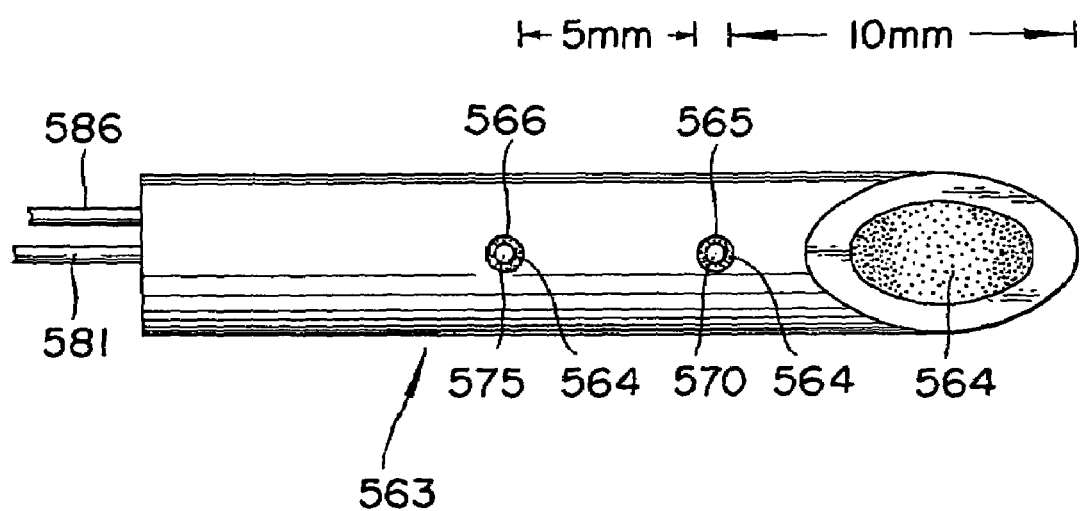
FIG. 21 is a side view for illustrating an injection needle applied to an animal experiment performed for the purpose of verifying the detection of a puncture based on the measurement of impedance.

FIG. 21 is a side view for illustrating an injection needle applied to an animal experiment performed for verifying the detection of the puncture based on the measurement of impedance.

An injection needle 563 used for the puncture was formed as follows. First, lateral holes 565, 566 were formed in a hollow needle made of stainless steel. The hollow needle measured 0.6 mm in outside diameter and 0.3 mm in inside diameter. The lateral hole 565 was positioned as separated by 10 mm from the leading end of the bevel of the hollow needle relative to the longitudinal direction of the hollow needle. The lateral hole 566 was positioned as separated by 5 mm from the lateral hole 565 toward the proximal end side of the longitudinal direction of the hollow needle.

Conductor wires 581, 586 were introduced into the inner space of the hollow needle via the lateral holes 565, 566 and drawn out of the proximal end portion of the hollow needle. The conductor wires 581, 586 had a diameter of 0.08 mm. By potting the inner space of the hollow needle with polyurethane resin, the conductor wires 581, 586 were fixed in the inner space of the hollow needle in a state not touching the inner wall surfaces.

Thereafter, the conductor wires 581, 586 and the polyurethane resin protruding from the lateral holes 565, 566 of the hollow needle were cut off. The outer peripheral surface of the hollow needle near the lateral holes 565, 566 and the cut surface were ground with a file till they had become flat. As a result, electrodes 570, 575 formed of the cut surfaces of the conductor wires 581, 586 and electrical insulators 564 formed of the polyurethane resin encircling the electrodes 570, 575 and the conductor wires 581, 586 were completed to give rise to the injection needle 563 which was applied to an animal experiment.

Now, the contents of the animal experiment will be described below.

First, a swine as a test animal was administered with atrropine, azaperon, and ketamine by intramuscular injection and anesthetized by inhalation of flosen. Then, the swine, with its air tube cut open to admit a pipe from a ventilator and consequently continue respiration, had its ribs spread surgically to expose its heart.

The conductor wires 581, 586 extending from the injection needle 563 were connected to the input terminals of the impedance analyzer and the frequency for the measurement of impedance was set at 128 kHz.

Thereafter, for the purpose of confirming the thickness of the cardiac wall, a test needle was stung into the cardiac tissue from the outer side of the heart and was gradually advanced to an increasingly larger depth. When the leading end of the test needle reached the interior of the ventricle and the blood began to flow out of the proximal end portion of the test needle, the position was marked. The approximate thickness of the heart was measured by extracting the test needle and measuring the length of the test needle from the leading end thereof to the position of the mark.

Next, the injection needle 563 was stung near the mark of the puncture formed by the test needle and operated to measure the impedance in the presence of the electrodes 570, 575 in the cardiac tissue. The impedance was shown to be 80 kΩ. When the injection needle 563 was stung further to advance the electrodes 570, 575 to the position at which they were present in the blood inside the ventricle and the electrodes 570, 575 were operated therein to measure the impedance. The impedance was shown to be 35 kΩ.

Thus, it had been confirmed that the impedance values consequently measured showed a discernible change when the paired electrodes were present in the blood and when they were present in the tissue. That is, it had been verified that the paired electrodes disposed at the distal end portion of the catheter were capable of detecting the puncture with the injection needle.

According to Embodiment 1 and Embodiment 2 described above, a catheter and a catheter system which infallibly accomplish repression of invasion, puncture of target tissue with an injection needle, and injection of therapeutic composition to the target tissue can be provided. Further, a method of injecting a therapeutic composition by the use of a catheter which infallibly accomplishes repression of invasion, puncture of target tissue with an injection needle, and injection of the therapeutic composition to the target tissue can be provided.

This invention is not limited to the catheter and the catheter system according to Embodiment 1 and Embodiment 2 but can be applied to an easy and convenient catheter of good operability according to Embodiment 3 and Embodiment 4 which will be described herein below.

Figure 22:
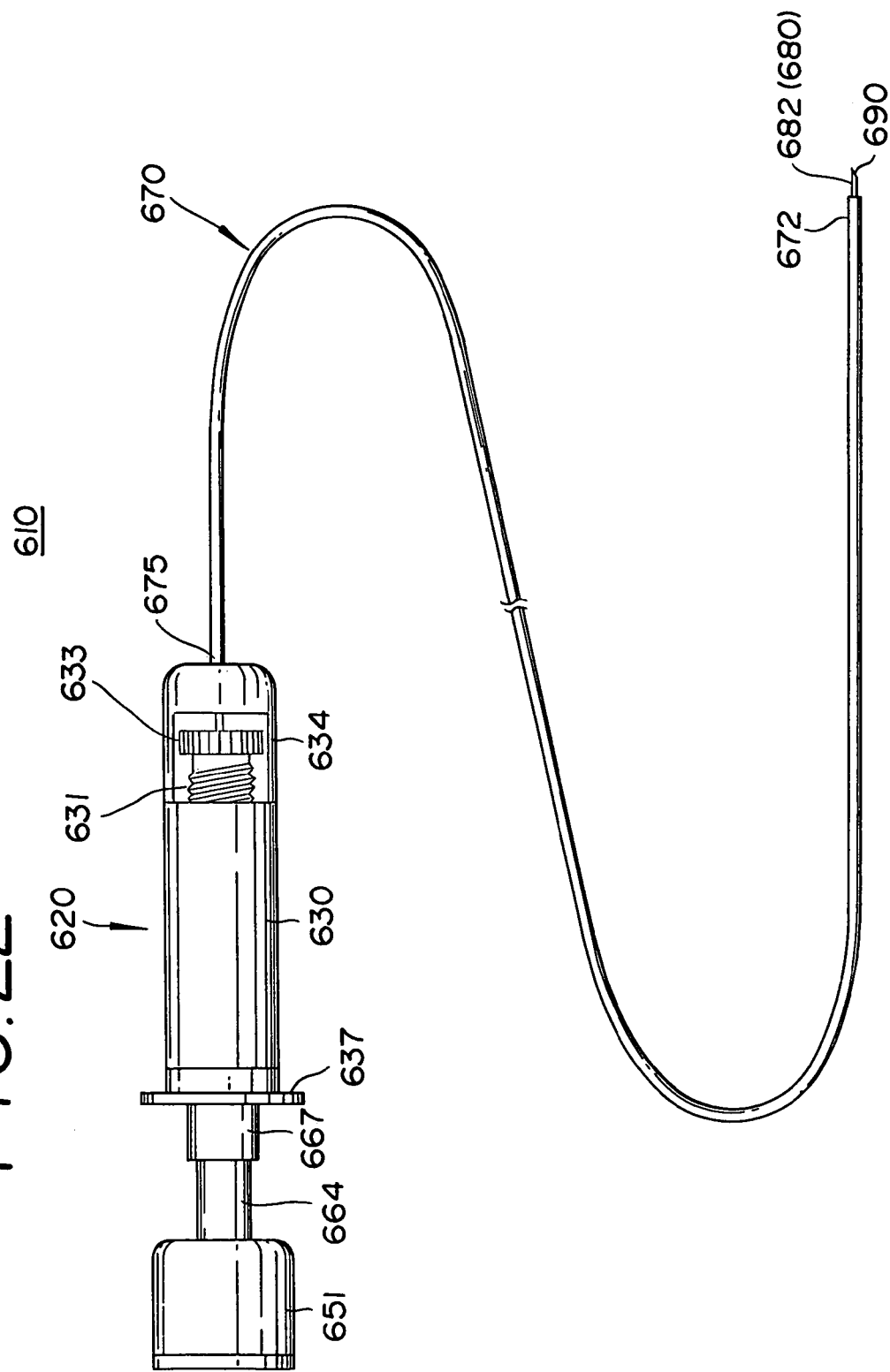
FIG. 22 is a schematic view of a catheter according to Embodiment 3.
Figure 23:
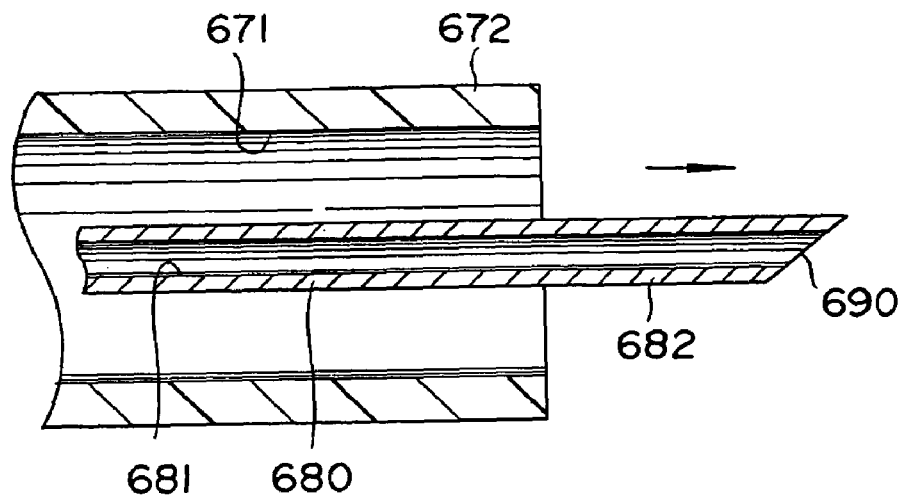
FIG. 23 is a sectional view for illustrating the state of the catheter shown in FIG. 22 having an injection needle protruded out.
Figure 24:
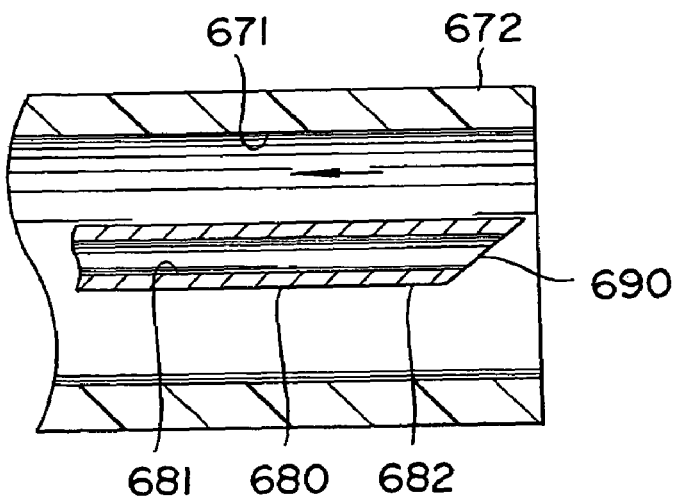
FIG. 24 is a sectional view for illustrating the state of the catheter shown in FIG. 22 having the injection needle retracted to the home position.

FIG. 22 is a schematic view of a catheter according to Embodiment 3. FIG. 23 is a sectional view for illustrating the state of the catheter having an injection needle protruded out. FIG. 24 is a sectional view for illustrating the state of the catheter having the injection needle retracted to home position.

A catheter 610 includes a sheath portion 670, an insertion member 680, an injection needle 690, and an operating unit 620 at its proximal end portion for holding a liquid composition. The liquid composition is a therapeutic composition containing nucleic acid, protein, or cell, for example.

The sheath portion 670 is provided with a lumen 671 extending in the interior thereof and the insertion member 680 slidably extends inside the lumen 671. The outside diameter of the sheath portion 670 does not need to be particularly limited. In the case of the catheter which is required percutaneously to approach the cardiac tissue from inside the ventricle, for example, the outside diameter is preferred to be not more than 10 frenches (3.3 mm). Then, in the case of the catheter which is required to approach the cardiac tissue from outside under observation with an endoscope, for example, the outside diameter is preferred to be not more than 15 mm.

The material for the sheath portion 670 does not need to be particularly limited. Such polymer materials as polyolefins, olefin type elastomers, polyesters, soft polyvinyl chloride, polyurethanes, urethane type elastomers, polyamides, amide type elastomers, polytetrafluoroethylene, fluorine resin elastomers, polyimides, ethylene-vinyl acetate copolymers, and silicone rubbers are usable. In the case of the catheter which is required to approach the cardiac tissue from outside under observation with an endoscope, such metal material as stainless steel, Ni—Ti alloy are also usable.

Polyolefins are polypropylene and polyethylene, for example. Olefin type elastomers are polyethylene elastomer and polypropylene elastomer, for example, Amide type elastomers include polyamide elastomer, for example.

When the sheath portion 670 is formed from a synthetic resin, a pipe of a super-elastic alloy or an embedded coil or embedded mesh made of a metal may be utilized for enhancing the rigidity of the sheath portion 670.

The insertion member 680 is disposed freely slidably in the lumen 671 of the sheath portion 670. The insertion member 680 includes a distal end portion 682 capable of protruding from a distal end portion 672 of the sheath portion 670, a proximal end portion for accepting the liquid composition supplied from the operating unit 620, and a lumen 681 extending in the interior from the proximal end portion through the distal end portion 682 and used for introducing the liquid composition.

The material for the insertion member 680 does not need to be restricted. Metals, high polymer materials having comparatively high rigidity, and proper combinations thereof are available, for example. As concrete examples of such metals, stainless steel, Ni—Ti alloy, Cu—Zn alloy, cobalt alloys, and tantalum may be cited. High polymer materials include polyamide, polyimide, extremely high molecular weight polyethylene, polypropylene, and fluorine resin.

The outside diameter of the insertion member 680 does not need to be particularly limited but is only required to be such that the insertion member 680 may be slidable inside the lumen 671 of the sheath portion 670. It is preferred to fall in the range of 0.3-1.0 mm. The inside diameter of the insertion member 680 does not need to be particularly limited. It is, however, preferred to be in the range of 0.2-0.9 mm.

The injection needle 690 is disposed at the distal end portion 682 of the insertion member 680 and is allowed to communicate with the lumen 681. The injection needle 690, therefore, is enabled to inject to the target site the liquid composition which is supplied via the lumen 681 of the insertion member 680. The target site into which the liquid composition is injected is a diseased part in the living body such as the cardiac tissue like the ischemic part of the heart or the peripheral part thereof.

The injection needle 690 can be constructed, for example, by subjecting the distal end portion 682 of the insertion member 680 to a needle-forming processing to form a cutting edge surface like a bevel, or by mounting and fixing a separate injection needle to the distal end portion 682 of the insertion member 680.

Figure 25:
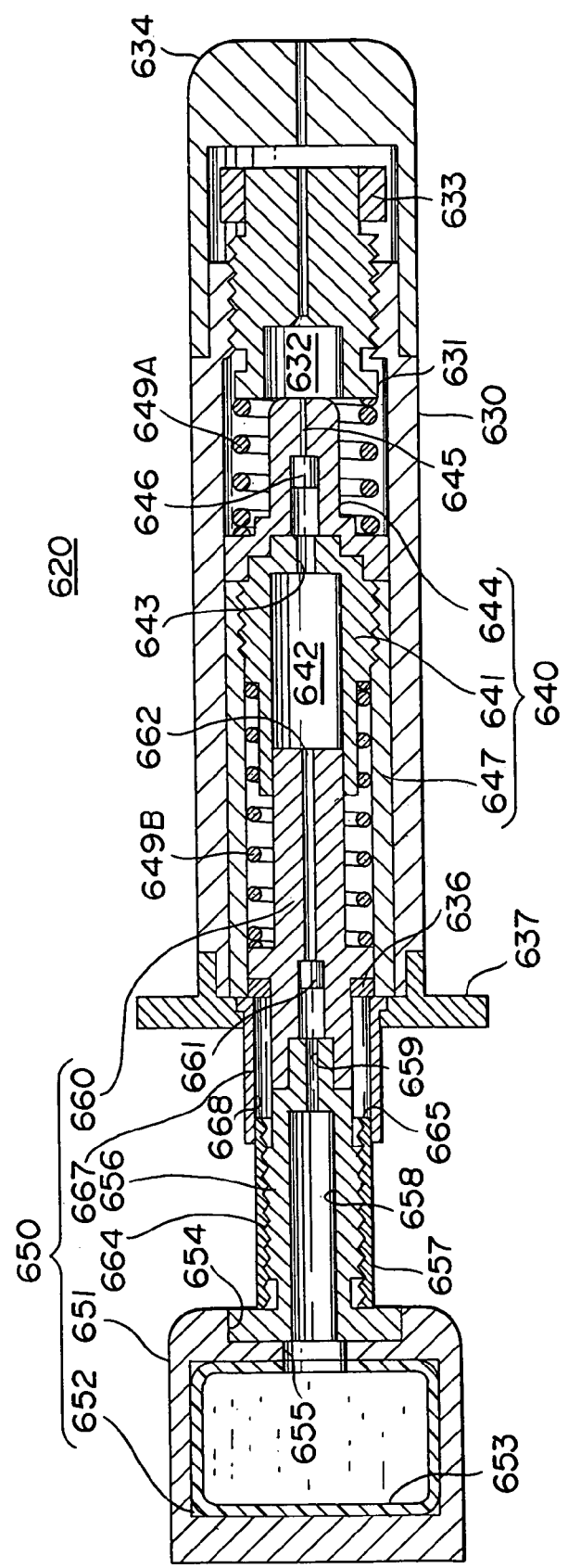
FIG. 25 is a sectional view for illustrating an operating unit at the proximal end portion of the catheter shown in FIG. 22.
Figure 26:
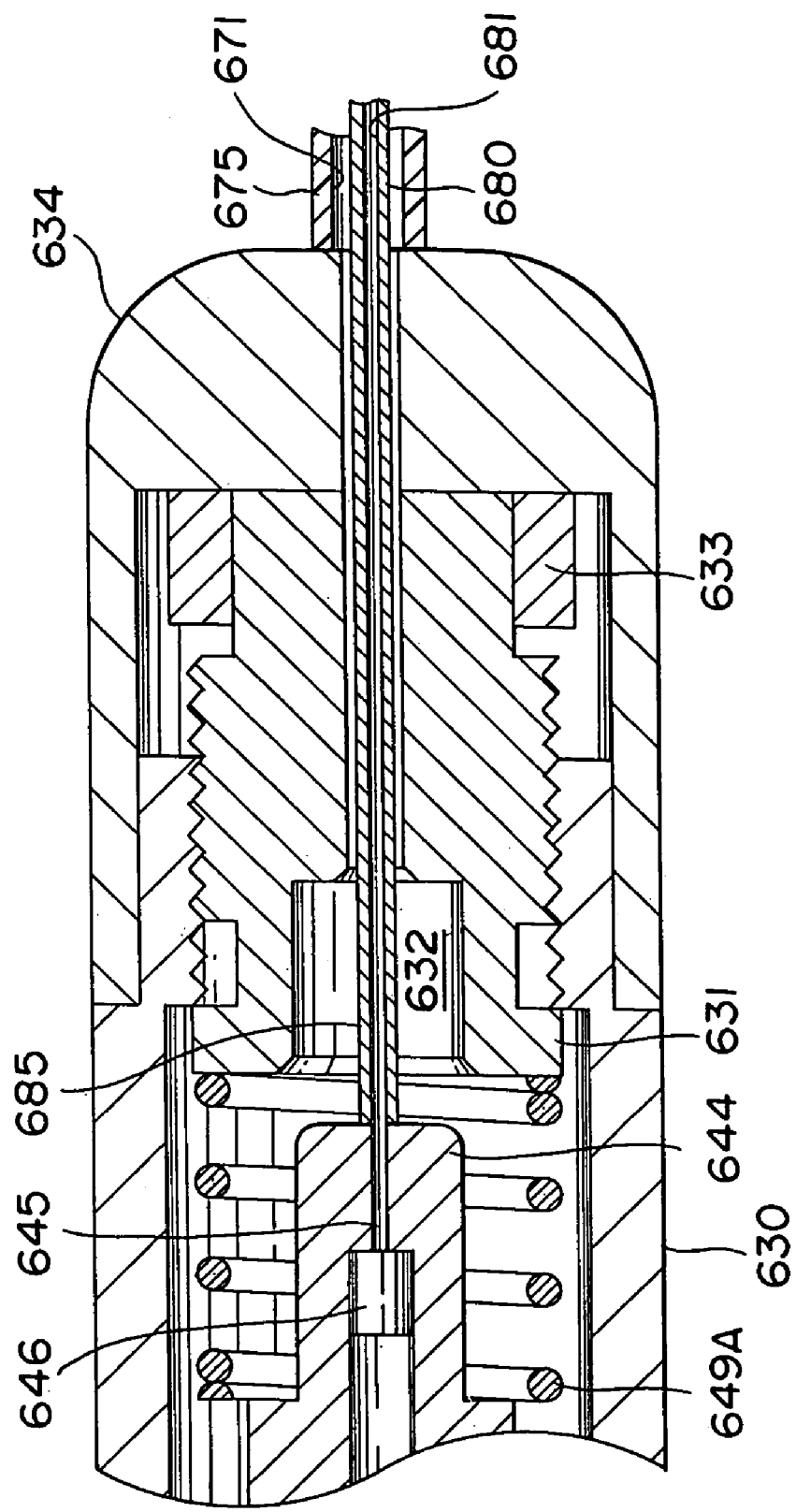
FIG. 26 is an enlarged sectional view for illustrating a mechanism for adjusting the amount of protrusion of the injection needle.
Figure 27:
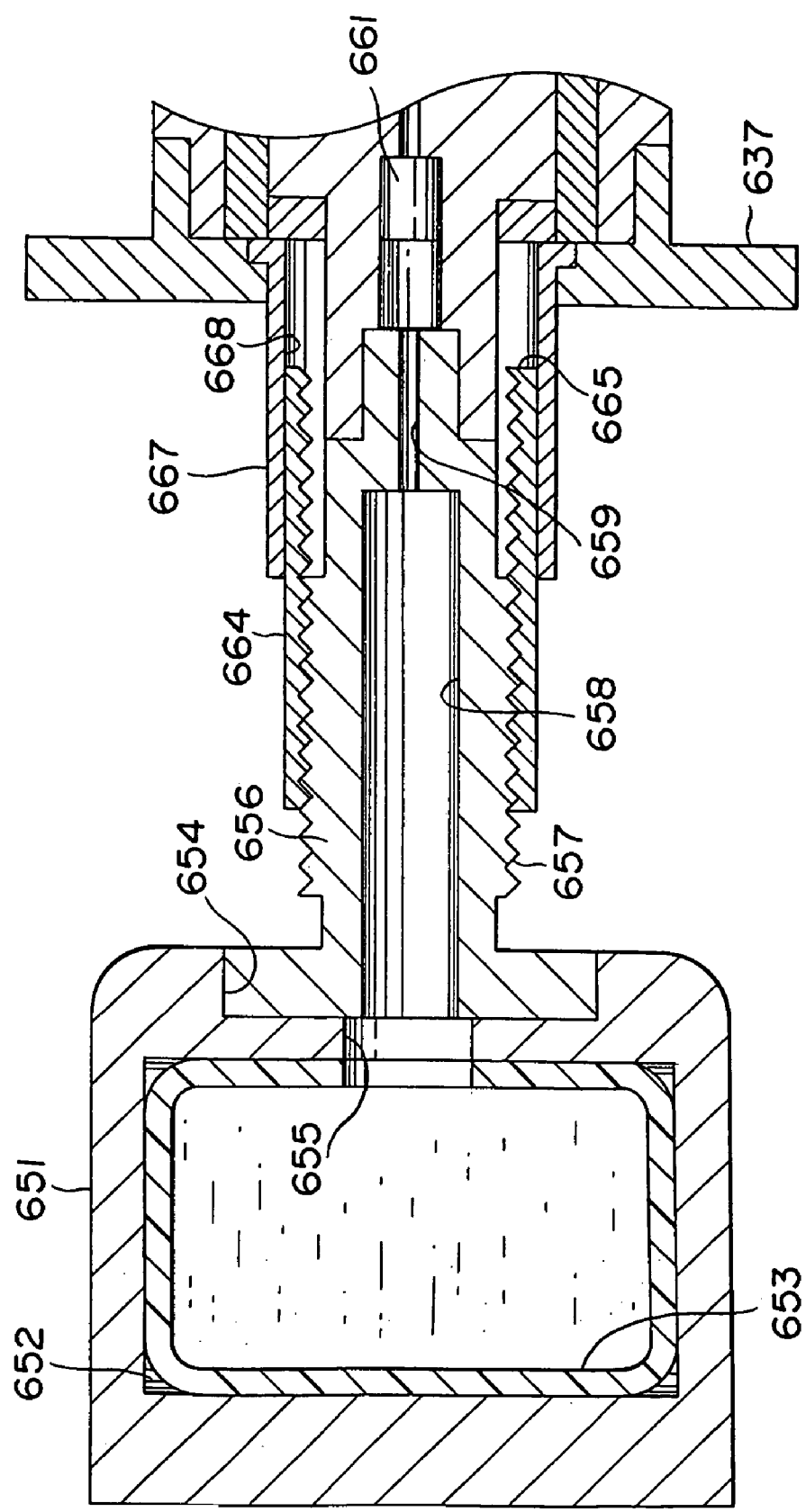
FIG. 27 is an enlarged sectional view for illustrating a mechanism for adjusting the amount of injection of a liquid composition.

FIG. 25 is a sectional view for illustrating the operating unit 620 of the catheter 610. FIG. 26 is an enlarged sectional view for illustrating a mechanism for adjusting the amount of protrusion of the injection needle 690. FIG. 27 is an enlarged sectional view for illustrating a mechanism for adjusting the amount of the liquid composition to be injected. However, FIG. 25 omits the sheath portion 670 and the insertion member 680.

The operating unit 620 includes a cap 634 to which a proximal end portion 675 of the sheath portion 670 is fixed, an outer cylinder 630, an inner cylinder 640, and a push rod 650. The outer cylinder 630 holds the inner cylinder 640 therein. A rear stopper 637 is disposed at the proximal end portion of the outer cylinder 630.

The rear stopper 637 includes an annular protrusion and a cylindrical body. It is fixed as with screws to the proximal end portion of the outer cylinder 630. The rear stopper 637 functions as a hook for the finger being used in pressing (by application of pressure) the push rod 650 and facilitates the use of the push rod 650.

The outer cylinder 630 is provided at the distal end portion thereof with a radical shrink part possessing an inner peripheral surface having formed therein a thread groove and further with a front stopper 631. The front stopper 631 includes an outer peripheral surface having formed therein a thread groove and is attached by threaded insert to the radial shrink part of the outer cylinder 630. The front stopper 631 includes and a cylindrically recess 632 corresponding to the protrusion of a nozzle 644 which will be specifically described herein below, and a through-hole extending from the bottom of the recess 632 toward the distal end side. On the lateral side of the recess 632, an annular protrusion is formed.

A first adjusting ring 633 is interposed between the front stopper 631 and the cap 634. The first adjusting ring 635 is fixed on the front stopper 631. When the first adjusting ring 633 is rotated, therefore, the front stopper 631 is driven to establish close union between the thread groove on the distal end portion of the outer cylinder 630 and the thread groove on the front stopper 631 and move the front stopper 631 in the axial direction. That is, the first adjusting ring 633 functions to change the position of the front stopper 631.

When the front stopper 631 moves in the proximal direction, the collision of the first adjusting ring 633 against the end face of the radial shrink part of the outer cylinder 630 results in restraining the front stopper 631 because the outside diameter of the first adjusting ring 633 is larger than the inside diameter of the radial shrink part of the outer cylinder 630. In contrast, when the front stopper 631 moves in the distal direction, the collision of the protrusion formed on the lateral side of the recess 632 of the front stopper 631 against the radial shrink part of the outer cylinder 630 results in restraining the front stopper 631. The movement of the front stopper 631, therefore, is restricted in a proper range.

Now, the inner cylinder 640 will be explained below. The inner cylinder 640 is disposed slidably in the interior of the outer cylinder 630 and includes a syringe 641, a nozzle 644, and an inner cylinder body 647.

The nozzle 644 which constitutes the distal end portion of the inner cylinder 640 is disposed between the syringe 641 and the front stopper 631 so that the movement thereof in the distal direction will be restrained by the front stopper 631. On the distal end portion of the nozzle 644, a protrusion corresponding to the shape of the recess 632 of the front stopper 631 is formed.

On the proximal end portion of the nozzle 644, a recess corresponding to the shape of the distal end portion of the syringe 641 is formed. The recess is in a shape formed by superposing cylinders stepwise, and includes an annular protrusion. A compression coil spring (resilient member) 649A for urging the nozzle 644 in the proximal direction is disposed between the annular protrusion and the end face of the recess of the front stopper 631.

The outward movement of the compression coil spring 649A disposed in the interior of the outer cylinder 630 is restrained by the inner peripheral surface of the outer cylinder 630. The compression coil spring 649A is deformed by the advance of the nozzle 644 in the distal direction and is allowed to restore itself by the retraction of the nozzle 644 in the proximal direction (the home position).

The nozzle 644 further includes a through-hole 645 which extends from the bottom surface of the recess of the proximal end portion toward the end face of the protrusion of the distal end portion. A proximal end portion 685 of the insertion member 680 is fixed on the end face of the protrusion of the distal end portion (refer to FIG. 26) so that the movement of the nozzle 644 will result in driving the injection needle 690 of the distal end portion 682 of the insertion member 680.

The through-hole 645 and the lumen 681 of the insertion member 680 communicate with each other and a one-way valve 646 is disposed in the interior of the through-hole 645. The one-way valve 646 prevents the liquid composition from flowing back through the lumen 681 of the insertion member 680.

The position of the front stopper 631 serving to restrain the movement of the nozzle 644 in the distal direction may be varied by the first adjusting ring 633. As a result, the movable range of nozzle 644 is widened (the amount of protrusion of the injection needle 690 is increased), for example, when the first adjusting ring 633 is rotated to advance the front stopper 631 in the distal direction as shown in FIG. 26.

In short, the amount of protrusion of the injection needle can be adjusted by manipulating the first adjusting ring 633, and thus the operating unit 620 possesses the mechanism for adjusting the amount of protrusion of the injection needle 690. A scale indicating degrees of protrusion of the injection needle 690 corresponding to the amount of rotation of the first adjusting ring 633 may be placed on the outer peripheral surface of the first adjusting ring 633. In this case, the amount of protrusion of the injection needle is easily and accuracy comprehended.

The syringe 641 includes a cylindrical recess 642 allowing a piston 660 of the push rod 650 to be slidably inserted, a through-hole 643 extending from the bottom surface of the recess 642 toward the leading end, an annular protrusion corresponding to the shape of the proximal end portion of the nozzle 644, and a lateral protrusion. The annular protrusion is in a shape formed by superposing cylinders stepwise.

The piston 660 which constitutes the distal end portion of the push rod 650 is inserted into the recess 642 of the syringe 641 and used for introducing the liquid composition held in the recess 642 of the syringe 641 via the through-hole 643 into the nozzle 644.

The piston 660 includes a cylindrical recess allowing a one-way valve 661 to be disposed therein, a through-hole 662 extending from the bottom surface of the recess, and an annular protrusion formed on the lateral surface. A compression coil spring (resilient member) 649B is interposed between the annular protrusion of the piston 660 and the annular protrusion of the syringe 641. The compression coil spring 649B urges the syringe 641 and the piston 660 away from each other (i.e. urges the syringe 641 toward the distal direction and, at the same time, urges the piston 660 toward the proximal direction).

The one-way valve 661 prevents the liquid composition supplied to the recess 642 of the syringe 641 from flowing back via the through-hole 662. The annular protrusion of the piston 660 is supported by an annular member 636 fixed on the proximal end portion of the cylindrical body 647 which will be specifically described herein below, to restrict the movement of the piston 660 toward the proximal direction. Since the interior of the recess 642 develops negative pressure while the piston 660 retracts from the recess 642 of the syringe 641, the liquid composition is automatically introduced via the through-hole 662 into the recess 642.

The cylindrical body 647 has the piston 660 disposed therein. Further, the cylindrical body 647 is so disposed as to cover the piston 660 with the compression coil spring 649B and the syringe 641 and then restrain the outer movement of the compression coil spring 649B.

The compression coil spring 649A disposed in the interior of the outer cylinder 630 has a smaller coefficient of elasticity than the compression coil spring 649B disposed in the interior of the inner cylinder 640. When the piston 660 is advanced in the distal direction, therefore, the compression coil spring 649B supported by the annular protrusion of the piston 660 is enabled to move the inner cylinder 640 in the distal direction in spite of the compression coil spring 649A urging the nozzle 644 in the proximal direction (by deforming the compression coil spring 649A).

The distal end portion of the nozzle 644 continues to move till it collides against the bottom part of the recess 642 of the front stopper 631. As a result, the injection needle 690 which is positioned at the distal end portion 682 of the insertion member 680 fixed to the distal end portion of the nozzle 644 protrudes from the distal end portion 672 of the sheath portion 670 (refer to FIG. 23).

When the piston 660 is further advanced in the distal direction, the compression coil spring 649B deforms and the piston 660 slides in the interior of the recess 642 of the syringe 641 in the distal direction. As a result, the liquid composition which is held in the recess 642 of the syringe 641 is introduced via the nozzle 644 into the insertion member 680 and discharged through the injection needle 690.

Subsequently, when the piston 660 is retracted in the proximal direction, first the compression coil spring 649B restores itself, the piston 660 slides in the interior of the recess 642 of the syringe 641 in the proximal direction, and then the interior of the recess 642 of the syringe 641 develops negative pressure. As a result, the liquid composition for the next round of administration is automatically introduced via the through-hole 662.

When the piston 660 is further retracted in the proximal direction, the injection needle 690 is retracted into the interior of the distal end portion 672 of the sheath portion 670 because the compression coil spring 6649A restores itself and causes the nozzle 644 to move in the proximal direction (refer to FIG. 24).

Next, the push rod 650 will be explained. The push rod 650, which is disposed at the rear end of the operating unit 620, includes a main body 651 of push rod, a reservoir 652, a support shaft 656, the piston 660, a second adjusting ring 664, and a guide ring 667.

The reservoir 652 is disposed in the main body 651 (the proximal end portion of the push rod 650) positioned at the proximal end of the push rod 650, and is provided in the interior thereof with a soft container 653 of the shape of a bag for holding the liquid composition.

Since the amount of the liquid composition gradually decreases during the operation of the catheter and eventually threatens the possibility of mingling with air, the soft container 653 is at an advantage in facilitating the acquisition of liquid seal in prompt response to the decrease of the amount of the liquid composition. The liquid composition, when necessary, may be directly held in the interior of the reservoir 652. The main body 651 of the push rod 650 includes a groove 654 for fixing the support shaft 656 and a through-hole 655 communicating with the soft container 653.

As the material for the soft container, soft vinyl chloride, soft polypropylene, silicone, polyurethane, and styrene type elastomers are preferred examples. It is also permissible to subject the inner surface of the soft container 653 to a surface treatment designed to prevent the inner surface from adsorbing the components of the liquid composition and extraneous cells.

The support shaft 656 includes a proximal end portion fixed to the groove 654 of the main body 651 of the push rod 650, a cylindrical body 657 with a cylindrical recess 658, a through-hole 659 extending from the bottom surface of the recess 658 toward the distal side, and a distal end portion with a recess corresponding to the proximal end portion of the piston 660.

The through-hole 655 of the main body 651 of the push rod 650 communicates with the one-way valve 661 of the piston 660 via the recess 658 of the support shaft 656 and the through-hole 659. That is, the push rod 650 is provided with a flow path for supplying the liquid composition to the recess 642, and this flow path is formed as extending from the main body 651 which constitutes the proximal end portion of the push rod 650 through the piston 660 which constitutes the distal end portion of the push rod 650. Incidentally, a thread groove is formed on the outer peripheral surface of the cylindrical body 657 of the support shaft 656.

The second adjusting ring 664 is disposed outside the cylindrical body 657 of the support shaft 656, connected to the cylindrical body 657 of the support shaft 656, and enabled to follow the movement of the main body 651 of the push rod 650 to which the support shaft 656 is fixed. Thus, the second adjusting ring 664 restrains the movement of the main body 651 of the push rod 650 in consequence of the collision of an end face 665 of the distal end portion of the second adjusting ring 664 against the annular member 636. That is, the end face 665 of the distal end portion of the second adjusting ring 664 functions as a stopper for restricting the movement of the main body part 651 or the push rod 650 in the distal direction.

The second adjusting ring 664 includes an inner peripheral surface having a thread groove formed therein. The thread groove corresponds to the thread groove of the cylindrical body 657 of the support shaft 656. As a result, the rotation of the second adjusting ring 664 results in establishing union between the thread groove of the second adjusting ring 664 and the thread groove of the cylindrical body 657 of the support shaft 656 to cause the second adjusting ring 664 to move in the distal direction or in the proximal direction, depending on the direction of the rotation. As a result, the movable range of the distal direction of the main body 651 of the push rod 650 is varied.

When the second adjusting ring 664 is rotated to shorten the distance between the end face 665 of the distal end portion of the second adjusting ring 664 and the annular member 636 as shown in FIG. 27, for example, the movable range of the main body 651 of the push rod 650 in the distal direction is decreased.

Since the main body 651 of the push rod 650 is connected to the piston 660 through the support shaft 656, the distance allowed for the forward movement of the piston 660 in the recess 642 of the syringe 641 is decreased as well. As a result, the liquid composition introduced from the recess 642 of the syringe 641 via the nozzle 644 into the insertion member 680 has a smaller volume than before the distance between the end face 665 of the distal end portion of the second adjusting ring 664 and the annular member 636 is shortened.

In short, the amount of the liquid composition injected by the injection needle 690 positioned at the distal end portion 682 of the insertion member 680 can be adjusted by manipulating the second adjusting ring 664, and thus the operating unit 620 includes a mechanism for adjusting the amount of the liquid composition to be injected. It is permissible to place on the outer peripheral surface of the second adjusting ring 664 a scale for indicating amounts of the liquid composition to be injected corresponding to the amounts of rotation of the second adjusting ring 664. In this case, the amount of the liquid composition to be injected is comprehended easily and accurately.

The guide ring 667 is in a cylindrical shape in which the proximal end portion of the piston 660, the support shaft 656, and the second adjusting ring 664 are disposed. The guide ring 667 has a distal side slidably engaging the rear stopper 637 and an inner peripheral surface 668 allowing the adjusting ring 664 to slide thereon smoothly. The provision of this guide ring 667 results in preventing the second adjusting ring 664 and the cylindrical body 657 from being caught on the rear stopper 637 and smoothing the movement of the push rod 650.

As the materials for the component parts of the operating unit 620, polycarbonate, polypropylene, polyethylene, polystyrene, urethane, ABS resin, MBS resin, PMMA resin, stainless steel, aluminum and titanium are available. As the method for forming the component parts of the operating unit 620, injection molding, machining process, and pressing process, for example, are available.

Now, one example of the method of using the catheter 610 will be explained below. The target part is a cardiac tissue, for example, and the liquid composition to be injected is a therapeutic composition for the cure of the injured part of the cardiac tissue.

First, the operator places the prescribed therapeutic composition in the reservoir 652 and rotates the second adjusting ring 664 to adjust the amount of the therapeutic composition to be injected. Then, he rotates the first adjusting ring 633 to set the amount of the injection needle 690 to be protruded.

Subsequently, he hooks his finger on the annular protrusion of the rear stopper 637, causes the main body 651 of the push rod 650 to produce several piston motions, and checks the discharge of the therapeutic composition from the injection needle 690 to prime the injection syringe with the therapeutic composition.

Then, he guides the distal end portion 672 of the sheath portion 670 of the catheter 610 into the ventricle and eventually into close contact with the cardiac tissue as the target region by utilizing a guiding catheter, for example.

Next, he hooks his finger on the annular protrusion of the rear stopper 637 and exerts the force of pressure on the main body 651 of the push rod 650, with the result that the protrusion of the injection needle 690 from the distal end portion 672 of the sheath portion 670, the puncture of the cardiac tissue with the protruded injection needle 690, and the injection of the therapeutic composition into the cardiac tissue are continuously executed owing to the difference in modulus of elasticity between the compression coil springs 649A, 649B.

Since the amount of movement toward the distal direction of the nozzle 644 to which the insertion member 680 is fixed is accurately restricted by the front stopper 631, the amount of protrusion of the injection needle 690 disposed at the distal end portion 682 of the insertion member 680 reflects proper accuracy.

The amount of the movement of the piston 660 for the purpose of supplying the therapeutic composition to the lumen 681 of the insertion member 680 is accurately controlled by the end face 665 of the distal end portion of the second adjusting ring 664, and the one-way valves 646, 661 prevent the therapeutic composition from flowing back. As a result, the amount of the therapeutic composition injected by the injection needle 690 which communicates with the lumen 681 of the insertion member 680 reflects proper accuracy.

When the pressing force exerted for the purpose of pressing the main body 651 of the push rod 650 is released, the retraction of the injection needle 690 relative to the lumen 671 of the distal end portion 672 of the sheath portion 670, and the introduction of the liquid composition for the next round of administration relative to the recess 642 of the syringe 641 are executed continuously owing to the difference in modulus of elasticity between the compression coil springs 649A, 649B.

Then, by moving the catheter 610 to the next target tissue and repeating the procedure described above, it is made possible to implement continuous injection of the therapeutic composition in a prescribed amount to a plurality of sites in the ventricle.

The operating unit 620 of the catheter 610 according to Embodiment 3 includes the push rod 650 which is capable of continuously repeating a step of protruding the injection needle 690 from the distal end portion 672 of the sheath portion 670, a step of puncturing the target site with the protruded injection needle 690 and injecting the liquid composition to the target site, and a step of retracting the injection needle 690 to the lumen 671 of the distal end portion 672 of the sheath portion 670 as a series of operations. Thus, Embodiment 3 is capable of providing an easy convenient catheter 610 with proper operability.

When the catheter 610 is used in a method for regenerating the cardiovascular system, for example, since the catheter 610 is endowed with ample convenience enough for an easy and expeditious operation, the operator is enabled to carry out the necessary steps mentioned above continuously in one hand and perform the therapy conveniently and expeditiously.

Figure 28:
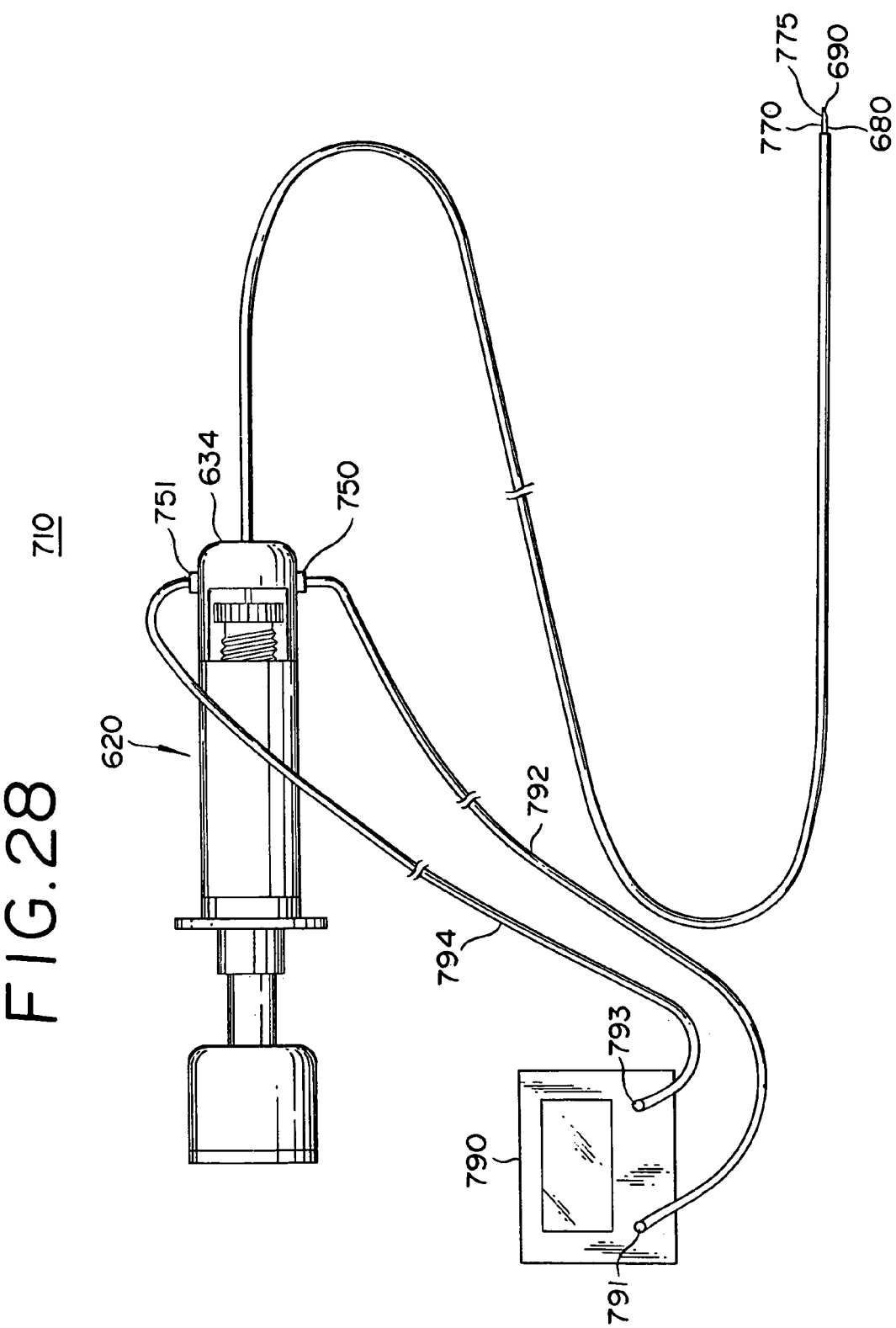
FIG. 28 is a schematic view for illustrating an example of the modification of the catheter according to Embodiment 3.
Figure 29:
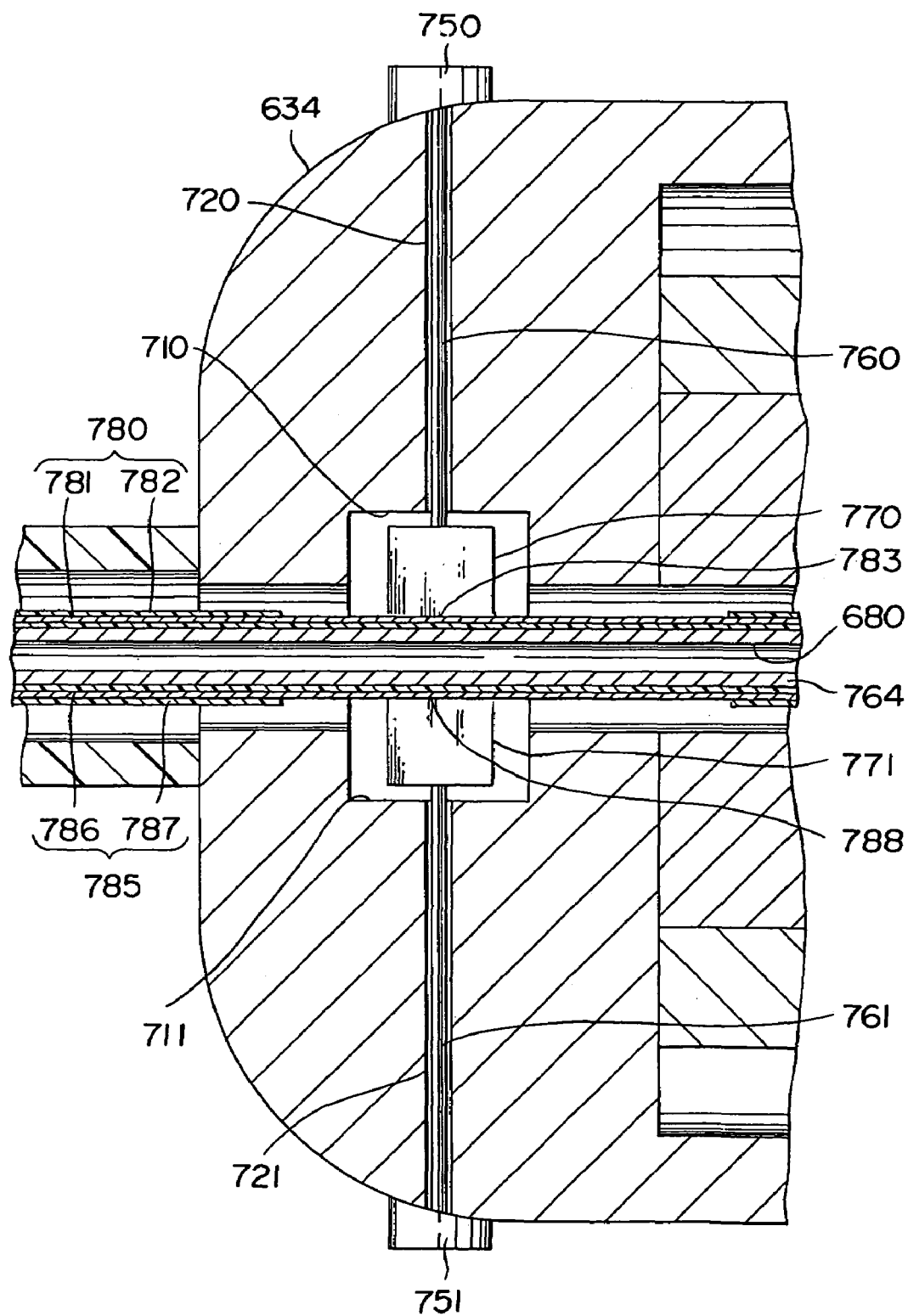
FIG. 29 is a sectional view for illustrating the front end portion of the operating unit at the proximal end portion shown in FIG. 28.

FIG. 28 is a schematic view for illustrating an example of the modification of a catheter according to Embodiment 3. FIG. 29 is a sectional view for illustrating the distal end portion of the operating unit at the proximal end portion shown in FIG. 28.

A catheter 710 roughly differs from the catheter 610 according to Embodiment 3 in being provided with electrodes 770, 775 for measuring the impedance and output terminals 750, 751 for connection to an impedance analyzer 790.

The impedance analyzer 790 includes input terminals 791, 793 connected via cords 792, 794 to the output electrodes 750, 751. The electrodes 770, 775 which adopt the shape shown in FIG. 5, for example, are disposed at the distal end portion of the insertion member 680 in the neighborhood of the bevel of the injection needle 690.

The outer periphery of the insertion member 680 is covered with an electrical insulator 764. Wires 780, 785 extend along the surface of the electrical insulator 764 and are fixed thereon. The wires 780, 785 include conductors 781, 786 having terminals connected to the electrodes 770, 775 and electrical insulators 782, 787 covering the conductors 781, 786.

The output terminals 750, 751 are disposed in the cap 634 of the operating unit 620. The cap 634 includes recess 710, 711 disposed in a hollow part through which the insertion member 680 passes and through-holes 720, 721 extending from the recess 710, 711 outward.

The electrical insulators 782, 787 covering the conductors 781, 786 have removed the portions thereof which fall in the range in which the recess 710, 711 are formed, with the conductors 781, 786 exposed through the removed portions. In the recess 710, 711, contactors 770, 771 are disposed in such a manner as to slide freely along the conductors 781, 786. The contactors 770, 771 are electrical conductors in the shape of a brush, for example, and are designed not to obstruct the movement made by the insertion member 680 in causing the injection needle to protrude.

The contactors 770, 771 have connected thereto cords 760, 761 which extend via the through-holes 720, 721. The cords 760, 761 are connected to the output terminals 750, 751.

The electrodes 770, 775 which are used for measuring the impedance are connected to the output terminals 750, 751 disposed in the cap 634 of the operating unit 620 as described above. Thus, the impedance analyzer 790 is enabled to detect the puncture made by the injection needle 690 on the basis of the impedance values measured by the electrodes 770, 775.

Optionally, the conductors 781, 786 maybe directly connected to the codes 760, 761 not through the contactors 770, 771. In this case, the cords 760, 761 are required to be disposed in a slack state inside the recess 710, 711 so that they may accompany the movement of the insertion member 680.

Figure 30:
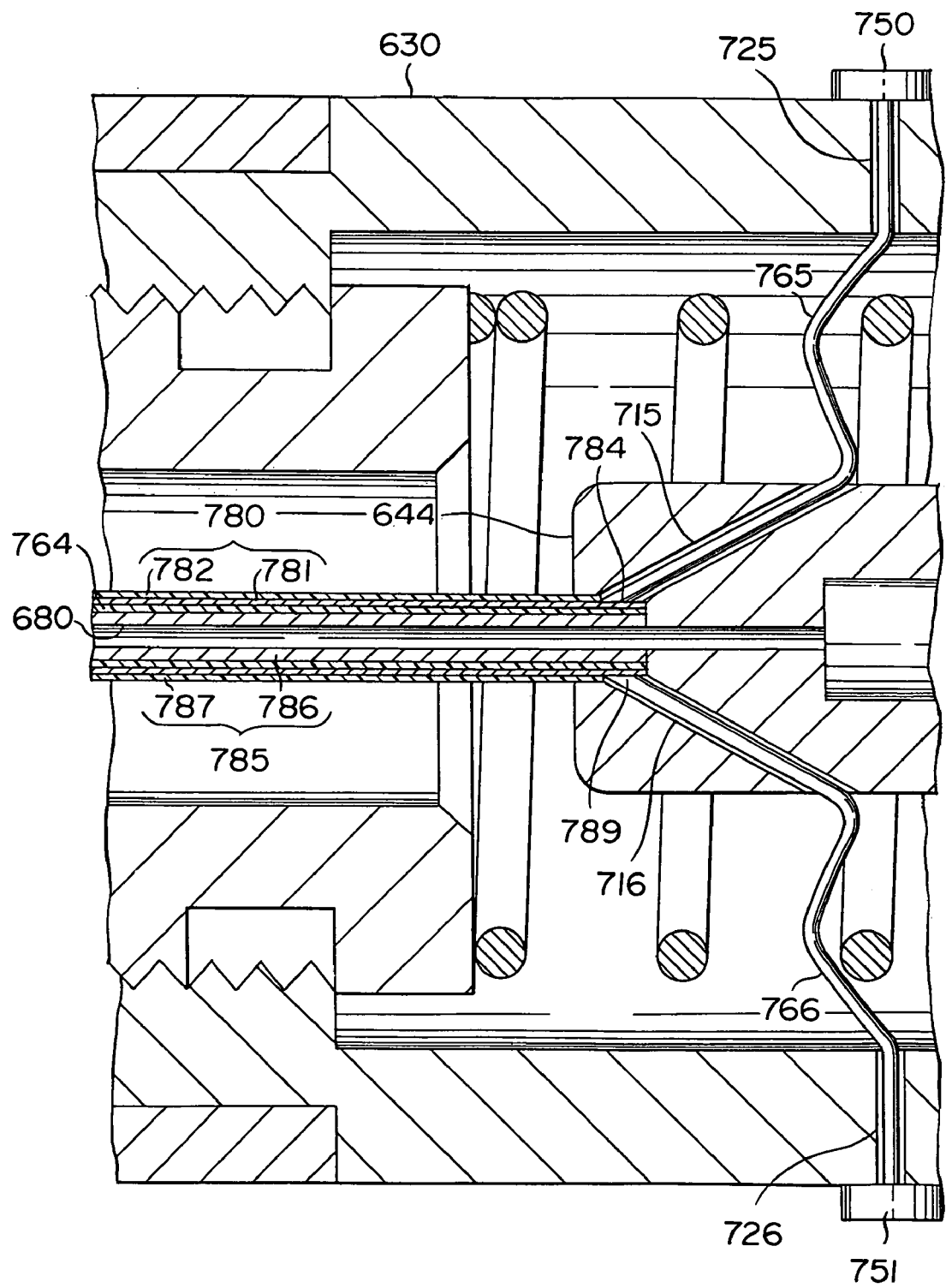
FIG. 30 is a sectional view for illustrating an example of the modification of the front end portion of the operating unit at the proximal end portion.

The conductors 781, 786 which extend from the electrodes 770, 775 do not need to adhere to the aforementioned mode which requires them to connect with the cords 760, 761 extending from the output terminals 750, 751 in the cap 634 of the operating unit 620. FIG. 30 is a sectional view for illustrating an example of the modification of the front end portion of the operating unit at the proximal end portion.

This example of the modification includes through-holes 715, 716 formed in the nozzle 644 to which the proximal end portion of the insertion member 680 is fixed, and through-holes 725, 726 formed in the outer cylinder 630. The output terminals 750, 751 are disposed on the outer cylinder 630.

Then, the electrical insulators 782, 787 covering the conductors 781, 786 have removed portions 784, 789 thereof which face the through-holes 715, 716, with the conductors 781, 786 exposed there through. The exposed portions 784, 789 have cords 765, 766 fixed thereon.

The cords 765, 766 are connected to the output terminals 750, 751 via the through-holes 715, 725 and the through-holes 716, 726. Incidentally, the positions for disposing the through-holes 715, 725 and the lengths of the cords 765, 766 are so fixed as to avoid obstructing the movement of the nozzle 644 for the purpose of protruding the injection needle 690.

Thus, the electrodes 770, 775 which are used for measuring the impedance are connected to the output terminals 750, 751 which are disposed on the outer cylinder 630. That is, even in the example of modification, the impedance analyzer 790 is enabled to detect the puncture with the injection needle 690 on the basis of the impedance values measured by the electrodes 770, 775.

This invention is applicable to the catheter which is contemplated by Embodiment 3 as described above. It can provide a catheter which represses invasion, infallibly accomplishes puncture of the target tissue with the injection needle, and injection of the therapeutic composition to the target tissue, and further enjoys convenience and proper operability. With respect to the above catheter as shown in FIGS. 28, 29 and 30, it can be further made by persons who have common knowledge in the technical field to which the inventions pertains, that the electrodes 770, 775 for measuring the impedance are replaced with other electrodes for various use such as electrodes used as pressure sensors.

Figure 31:
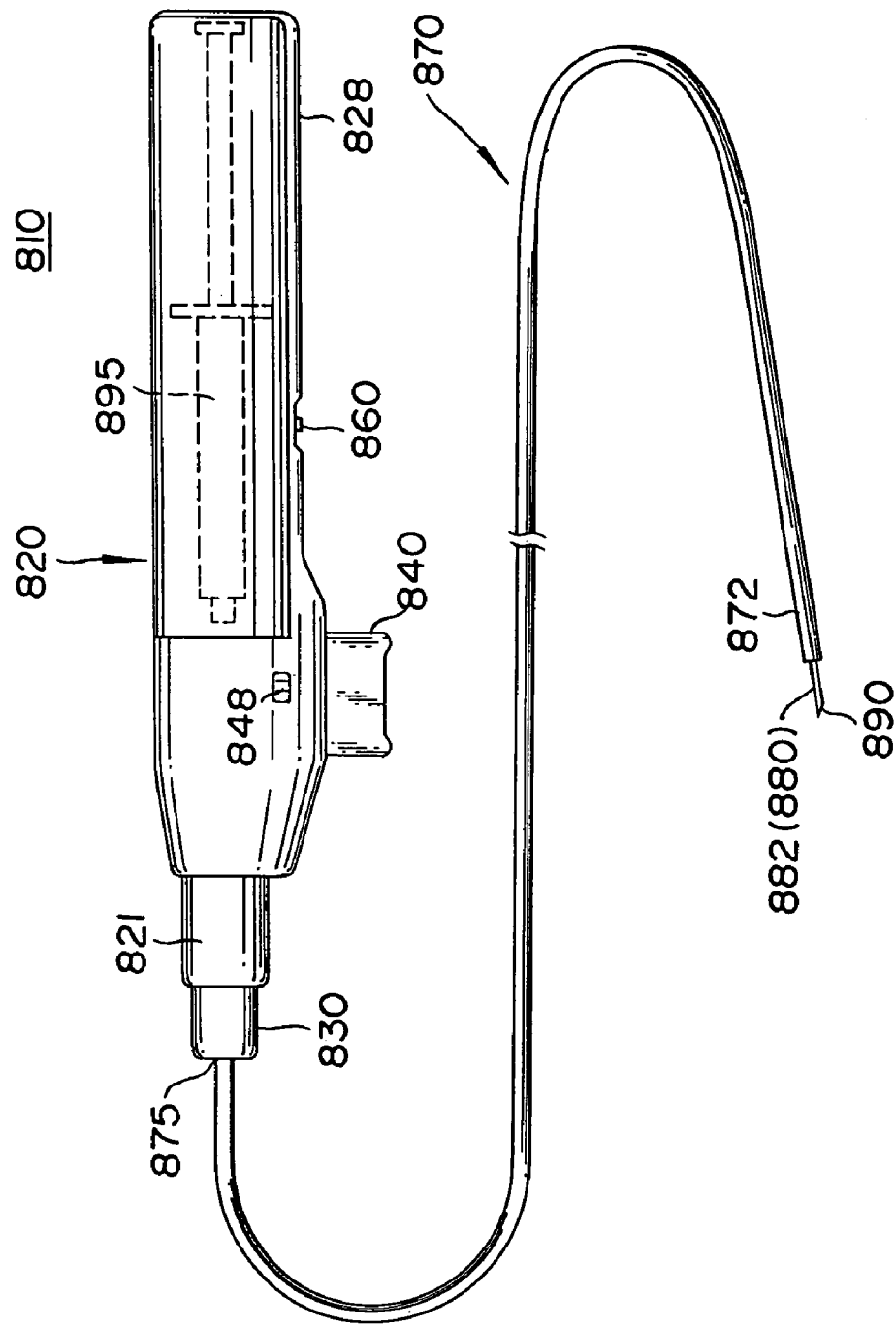
FIG. 31 is a schematic view of a catheter according to Embodiment 4.

FIG. 31 is a schematic view of a catheter according to Embodiment 4. The component members of this catheter which fulfill the same functions as in Embodiment 3 will be denoted by the similar reference numerals and their explanations will be omitted to avoid repetition.

A catheter 810 includes an insertion member 880 having a distal end portion 882 at which an injection needle 890 is disposed, a sheath portion 870 in which the insertion member 880 slidably extends, and an operating unit 820 at hand to which a proximal end portion 875 of the sheath portion 870 is connected.

The insertion member 880 includes a proximal end portion to which a liquid composition is supplied from the operating unit 820, and a lumen extending inside from the proximal end portion through the distal end portion 882, in which a liquid composition is introduced. The distal end portion 882 of the insertion member 880 is enabled to protrude from a distal end portion 872 of the sheath portion. Thus, the injection needle 890 is enabled to inject the liquid composition to the target site by being protruded from the distal end portion 872 of the sheath portion 870 in response to the protruding motion of the insertion member 880 (refer to FIG. 23 and FIG. 24).

The operating unit 820 includes the nozzle 821, an operating button 840, a lock tab 848, an operating tab 860, and a lid 828. The nozzle 821 has detachably attached thereto a cap 830 to which the proximal end portion 875 of the sheath portion 870 is connected, and also has disposed therein a mechanism for adjusting the amount of protrusion of the injection needle 890.

The operating button 840 is disposed on the lateral side of the operating unit 820 and is used for the purpose of actuating the injection needle driving mechanism for protrusion and retraction of the needling needle 890 and the liquid composition injecting mechanism for injecting the liquid composition in a prescribed amount. The lock tab 848 is capable of locking the operating button 840 and preventing the catheter from committing malfunction. The operating tab 860 is used for the purpose of controlling the mechanism which adjusts the amount of the liquid composition to be injected.

The lid 828 is attached to a main case 822 in such a manner as to be opened and closed and locked and is used for the purpose of holding therein a syringe 895 intended to hold the liquid composition. The syringe 895 is disposable in type and is built in the operating unit 820 in a detachable manner. As a result, the liquid composition can be easily replaced and the risk of infection can be decreased as compared with the container which is repeatedly used for holding the liquid composition. The mechanism for opening and closing the lid 828 and the mechanism for locking the lid 828 do not need to be particularly restricted. Optionally, other proper means may be adopted as the need arises.

Figure 32:
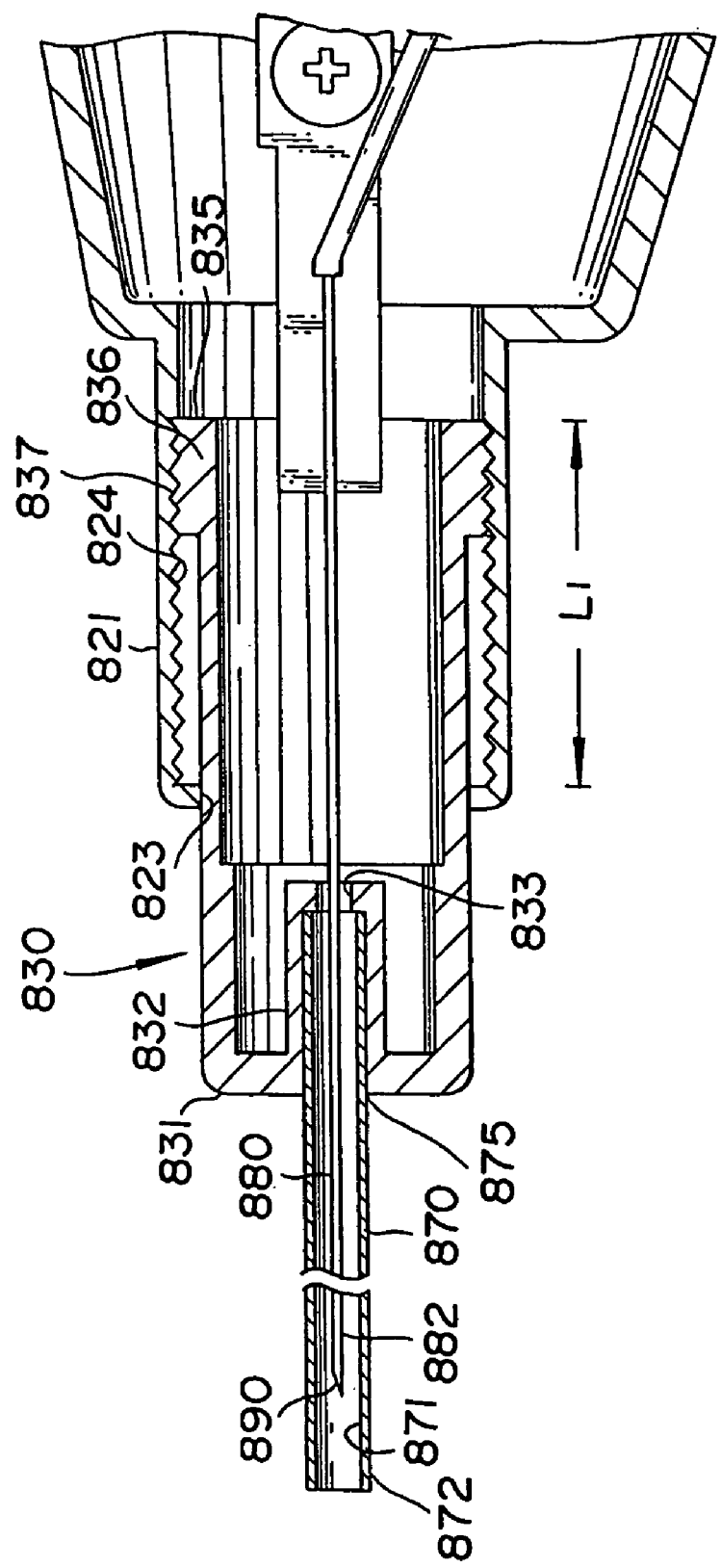
FIG. 32 is a sectional view for illustrating a mechanism for adjusting the amount of protrusion of the injection needle of the catheter, depicting the front end portion of the operating unit at the proximal end portion.

FIG. 32 is a sectional view for illustrating a mechanism for adjusting the amount of protrusion of the injection needle 890 of the catheter 810, depicting the distal end portion of the operating unit 820.

The cap 830 includes a distal end 831 having a cylindrical recess 832 to be formed therein and a proximal end 835 having a radial expansion part 836 to be formed therein. The recess 832 includes an inner peripheral surface to which the outer peripheral surface of the leading end of the proximal end portion 875 of the sheath portion 870 is fixed, and a bottom surface having an opening 833 through which the insertion member 880 slidably extends. The radial expansion part 836 includes an outer peripheral surface for forming a thread groove 837 therein.

The nozzle 821 is in a cylindrical shape and includes a leading end having an opening 823 into which the distal end 831 of the cap 830 is slidably inserted, and an inner peripheral surface with a thread groove 824 formed thereon corresponding to the thread groove 837 of the cap 830. The leading end of the nozzle 821 is radially shrunken and the inside diameter of the opening 823 is smaller than the outside diameter of the radial expansion part 836 of the cap 830. The leading end of the nozzle 821, therefore, functions as a stopper for preventing the cap 830 from falling off.

When the cap 830 is rotated, the thread groove 837 of the cap 830 and the thread groove 824 of the nozzle 821 fit each other and the cap 830 moves away from or toward the nozzle 821 depending on the direction of rotation. The relative positions of the insertion member 880 and the sheath portion 870 are changed because the sheath portion 870 is fixed to the cap 830 and the insertion member 880 is not constrained by the cap 830.

By rotating the cap 830 and changing the relative positions of the insertion member 880 and the sheath portion 870, therefore, it is made possible to adjust the amount of protrusion of the injection needle 890 positioned at the distal end portion 882 of the insertion member 880. Further, the length $L_1$ in which the thread groove 824 is formed constitutes the range in which the amount of the protrusion is adjustable.

As described above, the mechanism for adjusting the amount of the protrusion of the injection needle 890 according to Embodiment 4 is based on the change of the relative positions of the insertion member 880 and the sheath portion 870 which is brought about by the union of the thread grooves 824, 837.

Figure 33:
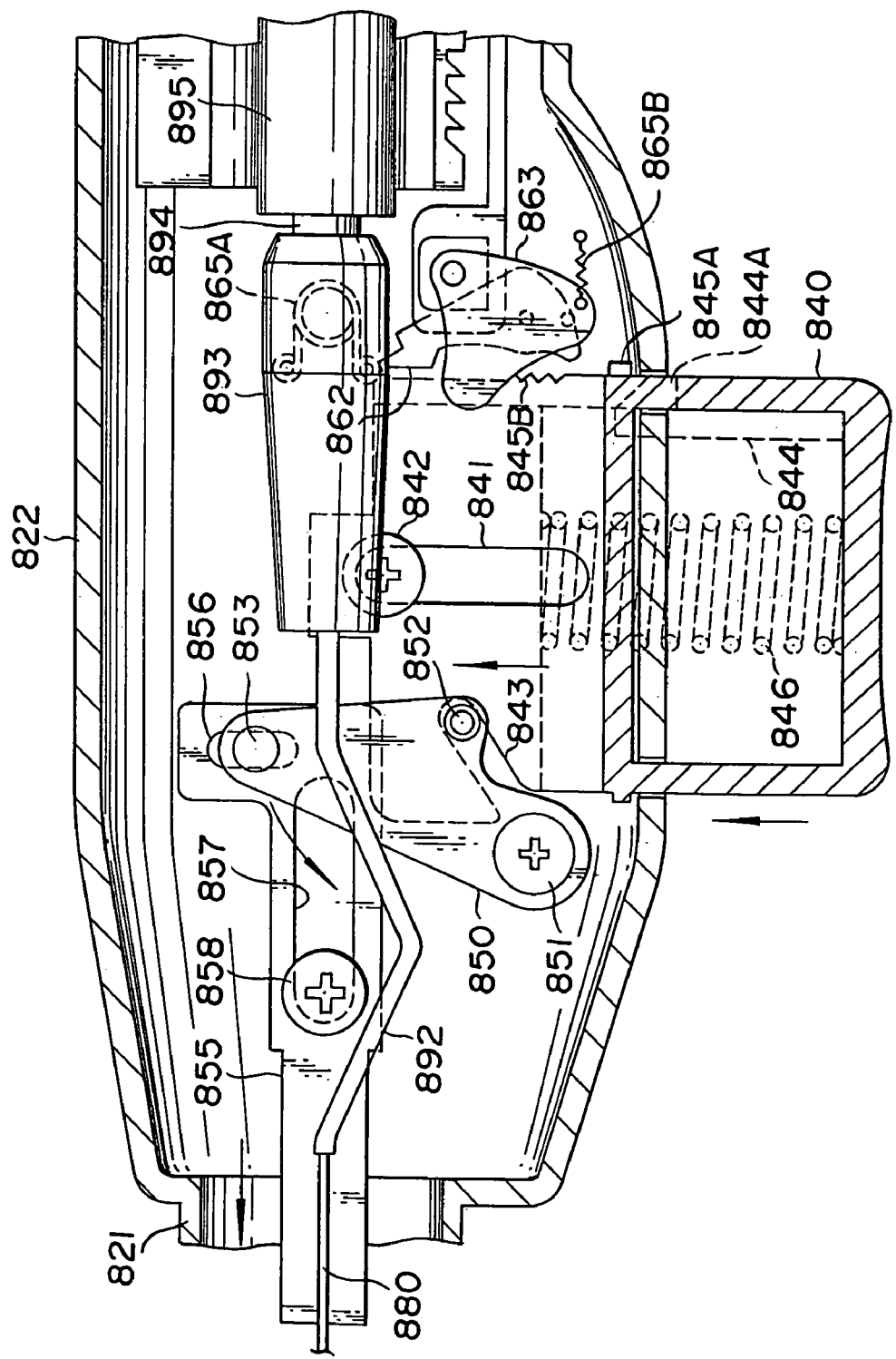
FIG. 33 is a sectional view for illustrating a mechanism for driving the injection needle of the catheter, depicting the neighborhood centering around an operating button of the operating unit at the proximal end portion.
Figure 34:
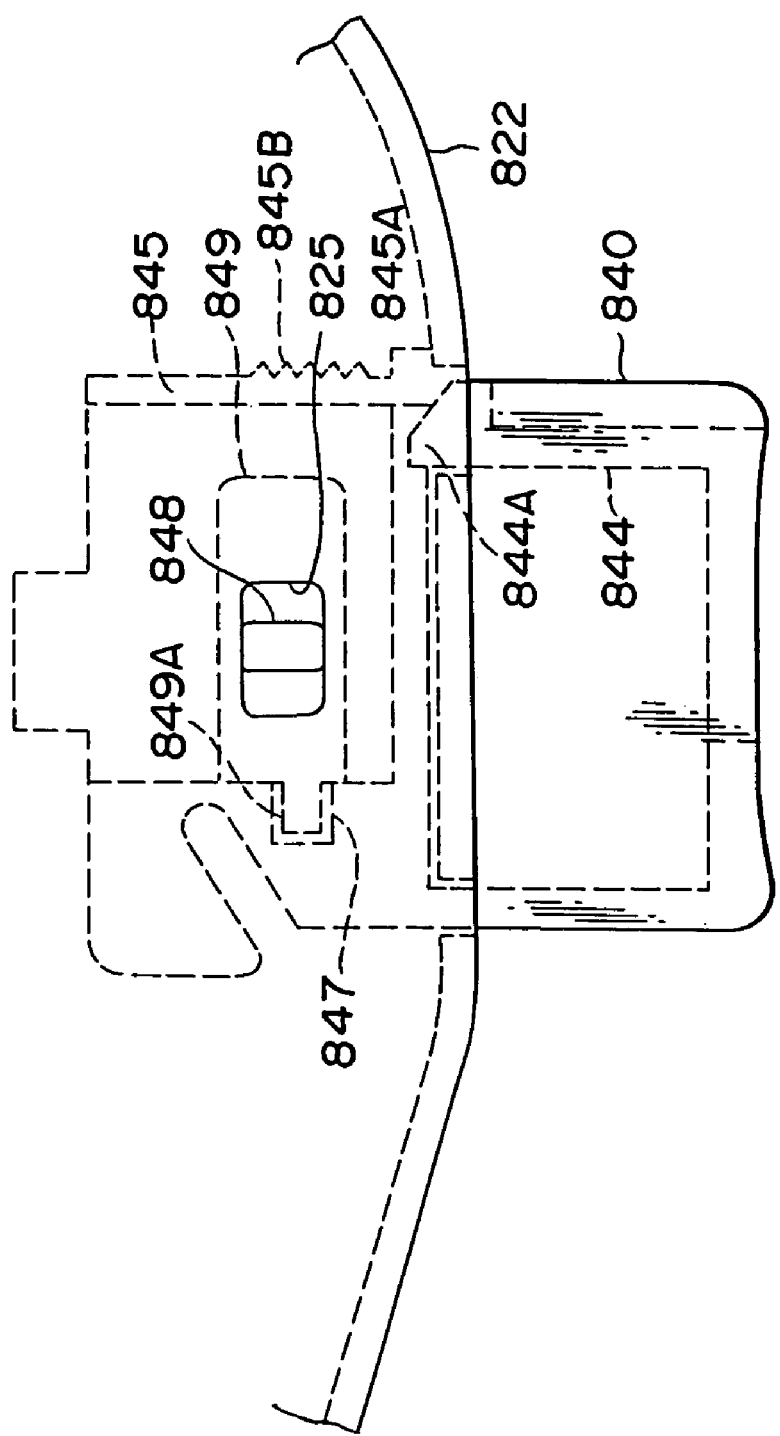
FIG. 34 is a plan view for illustrating a mechanism for locking the operating button.

FIG. 33 is a sectional view for illustrating a mechanism for driving the injection needle of the catheter 810, depicting the neighborhood centering around the operating button 840 of the operating unit 820. FIG. 34 is a plan view for illustrating a mechanism for locking the operating button 840.

The operating button 840 includes an extension in the main case 822. The extension includes a slot 841, a guide groove 843, a pressing member 844, a rack 845, and a recess 847 while the rock tab 848, the transmitting member 850, and a needle driving member 855 are disposed in the vicinity thereof.

The slot 841 has an oblong shape into which a guide pin 842 fixed to the main case 822 is slidably inserted. As a result, when the operating button 840 is pressed, the inner periphery of the slot 841 slides on the outer periphery of the guide pin 842 and the operating button 840 is consequently moved toward the interior of the main case 822.

The guide groove 843 has a semi-oblong shape and is used for the purpose of interlocking the operating button 840 and the transmitting member 850. The pressing member 844 possesses elasticity and flexibility, and includes a triangular distal end 844A. The rack 845 includes a protrusion 845A and a plurality of serrated portions 845B. The distal end 844A and the protrusion 845A are disposed as approximated to each other. The operating button 840 actuates the injection needle driving mechanism as soon as it moves while the transmitting member 850 of the injection needle driving mechanism, on revolving, moves the needle driving member 855 toward the cap 830 (refer to FIG. 33). Since the insertion member 880 is fixed to the needle driving member 855, the injection needle 890 disposed in the distal end portion 882 of the insertion member 880 protrudes from the distal end portion 872 of the sheath portion 870 according to the amount of protrusion set by the mechanism for adjusting the amount of protrusion.

The distal end 844A, the protrusion 845A, and the serrated portion 845B are used for the purpose of interlocking the operating button 840 and the mechanism for injecting the liquid composition. The operating button 840 is provided in the interior thereof with a spring (resilient member) 846, which urges the operating button 840 outward.

The lock tab 848, as illustrated in FIG. 34, is disposed slidably in the opening 825 which is formed in the main case 822. The opening 825 has an oblong shape. The lock tab 848 includes a base 849 of a rectangular shape disposed in the interior of the main case 822. The base 849 has a larger shape than the opening 825, and includes a projection 849A.

The recess 847 of the operating button 840 and the projection 849A are aligned and possess corresponding shapes. When the lock tab 848 is moved toward the recess 847, therefore, the projection 849A and the recess 847 are engaged to lock the operating button 840. In contrast, when the lock tab 848 is moved in the direction parting from the recess 847, the union between the projection 849A and the recess 847 is released and the operating button 840 becomes movable.

The operating unit 820 is endowed with a function of locking the operating button 840 as described above. By properly locking the movement of the operating button 840, it is made possible to prevent the operating button 840 from malfunctioning.

The transmitting member 850 which has a triangular shape is supported swingably around a shaft 851 and provided with through-holes into which connecting pins 852, 853 are inserted, respectively. The connecting pin 852 is connected slidably to the guide groove 843 of the operating button 840.

Since the guide groove 843 presses the connecting pin 852 when the operating button 840 is moved toward the interior of the main case 822, the transmitting member 850 is revolved around the shaft 851. In this case, the connecting pin 852 is made to move along the guide groove 843. Incidentally, the connecting pin 853 is used for interlocking the transmitting member 850 and a needle driving member 855.

The insertion member 880 to which a flexible hollow tube 892 is connected loosely is fixed to the needle driving member 855. The tube 892 extends from the plug 893 detachably connected to the nozzle 894 of the syringe 895 and used for passing there through the liquid composition held in the syringe 895. As the proper material for the tube 892 and the plug 893, vinyl chloride, soft polypropylene, silicone, polyurethane, and styrene type elastomers are available.

A needle driving member 855 which has the shape of L includes oblong slots 856, 857 disposed in intersecting directions. The connecting pin 853 of the transmitting member 850 is connected to the slot 856. The guide pin 858 fixed to the main case 822 is slidably inserted into the slot 857.

Since the outer periphery of the connecting pin 853 presses the inner periphery of the slot 856 when the transmitting member 850 is revolved, the inner periphery of the slot 857 slides on the outer periphery of the guide pin 858 and the needle driving member 855 moves toward the cap 830. In this case, the outer periphery of the connecting pin 853 is made to slide and move on the inner periphery of the slot 856. Since the insertion member 880 is fixed to the needle driving member 855, the injection needle 890 disposed at the distal end portion 882 of the insertion member 880 protrudes from the distal end portion 872 of the sheath 870.

When the operating button 840 is pressed in the direction of the interior of the main case 822, it revolves the transmitting member 850 and the transmitting member 850 move the needle driving member 855 toward the cap 830. In short, the mechanism for driving the injection needle according to Embodiment 4 is based on the conversion of the descending motion induced by the pressing motion of the operating button 840 via the revolving motion of the transmitting member 850 to the advancing motion of the needle driving member 855, the insertion member 880, and the injection needle 890.

Figure 35:
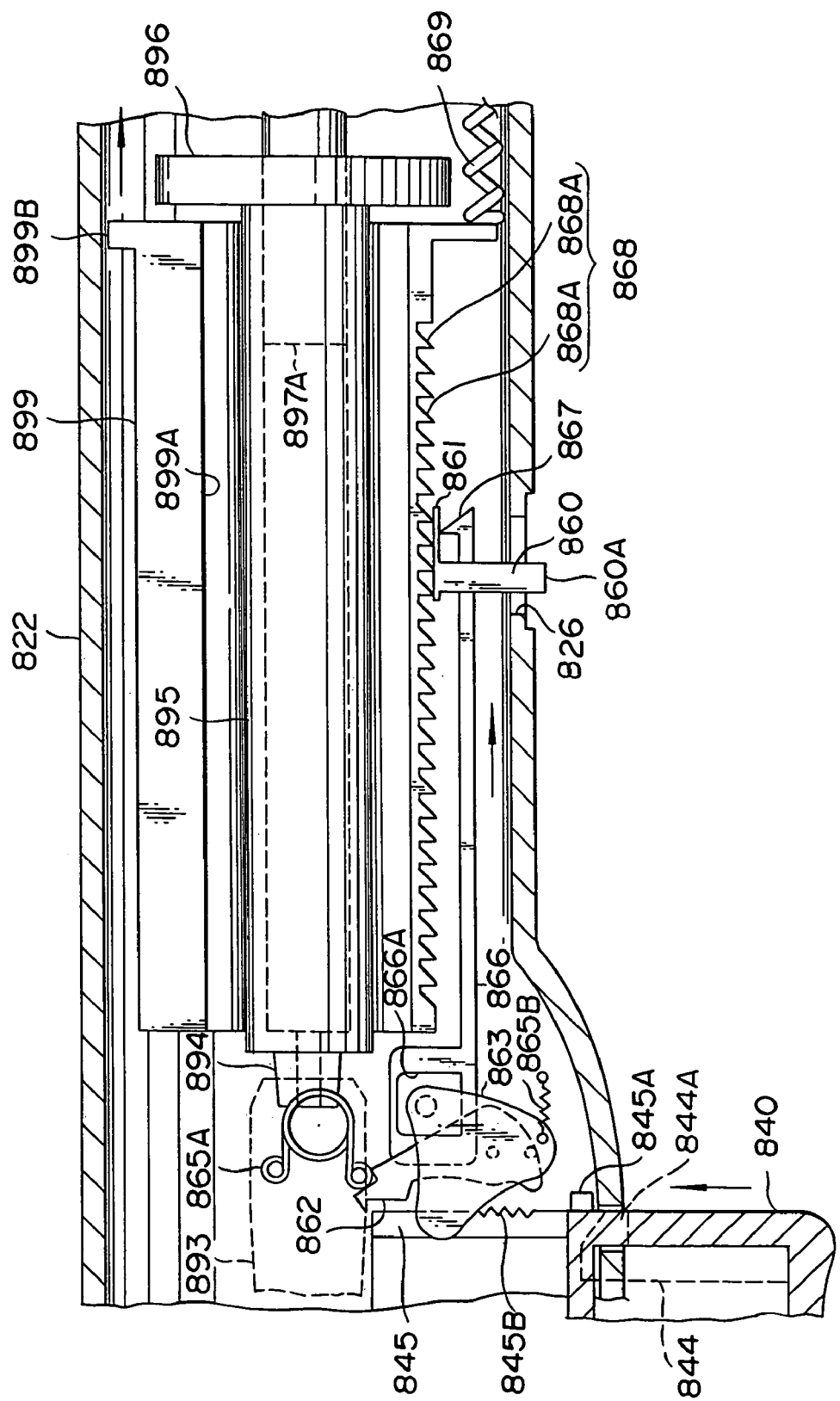
FIG. 35 is a sectional view of the intermediate portion of the operating unit at the proximal end portion.
Figure 36:
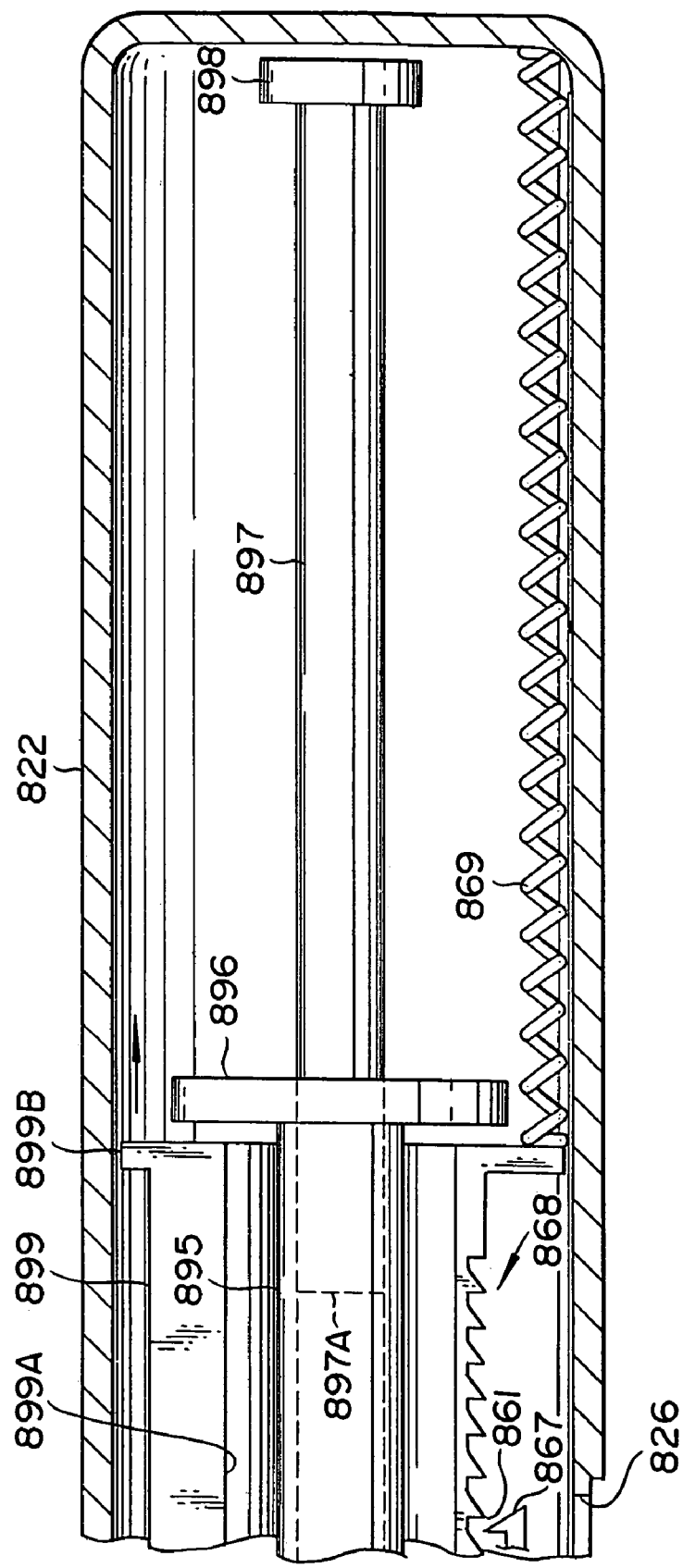
FIG. 36 is a sectional view of the rear end portion of the operating unit at the proximal end portion.
Figure 37:
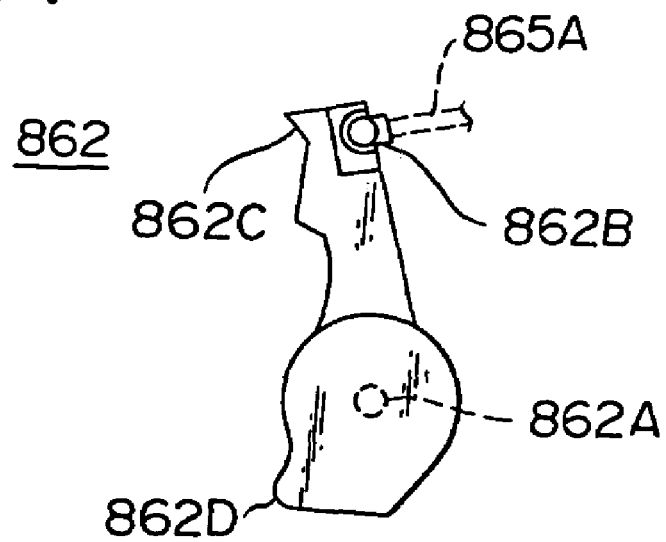
FIG. 37 is a plan view of a ratchet member possessed by a mechanism for injecting a liquid composition in the catheter.
Figure 38:
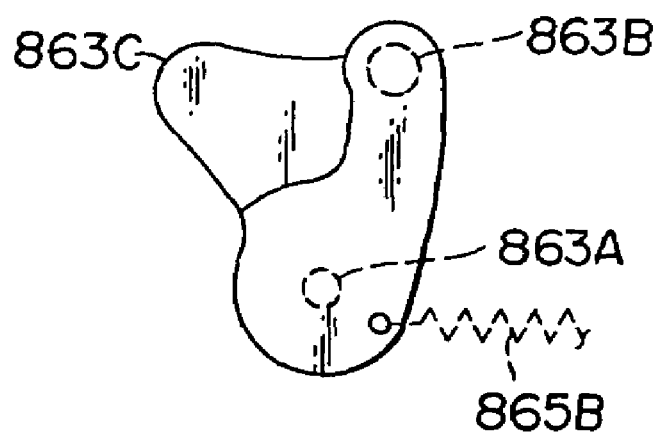
FIG. 38 is a plan view of a transmission member possessed by the mechanism for injecting the liquid composition.
Figure 39:
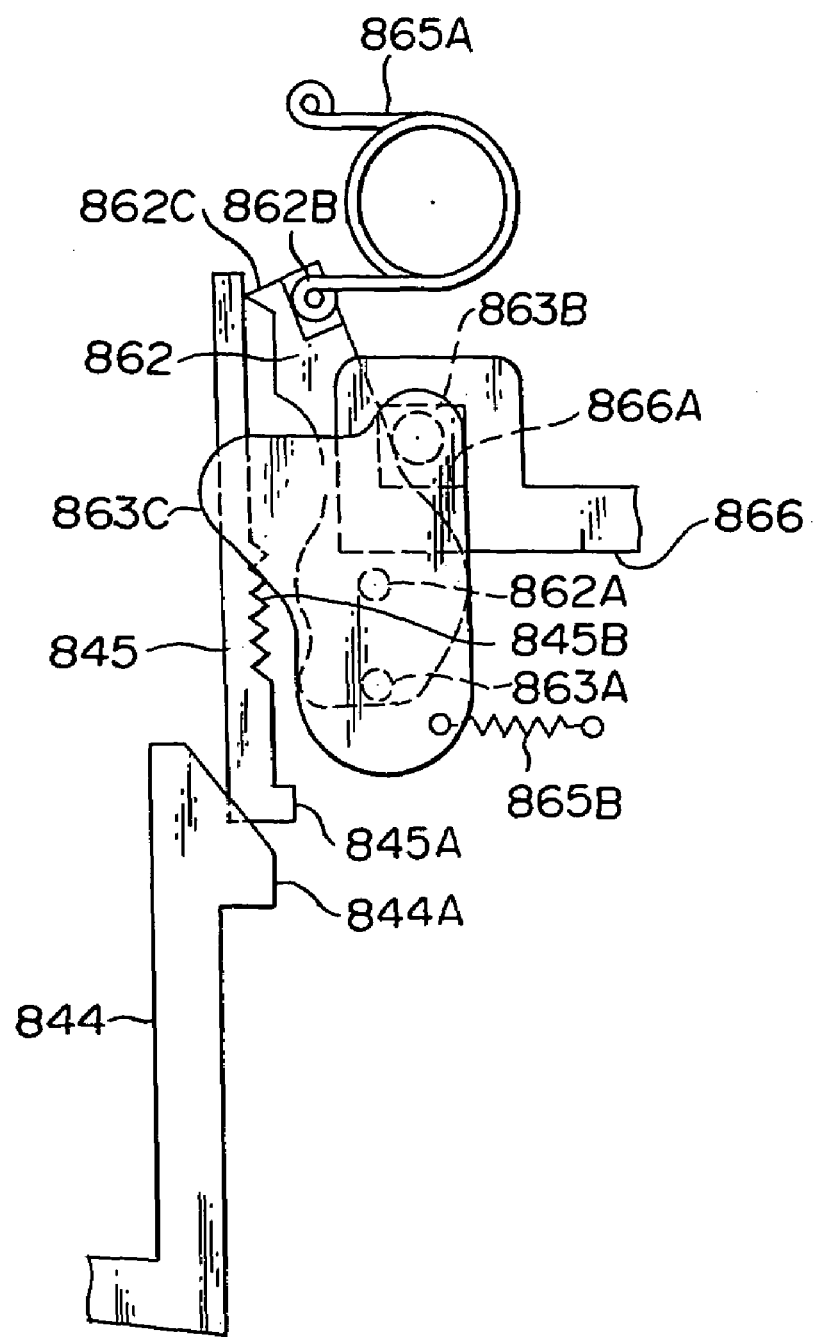
FIG. 39 is an enlarged detail of an essential part for illustrating the mechanism for injecting the liquid composition, depicting the mechanism in an inoperative state.
Figure 40:
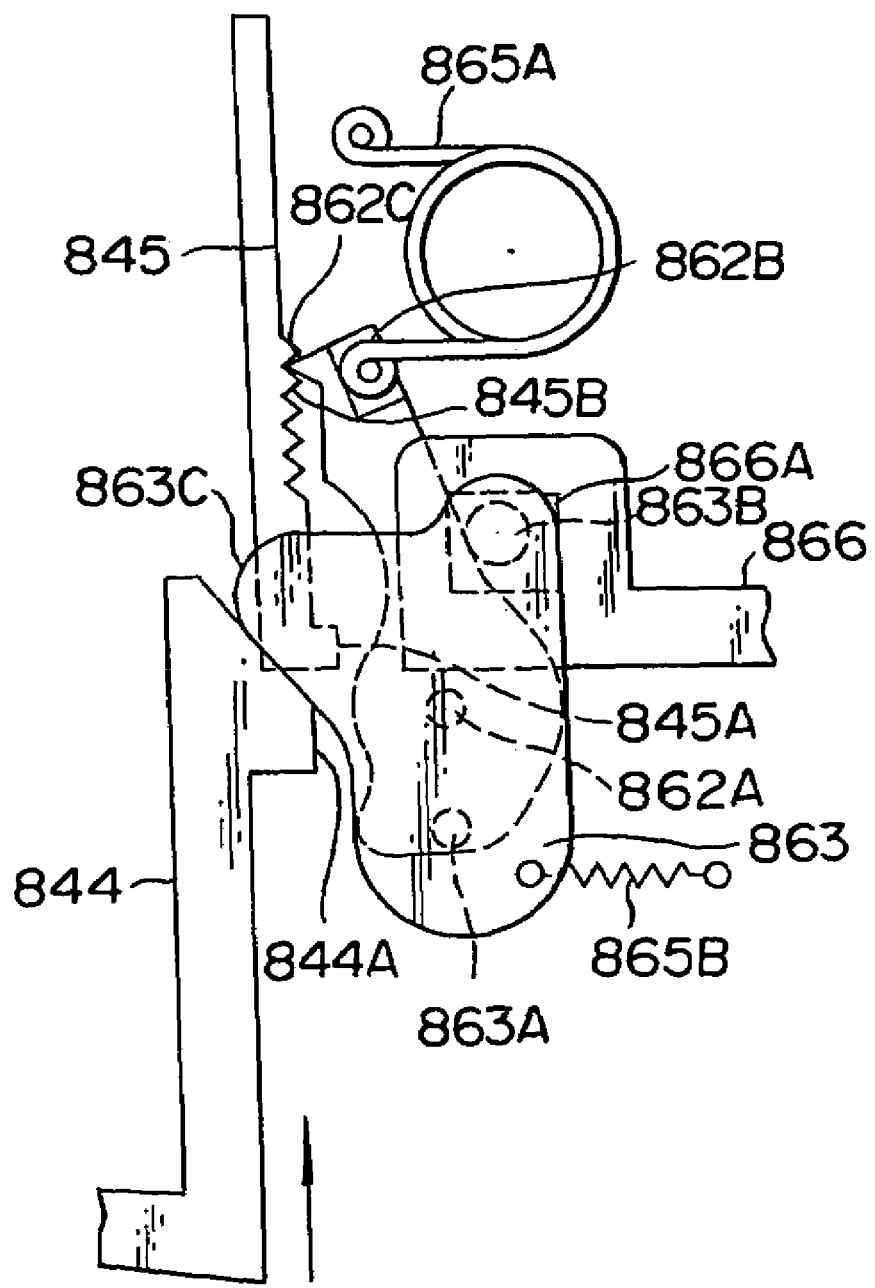
FIG. 40 is an enlarged detail for illustrating the mechanism in a state of starting operation continuing from the state of FIG. 39.
Figure 41:
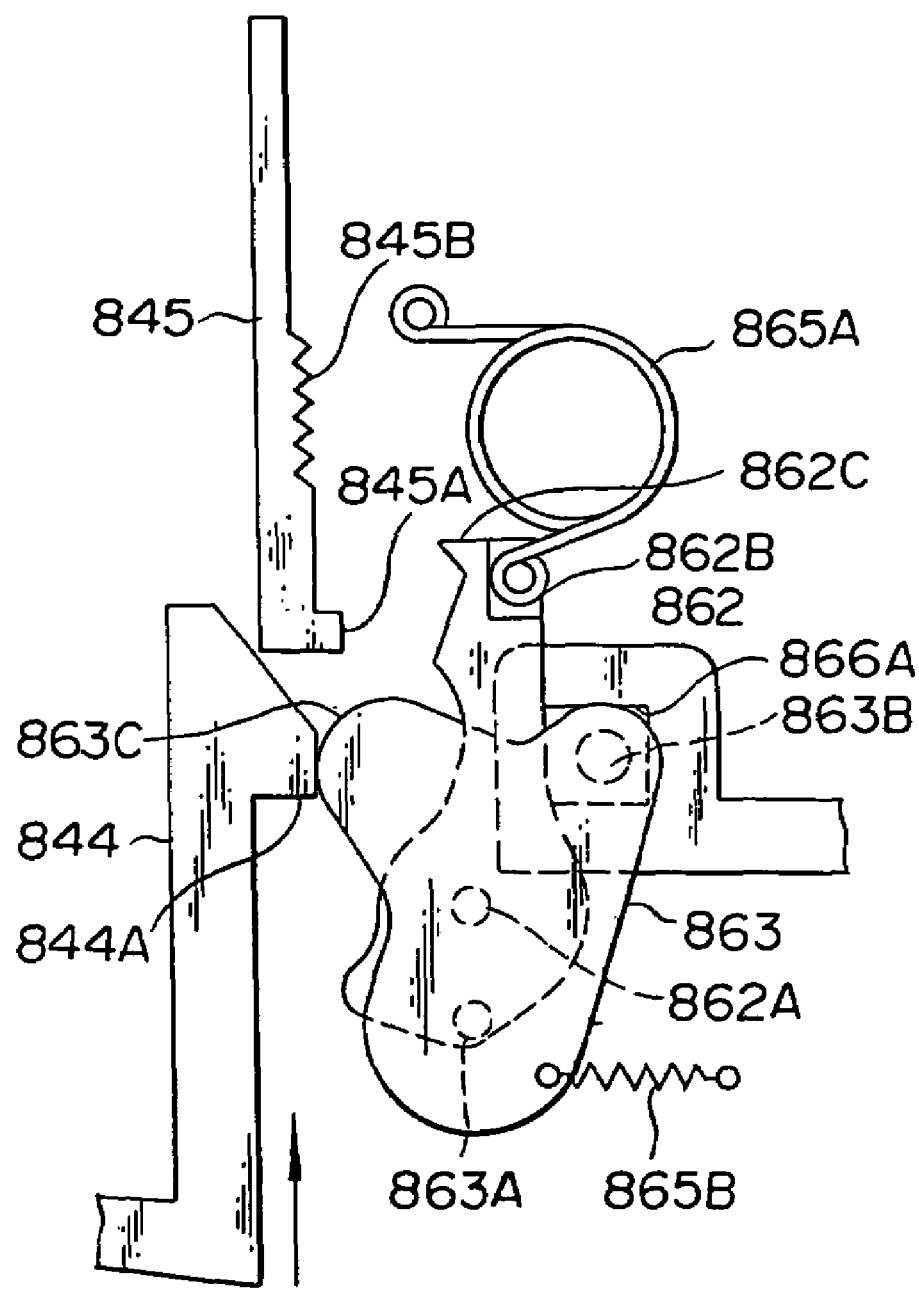
FIG. 41 is an enlarged detail for illustrating the mechanism in a state of completing operation continuing from the state of FIG. 40.

FIG. 35 and FIG. 36 are sectional views respectively of the intermediate portion and the rear portion of the operating unit 820. FIG. 37 and FIG. 38 are plan views respectively of a ratchet member and a transmitting member possessed by the mechanism for injecting the liquid composition of the catheter 810. FIG. 39 is an enlarged detail of an essential part for illustrating the mechanism for injecting the liquid composition, depicting the mechanism in an inoperative state, FIG. 40 is an enlarged detail for illustrating the mechanism in a state of starting operation continuing from the state of FIG. 39, and FIG. 41 is an enlarged detail for illustrating the mechanism in a state of completing operation continuing from the state of FIG. 40.

In the proximity of the operating button 840, a ratchet member 862, a transmitting member 863, the syringe driving member 866, a syringe holder 899, and the operating tab 860 are disposed.

The ratchet member 862 which is swingably supported around an axis 862A includes the connector 862B to which a spring (resilient member) 865A is connected, a projection 862C allowed to engage with a serrated portion 845B of the rack 845, and a projection 862D allowed to collide against the projection 845A of the rack 845. The spring 865A is fixed to the main case 822 and made to urge the ratchet member 862.

The transmitting member 863 which is swingably supported around a shaft 863A includes a connector to which a spring (resilient member) 865B is connected, and a projection 863B and an extension 863C which are used for moving the syringe driving member 866. The spring 865B is fixed to the main case 822 and is made to urge the transmitting member 863. The extension 863C is allowed to collide against a distal end 844A of the pressing member 844 of the operating button 840.

The syringe driving member 866 is in the shape of the letter d containing a rectangular part and an elongate arm extending from the rectangular part. The rectangular part forms an opening 866A in which the projection 863B is disposed. The arm possesses a leading end provided with a claw 867.

When the operating button 840 is pressed toward the interior of the main case 822, therefore, the mechanism for injecting the liquid composition shifts from the state of inaction, via the state of starting operation, to the state of completing action.

In the initial state or the state of inaction illustrated in FIG. 39, based on the urging force of the springs 865A, 865B, a projection 862C of the ratchet member 862 collides against the terminal part not forming the serrated portion 845B of the rack 845 and the projection 863B of the transmitting member 863 retains the syringe driving member 866 at the initial position through the opening 866A in which the projection 863B is disposed.

In the state of half press or the state of starting operation illustrated in FIG. 40, the pressing member 844 and the rack 845 of the operating button 840 are moved toward the interior. The projection 862C of the ratchet member 862 slides on a flat portion without the serrated portion 845B, and engages with the serrated portion 845B of the rack 845. Since the ratchet member 862 is movable around the shaft 862A, the projection 862C follows the movement of the rack 845 and engages sequentially with the adjoining serrated portion 845B. The flat portion mentioned above is so formed as to correspond to actuating timing of the mechanism for driving the injection needle. That is, the length of the flat portion is so set that the mechanism for injecting the liquid composition is actuated after completion of the projecting motion of the injection needle 890 generated by the mechanism for driving the injection needle.

The union between the projection 862C and the serrated portion 845B results in fixing the rack 845 and obstructing the operating button 840 from retracting or returning to the home position and preventing it from malfunctioning. Further, the union between the projection 862C and the serrated portion 845B results in giving rise to a clicking sensation and consequently enabling the state of pressing the operating button 840 to be comprehended.

Meanwhile, the extension 863C of the transmitting member 863 collides against the distal end 844A of the pressing member 844. Since the transmitting member 863 is movable around the shaft 863A as the center, the transmitting member 863 is gradually revolved by pressing the extension 863 in consequence of the movement of the distal end 844A of the pressing member 844. The projection 863B of the transmitting member 863 presses the inner periphery of the opening 866A of the syringe driving member 866 and moves the syringe driving member 866 toward the rear end side of the main case 822.

In the state of complete press or the state of completing the action illustrated in FIG. 41, the pressing member 844 and the rack 845 of the operating button 840 reach the most leading end positions. At this time, the ratchet member 862 has separated from the serrated portion 845B of the rack 845, the transmitting member 863 is located at the position of the largest revolution, and the syringe driving member 866 has completed the drive of itself.

When the press of the operating button 840 is released, the operating button 840 returns to the initial state on the basis of the urging force of the spring 846. Meanwhile, the ratchet member 862 returns to the initial state on the basis of the collision of the projection 862D against the protrusion 845A of the rack 845 and the urging force of the spring 865A. The transmitting member 863 returns to the initial state on the basis of the urging force of the spring 865B. In this case, the projection 863B of the transmitting member 863 presses the inner periphery of the opening 866A of the syringe driving member 866 and is accompanied by the syringe driving member 866 to the initial state.

The syringe holder 899 includes a recess 899A, a radial expansion part 899B, and the rack 168. The recess 899A has an arcuate cross section and allows the outer periphery of the syringe 895 detachably disposed thereon. The radial expansion part 899B is urged by a spring (resilient member) 869 toward the operating button side while the inside diameter of the radial expansion part 899B is smaller than the outside diameter of a flange 896 of the outer cylinder. The rack 868 includes a plurality of right triangular teeth 868A and is disposed on the side opposite the syringe driving member 866 and allowed to engage with the claw 867 of the syringe driving member 866.

When the rack 868 and the claw 867 are in union, the movement of the syringe driving member 866 induces the syringe holder 899 to move in the direction of the rear end side of the main case 822. As a result, the radial expansion part 899B of the syringe holder 899 collides against the flange 896 of the outer cylinder and is accompanied by the outer cylinder of the syringe 895. Preferably, a supporting bar may be inserted in the interior of the spring 869 to prevent the spring 869 from producing unnecessary deformation.

A push rod (plunger) 897 is slidably inserted into the outer cylinder while a proximal end portion 898 of the push rod 897 is fixed to the main case 822. As a result, a distal end 897A of the push rod 897 moves in the outer cylinder toward the nozzle 894, and pushes the liquid composition held inside the outer cylinder of the syringe 895. That is, for the purpose of injecting the liquid composition, the proximal end portion 898 of the push rod 897 does not need to be pressed and moved. Since it is no longer necessary to dispose any operating space behind the proximal end portion 898 of the push rod 897, the rear portion of the main case 822 becomes compact and the total length of the operating unit 820 can be shortened.

When the operating button 840 is pressed toward the interior of the main case 822 as described above, the ratchet member 862 and the transmitting member 863 are set driving to move the syringe driving member 866 toward the rear end side of the catheter after the motion for protruding the injection needle 890 by the injection needle driving mechanism is completed. Since the syringe driving member 866 is accompanied by the outer cylinder of the syringe 895, the push rod 897 moves toward the nozzle 894 in the interior of the outer cylinder of the syringe 895.

That is, the mechanism for injecting the liquid composition according to Embodiment 4 is based on converting the descending motion induced by the pressing motion of the operating button 840 via the ratchet mechanism to the advancing motions of the syringe driving member 866, the syringe holder 899, and the outer cylinder of the syringe 895, and consequently effecting relative change of the position of the push rod 897 in the interior of the outer cylinder.

Figure 42:
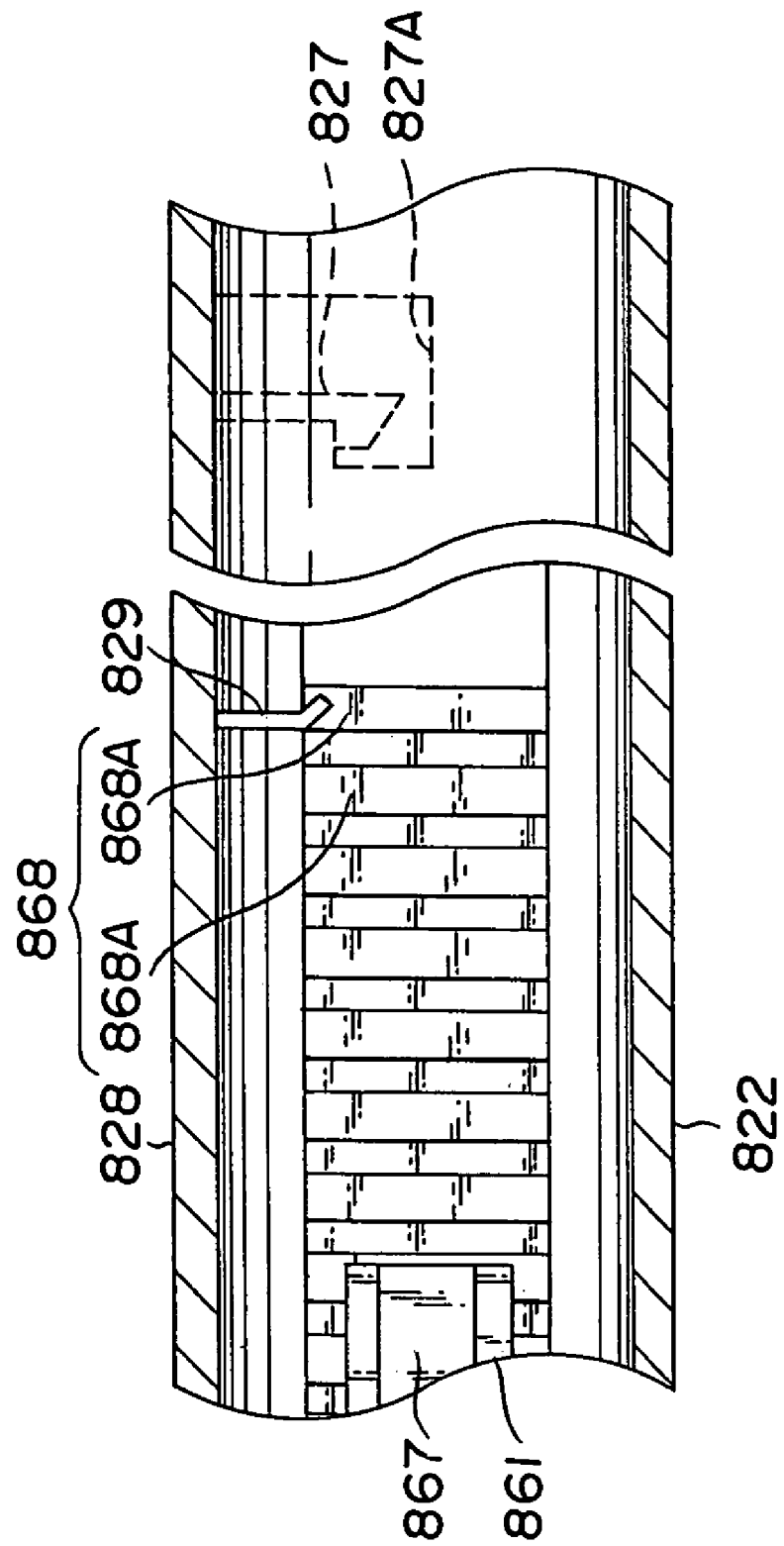
FIG. 42 is an enlarged detail of an essential part for illustrating a mechanism for restraining a syringe holder of the catheter.

FIG. 42 is an enlarged detail of an essential part for illustrating a mechanism for restraining a syringe holder 899 of the catheter.

The lid 828 of the main case 822 has elastic hooks 827, 829 formed thereon. The hook 827, when engaged with a recess 827A formed in the main case 822, is enabled to fix the lid 828 to the main case 822. The hook 829 does not interfere with the movement just mentioned because it slides along the slanted surface of a tooth 868A when the rack 868 moves toward the rear end side. In contrast, the hook 829 collides against the vertical face of the tooth 868A and restrains the rack 868 when the rack 868 is moved in the opposite direction.

As a result, the hook 829 functions as a stopper for preventing the syringe holder 899 with the rack 868 formed there on from moving backward. When the union between the hook 827 and the recess 827A is manually released and the lid 828 is opened, the hook 829 formed on the lid 828 separates from the rack 868 and releases the union between the hook 829 and the rack 868. Since the syringe holder 899 is urged by the spring 869 toward the operating button side, the syringe holder 899 moves backward and returns to the home position.

Figure 43:
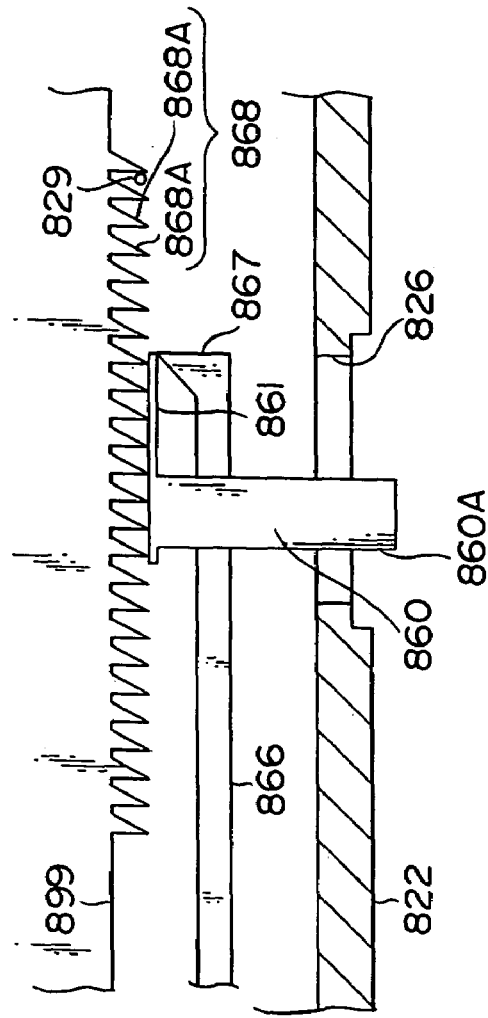
FIG. 43 is an enlarged detail of an essential part for illustrating a mechanism for adjusting the amount of injection of a liquid composition in the catheter, depicting the initial state assumed when the maximum amount of injection is set.
Figure 44:
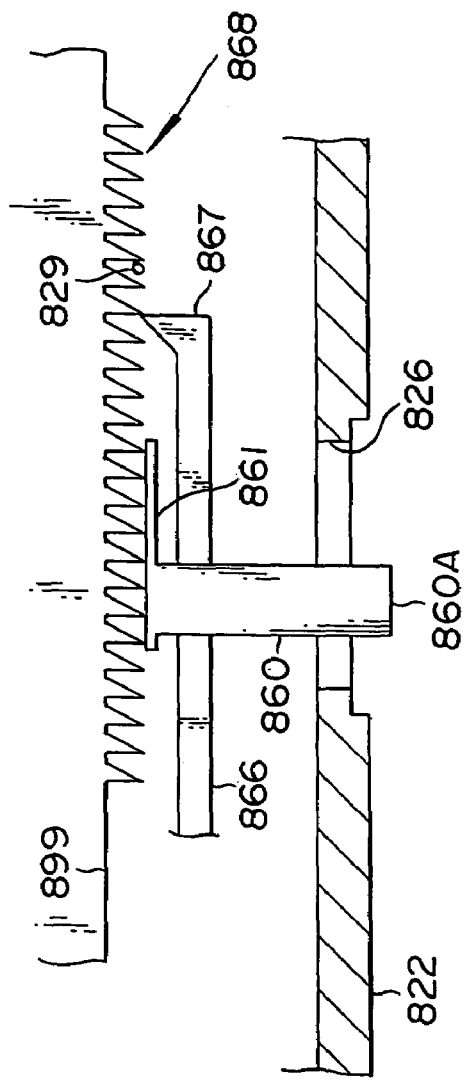
FIG. 44 is an enlarged detail of an essential part for illustrating the final state assumed when the maximum amount of injection is set according to FIG. 43.
Figure 45:
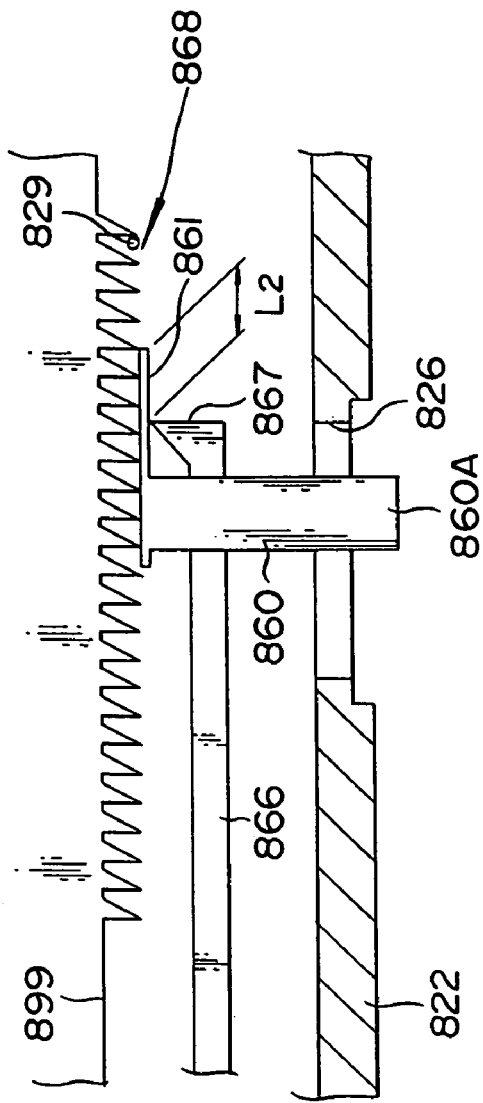
FIG. 45 is an enlarged detail of an essential part for illustrating the initial state assumed when the injection is set at an amount smaller than the maximum amount of injection according to FIG. 43.
Figure 46:
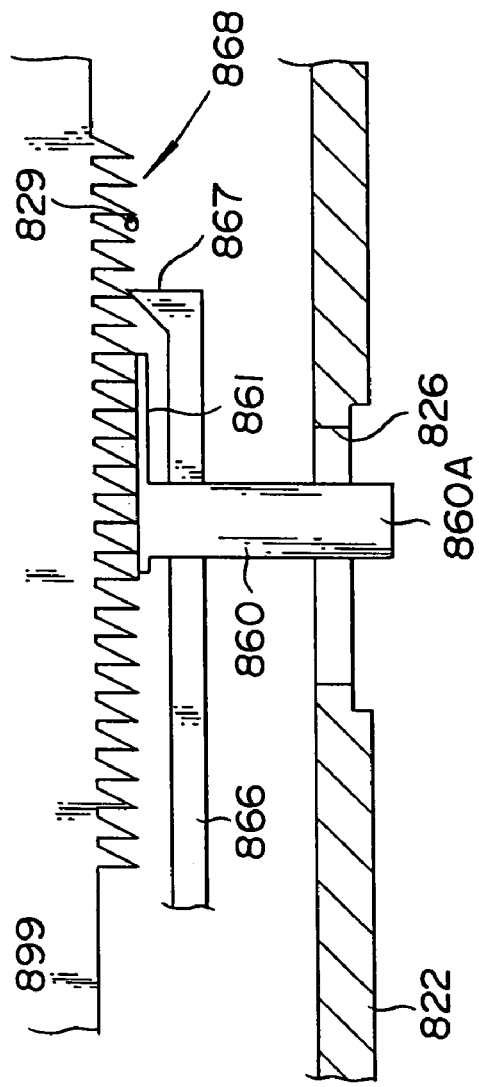
FIG. 46 is an enlarged detail of an essential part for illustrating the final state assumed when the injection is set at a small amount according to FIG. 45.

FIG. 43 is an enlarged detail of an essential part for illustrating a mechanism for adjusting the amount of injection of a liquid composition in the catheter, depicting the initial state assumed when the maximum amount of injection is set. FIG. 44 is an enlarged detail of an essential part for illustrating the final state assumed when the maximum amount of injection is set according to FIG. 43. FIG. 45 is an enlarged detail of an essential part for illustrating the initial state assumed when the injection is set at an amount smaller than the maximum amount of injection according to FIG. 43. FIG. 46 is an enlarged detail of an essential part for illustrating the final state assumed when the injection is set at a small amount according to FIG. 45.

The operating tab 860 has the shape of the letter L and includes a projection 860A exposed to the exterior and a plate 861 extending the interior of the main case 822. The projection 860A is movably disposed in the opening 826 formed in the main case 822. The opening 826 has an oblong shape. The plate 861 is disposed parallel to the opposite rack 868 of the syringe holder 899 and is allowed to collide freely with the rack 868. As a result, the plate 861 interferes with the union between the claw 867 of the syringe driving member 866 and the rack 868.

When the projection 860A is set so that the leading end of the claw 867 in the initial position is positioned on the end face of the plate 861 (refer to FIG. 43), the claw 867 engages with the rack 868 and drives the syringe holder 899 as soon as the syringe driving member 866 is moved (refer to FIG. 44). In this case, since the plate 861 avoids obstructing the union between the claw 867 and the rack 868, the amount of movement of the syringe driving member 866 and the amount of movement of the syringe holder 899 substantially agree and the amount of injection of the liquid composition is maximized.

When the projection 860A is so set that the leading end of the claw 867 at the initial position assumes a position parted by a distance of $L_2$ from the end face of the plate 861 (refer to FIG. 45), the movement of the syringe driving member 866 causes the claw 867 to slide on the plate 861. Then, the claw 867, after completing the movement over a distance $L_2$, engages with the rack 868 and drives the syringe holder 899 (refer to FIG. 46).

In this case, the amount of movement of the syringe driving member 866 and the amount of movement of the syringe holder 899 do not accord, and the amount of movement of the syringe holder 899 becomes an amount left by the distance $L_2$ subtracted from the amount of movement of the syringe driving member 866. That is, while the amount of movement of the syringe driving member 866 indeed is fixed, the amount of injection of the liquid composition is properly controlled by adjusting the set position of the projection 860A and altering the distance $L_2$.

As described above, the mechanism for adjusting the amount of injection according to Embodiment 4 is based on obstructing in a proper range the drive transmission which induces the movement of the syringe holder 899.

Now, one example of the method of using the catheter 810 will be explained below. The target site is a cardiac tissue, for example, and the liquid composition to be injected is a therapeutic composition intended to cure the diseased region of the cardiac tissue.

First, the operator fills the syringe 895 with the liquid composition. He opens the lid 828 by releasing the union between the hook 827 of the lid 828 and the recess 827A of the main case 822. Consequently, the hook 829 formed in the lid 828 separates from the rack 868 and the union between the hook 829 and the rack 868 is released. Since the syringe holder 899 is urged by the spring 869 toward the operating button side, the syringe holder 899 moves back and returns to the home position (refer to FIG. 42).

The syringe 895 holding the liquid composition is disposed in the interior of the main case 822 and the tube 892 connected to the insertion member 880 is mounted on the nozzle 894 of the syringe 895 (refer to FIG. 33).

The amount of protrusion of the injection needle 890 disposed at the distal end portion 882 of the insertion member 880 is adjusted by turning the cap 830 to alter the relative positions of the insertion member 880 and the sheath portion 870 (refer to FIG. 32). The amount of injection of the liquid composition is adjusted by moving the projection 860A of the operating tab 860 to obstruct in a proper range the transmission inducing the movement of the syringe holder 899 (refer to FIGS. 43-46).

The lock tab 848 is moved after the setting of the mechanism for adjusting the amount of protrusion and the mechanism for adjusting the amount of injection is completed (refer to FIG. 34). The projection 849A of the lock tab 848 and the recess 847 of the operating button 840 are engaged to lock the operating button 840.

Thereafter, the distal end portion 872 of the sheath portion 870 of the catheter 810, for example, is inserted into the living body through an aperture formed in advance between adjacent ribs and guided from the outside into the cardiac tissue under observation with an endoscope and brought to close contact with the cardiac tissue.

The operator releases the lock of the operating button 840 with the lock tab 848, presses the operating button 840 with the finger of his one hand taking the operating unit 820, and forces the operating button 840 toward the interior of the main case 822.

The operating button 840, as soon as it starts moving, actuates the injection needle driving mechanism and the transmitting member 850 of the injection needle driving mechanism, by revolving, moves the needle driving member 855 toward the cap 830 (refer to FIG. 33). Since the insertion member 880 is fixed to the needle driving member 855, the injection needle 890 disposed at the distal end portion 882 of the insertion member 880 protrudes from the distal end portion 872 of the sheath portion 870, depending on the setting of the mechanism for adjusting the amount of protrusion.

When the operating button 840 is further pressed toward the interior of the main case 822, the mechanism for injecting the liquid composition is actuated to drive the ratchet member 862 and the transmitting member 864 (refer to FIG. 40 and FIG. 41). Since the syringe driving member 866 moves toward the rear end side of the catheter with the outer cylinder, the push rod 897 moves in the inside the outer cylinder toward the nozzle 894. As a result, the liquid composition held in the interior of the syringe 895 is sent out and injected through the injection needle 890 into the interior of the target region.

The drive of the syringe driving member 866 is completed when the operating button 840 reaches the farthest leading end position. As a result, the supply of the liquid composition in the prescribed amount conforming to the setting of the mechanism for adjusting the amount of injection is completed (refer to FIG. 42).

When the press of the operating button 840 is released, the operating button 840, the injection needle driving mechanism, and the mechanism for injecting the liquid composition are returned by the urging force of the spring to their home positions and the injection needle 890 retracts to the interior of the distal end portion 872 of the sheath 870.

The operator, by moving the catheter 810 to the next target tissue and repeating the procedure described above, is enabled to effect continuous injection of the therapeutic composition in a prescribed amount to a plurality of sites of the cardiac tissue.

The operating unit 820 of the catheter 810 according to Embodiment 4 includes the operating button 840 which is capable of continuously repeating a step of protruding the injection needle 890 from the distal end portion 872 of the sheath 870, a step of puncturing the target region and injecting the liquid composition to the target region with the protruded injection needle 890, and a step of retracting the injection needle 890 into the lumen 871 of the distal end portion 872 of the sheath portion 870 as a series of operations. Thus, the convenient catheter 810 with proper operability can be provided.

Figure 47:
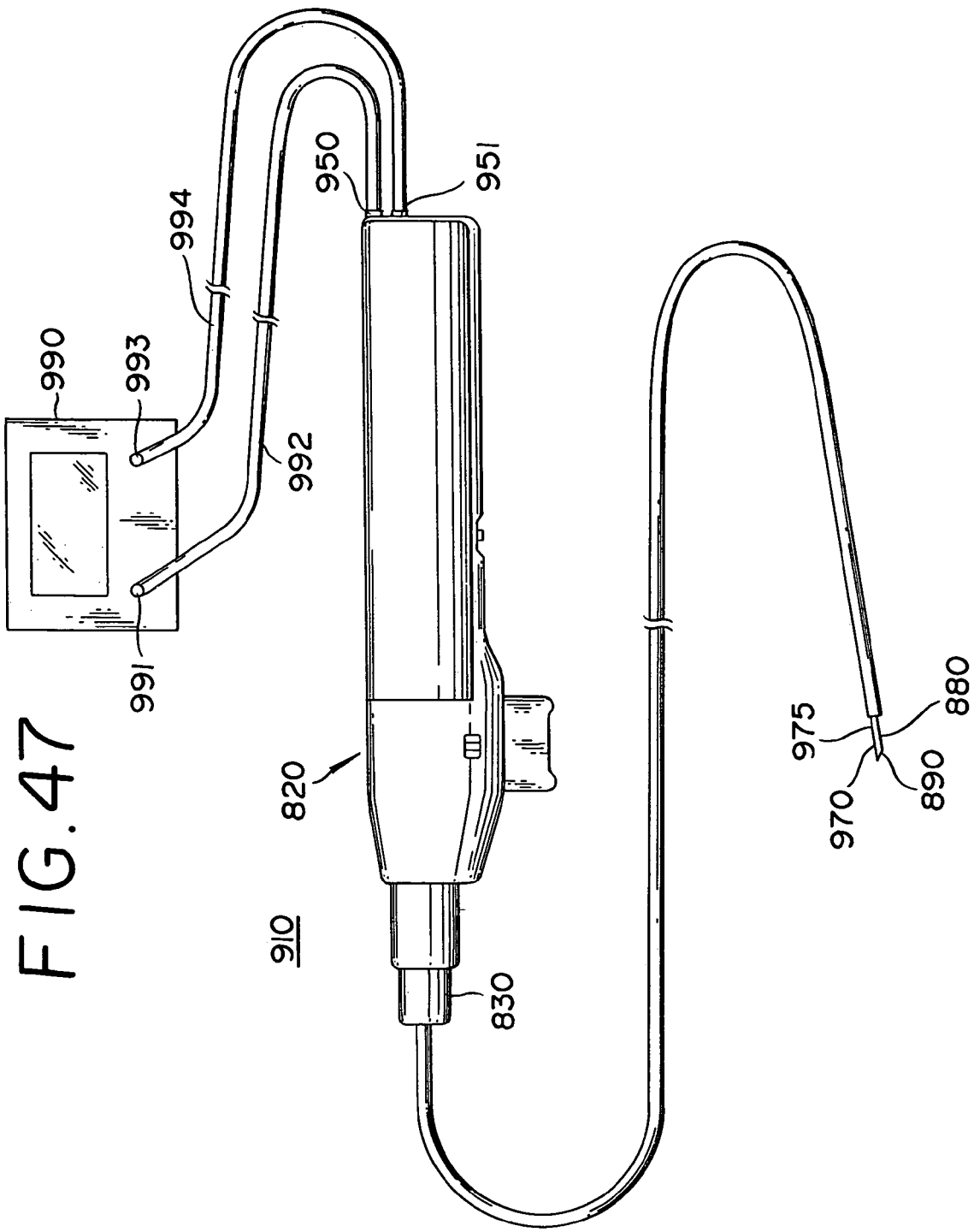
FIG. 47 is a schematic view for illustrating an example of the modification of the catheter according to Embodiment 4.
Figure 48:
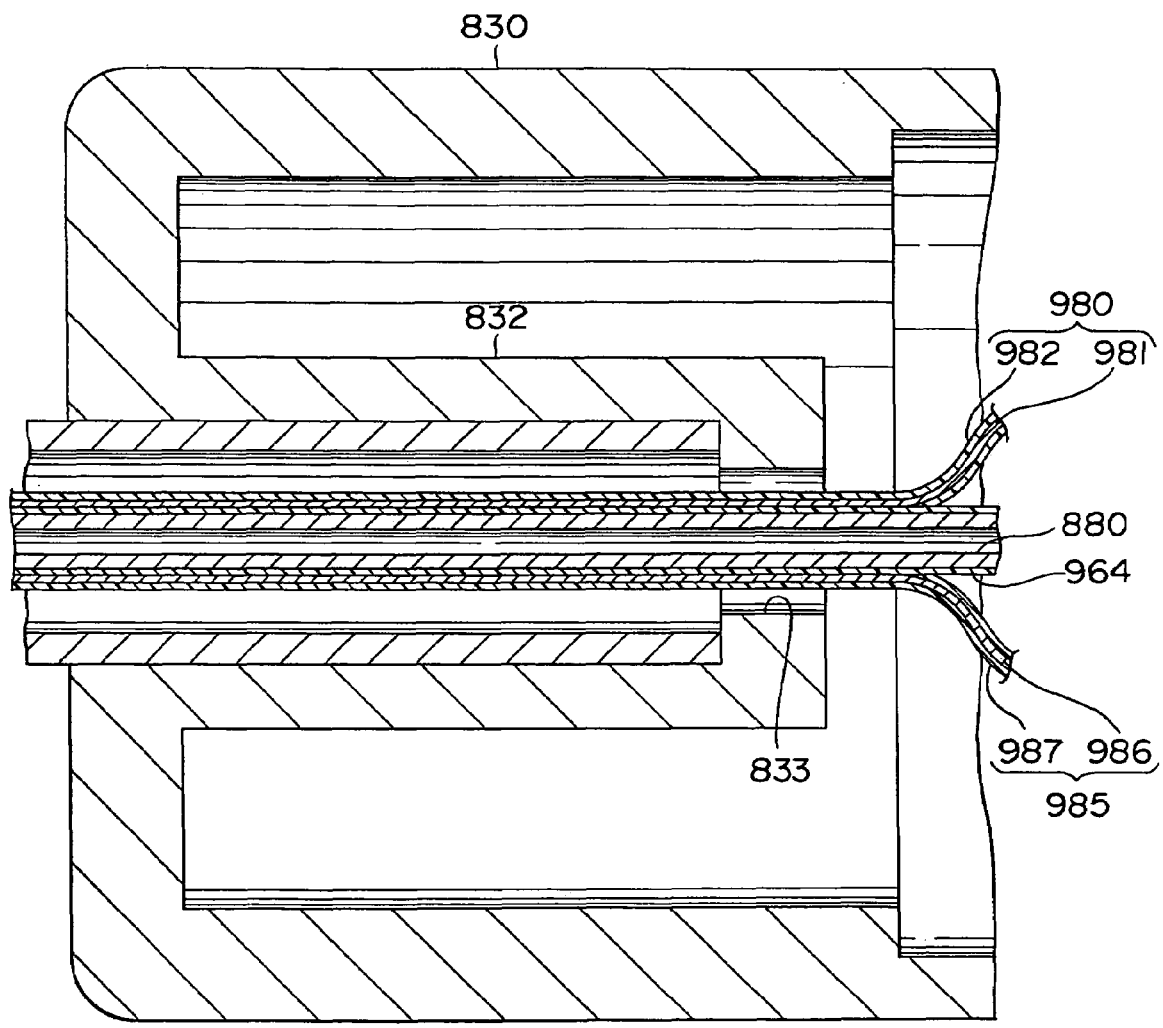
FIG. 48 is a sectional view for illustrating the front end portion of the operating unit at the proximal end portion shown in FIG. 47.

FIG. 47 is a schematic view for illustrating an example of the modification of the catheter according to Embodiment 4. FIG. 48 is a sectional view for illustrating the front end portion of the operating unit at the proximal end portion shown in FIG. 47.

A catheter 910 roughly differs from the catheter 810 according to Embodiment 4 in being provided with electrodes 970, 975 for measuring the impedance and output terminals 950, 951 for connection to an impedance analyzer 990.

The impedance analyzer 990 includes input terminals 991, 993 connected via cords 992, 994 to the output terminals 950, 951. The electrodes 970, 975 which adopt a configuration illustrated in FIG. 5, for example, are disposed in the distal end portion of the insertion member 880 near the bevel of the injection needle 890. The output terminals 950 and 951 are disposed at the rear end of the operating unit 820.

The outer periphery of the insertion member 880 is coated with an electrical insulator 964. Wires 980, 985 which extends on the surface of the electrical insulator 964 include conductors 981, 986 with terminals connected to the electrodes 970, 975 and electrical insulators 982, 987 covering the conductors 981, 986.

The wires 980, 985 extend from the insertion member 880 at a position separated by a prescribed distance from the opening 833 formed in the recess 832 of the cap 830. The prescribed distance mentioned above is so set that the movement of the insertion member 880 for inducing protrusion of the injection needle 890 will not be obstructed.

Since the interior of the operating unit 820 has no partition wall formed in a direction intersecting the longitudinal direction, the wires 980, 985 easily extend in the interior of the operating unit 820 and are connected to the output terminals 950, 951 disposed at the rear end thereof.

Thus, the electrodes 970, 975 for measuring the impedance are connected to the output terminals 950, 951 disposed at the rear end of the operating unit 820 and the impedance analyzer 990 is enabled to detect the puncture made by the injection needle 890 on the basis of the impedance values measured by the electrodes 970, 975.

As described above, this invention is applicable to the catheter according to Embodiment 4and is capable of providing a catheter and a catheter system which repress invasion, infallibly accomplishes the puncture of the target issue with an injection needle and the injection of the therapeutic composition to the site, and manifests proper operability and enjoys convenience as well. With respect to the above catheter as shown in FIGS. 47, 48, it can be further made by persons who have common knowledge in the technical field to which the inventions pertains, that the electrodes 970, 975 for measuring the impedance are replaced with other electrodes for various use such as electrodes used as pressure sensors.

It is obvious that this invention is not limited to the particular embodiments shown and described above but may be variously changed and modified without departing from the technical concept of this invention.

The catheter according to this invention may be applied to gene therapy and cell therapy.

The gene therapy is a therapy for ischemic cardiopathy, for example. The injection of liquid composition for gene therapy (such as, for example, a composition containing nucleic acid) with an injection needle built in a catheter is at an advantage in repressing invasion.

The cell therapy is a method of therapy for improving the cardiac function, for example, by transplanting a new cell (myocardiblast, myeloblast, smooth muscle cell, osteoblast, peripheral blood tube cell, and cell originating in cord blood) from the exterior. The injection needle which is built in the catheter, therefore, may be applied to the transplantation of osteoblast, for example, to the site of infarction and the neighborhood thereof.

This invention does not need to be particularly restricted to the application for the therapy of the heart but may be applied to the therapy directed toward the neogenesis of the lower extremity.

This application is based on Japanese Patent Application Nos. 2003-85435 filed on Mar. 26, 2003 and 2003-90226 filed on Mar. 28, 2003 and 2004-44320 filed on Feb. 20, 2004, the contents of which are hereby incorporated by reference.

What is claimed is:

1. A catheter for percutaneous insertion comprising:
   a sheath portion with a lumen extending therein,
   an insertion member disposed slidably in the lumen of said sheath portion and provided with a distal end portion capable of protruding from a distal end portion of said sheath portion,
   an injection needle disposed in the distal end portion of said insertion member for injecting a therapeutic composition to a target tissue, and
   paired electrodes disposed in a distal end portion of the catheter for measuring impedance, both of said paired electrodes being disposed at said insertion member apart from the bevel of said injection needle, and at least one of said paired electrodes being constructed so as to move into the target tissue when the target tissue is punctured by said injection needle.

2. A catheter as claimed in claim 1, wherein said paired electrodes are disposed in the distal end portion of said insertion member.

3. A catheter as claimed in claim 2, wherein at least one of said paired electrodes is separated by not less than 1 mm from a leading end of the bevel of said injection needle relative to a longitudinal direction of said insertion member.

4. A catheter as claimed in claim 2, wherein said paired electrodes exist in a plurality of sets which are positioned as separated relative to a longitudinal direction of said insertion member.

5. A catheter as claimed in claim 4, wherein at least one of the electrodes composed of said plurality of sets of paired electrodes is parted by not less than 1 mm from a leading end of the bevel of said injection needle relative to the longitudinal direction of said insertion member.

6. A catheter as claimed in claim 1, wherein one of said paired electrodes is positioned not more than 3 mm from a leading end of the bevel of said injection needle relative to the longitudinal direction of said insertion member.

7. A catheter as claimed in claim 6, wherein said one of said paired electrodes is positioned not less than 1 mm from the leading end of the bevel of said injection needle relative to the longitudinal direction of said insertion member.

8. A catheter as claimed in claim 6, wherein said paired electrodes exist in a plurality of sets and electrodes disposed in the distal end portion of said insertion member are positioned as individually parted relative to a longitudinal direction of said insertion member.

9. A catheter as claimed in claim 8, wherein at least one of the electrodes disposed in the distal end portion of said insertion member is separated by not less than 1 mm from a leading end of the bevel of said injection needle relative to the longitudinal direction of said insertion member.

10. A catheter as claimed in claim 1, wherein the distal end portion of said sheath portion is provided with a through-hole communicating with the lumen of said sheath portion.

11. A catheter as claimed in claim 10, wherein said through-hole is separated by not less than 1 mm from an end face of the distal end portion of said sheath portion relative to a longitudinal direction of said insertion member.

12. A catheter as claimed in claim 1, wherein said target tissue is a heart.

13. A catheter system comprising:
    a catheter for percutaneous insertion including a sheath portion with a lumen extending therein, an insertion member disposed slidably in the lumen of said sheath portion and provided with a distal end portion capable of protruding from a distal end portion of said sheath portion, and an injection needle disposed in the distal end portion of said insertion member for injecting a therapeutic composition to a target tissue,
    paired electrodes disposed in a distal end portion of said catheter for measuring impedance, both of said paired electrodes being disposed at said insertion member apart from the bevel of said injection needle, and
    a puncture detecting device to which conductors extending from said paired electrodes are able to be connected for detecting a puncture by said injection needle based on impedance values measured by said paired electrodes.

14. A catheter system as claimed in claim 13, wherein one of said paired electrodes is positioned more toward a proximal end side of said catheter than the other of said paired electrodes.

15. A method for injecting a therapeutic composition with a catheter including a sheath portion with a lumen extending therein, an insertion member disposed slidably in the lumen of said sheath portion and provided with a distal end portion capable of protruding from a distal end portion of said sheath portion, an injection needle disposed in the distal end portion of said insertion member for injecting a therapeutic composition to a target tissue, and paired electrodes disposed in a distal end portion of the catheter for measuring impedance, both of said paired electrodes being disposed at said insertion member apart from the bevel of said injection needle, said method comprising:
    inserting said catheter into a living body and advancing it to a neighborhood of the target tissue, and measuring impedance with said paired electrodes, moving said insertion member in a distal end direction relative to said sheath portion, and protruding said injection needle from the distal end portion of said sheath portion to puncture the target tissue while moving one of said paired electrodes from a neighborhood of the target tissue into the target tissue; and
    injecting the therapeutic composition through said injection needle into the target tissue after a change is detected in the impedance values as measured by said paired electrodes.

* * * * *